(12) United States Patent
Foo et al.

(10) Patent No.: US 8,088,943 B2
(45) Date of Patent: Jan. 3, 2012

(54) HYDROCYANATION OF PENTENENITRILES

(75) Inventors: Thomas Foo, Wilmington, DE (US); James Michael Garner, Wilmington, DE (US); Ron Ozer, Arden, DE (US); Paul S. Pearlman, Thornton, PA (US)

(73) Assignee: Invista North America S.A R.L., Wilmington, DE (US)

( * ) Notice: Subject to any disclaimer, the term of this patent is extended or adjusted under 35 U.S.C. 154(b) by 411 days.

(21) Appl. No.: 12/353,584

(22) Filed: Jan. 14, 2009

(65) Prior Publication Data
US 2009/0182164 A1    Jul. 16, 2009

Related U.S. Application Data

(60) Provisional application No. 61/021,225, filed on Jan. 15, 2008.

(51) Int. Cl.
C07C 253/00    (2006.01)
(52) U.S. Cl. ...................................... 558/338
(58) Field of Classification Search .................... 558/338
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard et al. |
| 3,496,218 A | 2/1970 | Drinkard et al. |
| 3,522,288 A | 7/1970 | Drinkard, Jr. et al. |
| 3,536,748 A | 10/1970 | Drinkard et al. |
| 3,551,474 A | 12/1970 | Drinkard et al. |
| 3,564,040 A | 2/1971 | Downing et al. |
| 3,579,560 A | 5/1971 | Drinkard et al. |
| 3,631,191 A | 12/1971 | Kane et al. |
| 3,655,723 A | 4/1972 | Drinkard |
| 3,676,481 A | 7/1972 | Chia |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,852,325 A | 12/1974 | King |
| 3,852,327 A | 12/1974 | Druliner et al. |
| 3,853,754 A | 12/1974 | Gosser |
| 3,853,948 A | 12/1974 | Drinkard et al. |
| 3,864,380 A | 2/1975 | King et al. |
| 3,869,501 A | 3/1975 | Waddan |
| 3,903,120 A | 9/1975 | Shook, Jr. et al. |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,539,302 A | 9/1985 | Leyendecker et al. |
| 4,705,881 A | 11/1987 | Rapoport |
| 4,749,801 A | 6/1988 | Beatty et al. |
| 4,774,353 A | 9/1988 | Hall et al. |
| 4,874,884 A | 10/1989 | McKinney et al. |
| 4,990,645 A | 2/1991 | Back et al. |
| 5,107,012 A | 4/1992 | Grunewald |
| 5,302,756 A | 4/1994 | McKinney |
| 5,312,959 A | 5/1994 | Sieja et al. |
| 5,449,807 A | 9/1995 | Druliner |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,693,847 A | 12/1997 | Tung et al. |
| 5,696,280 A | 12/1997 | Shapiro |
| 5,709,841 A | 1/1998 | Reimer |
| 5,723,641 A | 3/1998 | Tam et al. |
| 5,773,637 A | 6/1998 | Cicha et al. |
| 5,821,378 A | 10/1998 | Foo et al. |

(Continued)

FOREIGN PATENT DOCUMENTS

AU    6522096    2/1997

(Continued)

OTHER PUBLICATIONS

Advances in Catalysis, vol. 33, 1985, pp. 1-46—C. A. Tolman, R. J. McKinney, W. C. Seidel, J. D. Druliner and W. R. Stevens.

(Continued)

Primary Examiner — Rei-tsang Shiao

(57) ABSTRACT

The invention provides a hydrocyanation process to produce adiponitrile and other dinitriles having six carbon atoms, in the presence of catalyst composition comprising a zero-valent nickel and at least one bidentate phosphorus-containing ligand wherein the bidentate phosphorus-containing ligand gives acceptable results according to at least one protocol of the 2-Pentenenitrile Hydrocyanation Test Method.

22 Claims, 4 Drawing Sheets

U.S. PATENT DOCUMENTS

Figure 1:
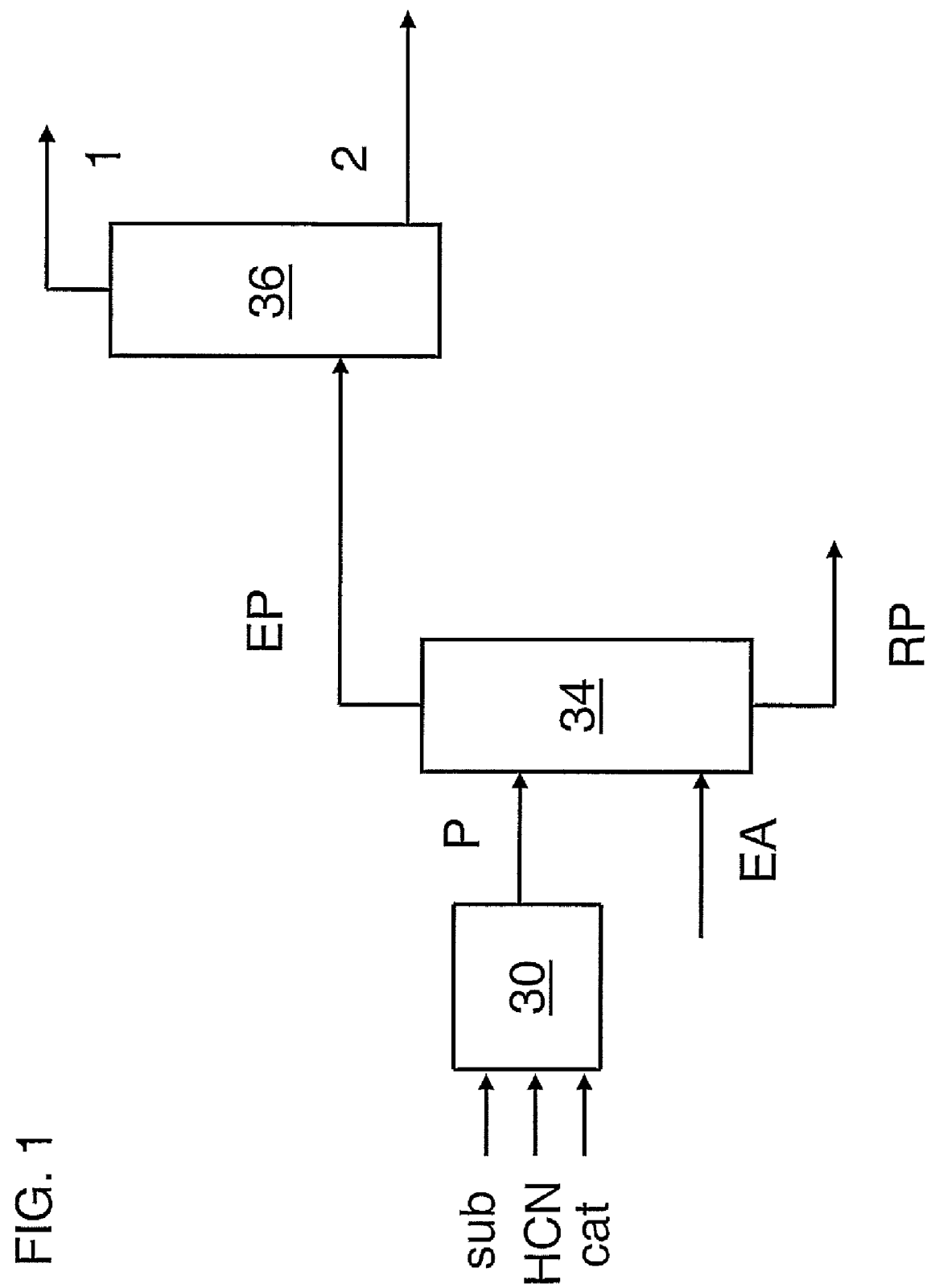

| | | | |
|---|---|---|---|
| 5,847,191 A | 12/1998 | Bunel et al. |
| 5,856,555 A | 1/1999 | Huser et al. |
| 5,908,805 A | 6/1999 | Huser et al. |
| 5,959,135 A | 9/1999 | Garner et al. |
| 5,981,772 A | 11/1999 | Foo et al. |
| 6,020,516 A | 2/2000 | Foo et al. |
| 6,069,267 A | 5/2000 | Tam |
| 6,090,987 A | 7/2000 | Billig et al. |
| 6,120,700 A | 9/2000 | Foo et al. |
| 6,121,184 A | 9/2000 | Druliner et al. |
| 6,127,567 A | 10/2000 | Garner et al. |
| 6,147,247 A | 11/2000 | Voit et al. |
| 6,169,198 B1 | 1/2001 | Fischer et al. |
| 6,171,996 B1 | 1/2001 | Garner et al. |
| 6,197,992 B1 | 3/2001 | Fischer et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,461,481 B1 | 10/2002 | Barnette et al. |
| 6,469,194 B2 | 10/2002 | Burattin et al. |
| 6,521,778 B1 | 2/2003 | Fischer et al. |
| 6,646,148 B1 | 11/2003 | Kreutzer et al. |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,893,996 B2 | 5/2005 | Chu et al. |
| 6,897,329 B2 | 5/2005 | Jackson et al. |
| 6,924,345 B2 | 8/2005 | Gagne et al. |
| 6,936,171 B2 | 8/2005 | Jackson et al. |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,659,422 B2 * | 2/2010 | Foo et al. ............... 558/338 |
| 7,700,795 B2 | 4/2010 | Haderlein et al. |
| 2003/0100802 A1 | 5/2003 | Shapiro |
| 2003/0100803 A1 | 5/2003 | Lu et al. |
| 2003/0135014 A1 | 7/2003 | Radu et al. |
| 2003/0212298 A1 | 11/2003 | Brasse et al. |
| 2004/0063991 A1 | 4/2004 | Burattin et al. |
| 2004/0106815 A1 | 6/2004 | Ritter |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0090677 A1 | 4/2005 | Bartsch et al. |
| 2005/0090678 A1 | 4/2005 | Bartsch et al. |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0115936 A1 | 5/2007 | Newton |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2007/0260086 A1 | 11/2007 | Rosier et al. |
| 2008/0015378 A1 | 1/2008 | Foo et al. |
| 2008/0015380 A1 | 1/2008 | Foo et al. |
| 2008/0015381 A1 | 1/2008 | Foo et al. |
| 2008/0015382 A1 | 1/2008 | Foo et al. |
| 2008/0071105 A1 | 3/2008 | Bartsch et al. |
| 2008/0076944 A1 | 3/2008 | Bartsch et al. |
| 2008/0083607 A1 | 4/2008 | Deckert et al. |
| 2008/0221351 A1 | 9/2008 | Bartsch et al. |
| 2008/0227214 A1 | 9/2008 | Jungkamp et al. |
| 2008/0227998 A1 | 9/2008 | Scheidel et al. |
| 2008/0242883 A1 | 10/2008 | Jungkamp et al. |
| 2008/0242885 A1 | 10/2008 | Jungkamp et al. |
| 2008/0242886 A1 | 10/2008 | Bartsch et al. |
| 2008/0275266 A1 | 11/2008 | Bartsch et al. |
| 2008/0281119 A1 | 11/2008 | Scheidel et al. |
| 2008/0281120 A1 | 11/2008 | Jungkamp et al. |
| 2009/0054671 A1 | 2/2009 | Haderlein et al. |

FOREIGN PATENT DOCUMENTS

| | | |
|---|---|---|
| AU | 199665220 | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |

| | | | | | | |
|---|---|---|---|---|---|---|
| CN | 1617892 A | 5/2005 | | EP | 784610 B1 | 2/1999 |
| CN | 1617900 A | 5/2005 | | EP | 757672 B1 | 6/1999 |
| CN | 1212293 C | 7/2005 | | EP | 792259 B1 | 8/1999 |
| CN | 1639176 A | 7/2005 | | EP | 804412 B1 | 12/1999 |
| CN | 1213051 C | 8/2005 | | EP | 1000019 A1 | 5/2000 |
| CN | 1665776 A | 9/2005 | | EP | 1001928 A1 | 5/2000 |
| CN | 1670139 A | 9/2005 | | EP | 1003716 A1 | 5/2000 |
| CN | 1674989 A | 9/2005 | | EP | 1019190 A1 | 7/2000 |
| CN | 1675172 A | 9/2005 | | EP | 755302 B1 | 10/2000 |
| CN | 1222358 C | 10/2005 | | EP | 929513 B1 | 4/2001 |
| CN | 1732148 A | 2/2006 | | EP | 881924 B1 | 5/2001 |
| CN | 1735460 A | 2/2006 | | EP | 8544858 B1 | 6/2001 |
| CN | 1245489 C | 3/2006 | | EP | 815073 B1 | 7/2001 |
| CN | 1740183 A | 3/2006 | | EP | 1144114 A3 | 9/2001 |
| CN | 1745062 A | 3/2006 | | EP | 1091804 B1 | 2/2002 |
| CN | 1767895 A | 5/2006 | | EP | 944585 B1 | 4/2002 |
| CN | 1260009 C | 6/2006 | | EP | 1000019 B1 | 2/2003 |
| CN | 1266424 C | 7/2006 | | EP | 911339 B1 | 4/2003 |
| CN | 1270543 C | 8/2006 | | EP | 1216268 B1 | 11/2003 |
| CN | 1274671 C | 9/2006 | | EP | 1350788 A3 | 11/2003 |
| CN | 1274699 C | 9/2006 | | EP | 1003607 B1 | 12/2003 |
| CN | 1835915 A | 9/2006 | | EP | 1003716 B1 | 2/2004 |
| CN | 1279088 C | 10/2006 | | EP | 1313743 B1 | 3/2004 |
| CN | 1847288 A | 10/2006 | | EP | 1414567 A1 | 5/2004 |
| CN | 1283620 C | 11/2006 | | EP | 1427695 A1 | 6/2004 |
| CN | 1857775 A | 11/2006 | | EP | 1438133 A1 | 7/2004 |
| CN | 1289539 C | 12/2006 | | EP | 1019190 B1 | 12/2004 |
| CN | 1293942 C | 1/2007 | | EP | 1140801 B1 | 2/2005 |
| CN | 1906150 A | 1/2007 | | EP | 1395547 B1 | 3/2005 |
| CN | 1914154 A | 2/2007 | | EP | 1001928 B1 | 4/2005 |
| CN | 1914155 A | 2/2007 | | EP | 1521736 A1 | 4/2005 |
| CN | 1914157 A | 2/2007 | | EP | 1521737 A1 | 4/2005 |
| CN | 1914158 A | 2/2007 | | EP | 1521738 A2 | 4/2005 |
| CN | 1914159 A | 2/2007 | | EP | 1603865 A1 | 12/2005 |
| CN | 1914160 A | 2/2007 | | EP | 1324976 B1 | 2/2006 |
| CN | 1914161 A | 2/2007 | | EP | 1214975 B1 | 3/2006 |
| CN | 1914162 A | 2/2007 | | EP | 1324978 B1 | 3/2006 |
| CN | 1914165 A | 2/2007 | | EP | 1648860 A1 | 4/2006 |
| CN | 1914166 A | 2/2007 | | EP | 891323 B1 | 6/2006 |
| CN | 1914167 A | 2/2007 | | EP | 1226147 B1 | 6/2006 |
| CN | 1914216 A | 2/2007 | | EP | 1438317 B1 | 6/2006 |
| CN | 19141156 A | 2/2007 | | EP | 1682561 A1 | 7/2006 |
| CN | 1307237 C | 3/2007 | | EP | 1448666 B1 | 8/2006 |
| CN | 1315790 C | 5/2007 | | EP | 1587621 B1 | 8/2006 |
| CN | 1318432 C | 5/2007 | | EP | 1713759 A1 | 10/2006 |
| CN | 1997624 A | 7/2007 | | EP | 1713761 A1 | 10/2006 |
| CN | 1331843 C | 8/2007 | | EP | 1713762 A1 | 10/2006 |
| CN | 101020641 A | 8/2007 | | EP | 1713766 A1 | 10/2006 |
| CN | 101035799 A | 9/2007 | | EP | 1716102 A2 | 11/2006 |
| CN | 101043946 A | 9/2007 | | EP | 1716103 A1 | 11/2006 |
| CN | 100348322 C | 11/2007 | | EP | 1716104 A1 | 11/2006 |
| CN | 100351227 C | 11/2007 | | EP | 1716105 A1 | 11/2006 |
| CN | 100352824 C | 12/2007 | | EP | 1716106 A1 | 11/2006 |
| CN | 100361966 C | 1/2008 | | EP | 1716107 A1 | 11/2006 |
| CN | 100364666 C | 1/2008 | | EP | 1716109 A2 | 11/2006 |
| DE | 1807088 U | 3/1960 | | EP | 1610893 B1 | 3/2007 |
| DE | 1807088 A1 | 6/1969 | | EP | 1621531 B1 | 3/2007 |
| DE | 2055747 A1 | 5/1971 | | EP | 1438132 B1 | 4/2007 |
| DE | 1593277 B2 | 8/1973 | | EP | 1799697 A1 | 6/2007 |
| DE | 1593277 C3 | 3/1974 | | EP | 1713764 B1 | 8/2007 |
| DE | 2700904 C2 | 10/1983 | | EP | 1713816 B1 | 8/2007 |
| DE | 68909466 T2 | 3/1994 | | EP | 1825914 A1 | 8/2007 |
| DE | 19953058 | 5/2001 | | EP | 1448620 B1 | 6/2008 |
| DE | 10046025 | 3/2002 | | EP | 1817108 B1 | 6/2008 |
| DE | 10136488 A1 | 2/2003 | | EP | 1713760 B1 | 7/2008 |
| DE | 10150285 A1 | 4/2003 | | EP | 1571172 B1 | 10/2008 |
| DE | 10350999 A1 | 6/2005 | | EP | 1988998 A1 | 11/2008 |
| DE | 102004004696 A1 | 8/2005 | | EP | 1265832 B1 | 5/2009 |
| EP | 0001899 B1 | 3/1982 | | EP | 1592659 B1 | 7/2009 |
| EP | 123438 B1 | 7/1987 | | EP | 1586598 B1 | 9/2009 |
| EP | 160296 B1 | 10/1988 | | EP | 2098106 A1 | 9/2009 |
| EP | 268448 B1 | 9/1991 | | EP | 1567478 B1 | 10/2009 |
| EP | 510689 A1 | 10/1992 | | EP | 1682559 B1 | 12/2009 |
| EP | 248643 B1 | 3/1993 | | EP | 1630166 B1 | 2/2010 |
| EP | 336314 B1 | 9/1993 | | FR | 1544656 A | 11/1968 |
| EP | 464691 B1 | 12/1993 | | FR | 2015115 A5 | 4/1970 |
| EP | 675871 B1 | 4/1997 | | FR | 1603513 A | 5/1971 |
| EP | 634395 B1 | 9/1997 | | FR | 2069411 A5 | 9/1971 |
| EP | 650959 B1 | 9/1997 | | FR | 2845379 B1 | 12/2004 |

| | | | | | | |
|---|---|---|---|---|---|---|
| FR | 2873696 | A1 | 2/2006 | JP | 11504262 A | 4/1999 |
| FR | 2873696 | B1 | 10/2006 | JP | 02911608 B2 | 6/1999 |
| GB | 0219474 | A | 7/1924 | JP | 11507297 A | 6/1999 |
| GB | 1104140 | A | 2/1968 | JP | 03001298 B2 | 1/2000 |
| GB | 1203702 | A | 9/1970 | JP | 03069915 B2 | 7/2000 |
| GB | 1213175 | A | 11/1970 | JP | 2001500135 A | 1/2001 |
| GB | 1429169 | A | 3/1976 | JP | 2001506250 A | 5/2001 |
| GB | 1429621 | A | 3/1976 | JP | 2001512097 A | 8/2001 |
| GB | 1436932 | A | 5/1976 | JP | 03205587 B2 | 9/2001 |
| GB | 1458322 | A | 12/1976 | JP | 2001516640 A | 10/2001 |
| GB | 1482909 | A | 8/1977 | JP | 3285878 B2 | 5/2002 |
| GB | 2007521 | A | 5/1979 | JP | 2002517473 A | 6/2002 |
| GB | 1565443 | A | 4/1980 | JP | 03320424 B2 | 9/2002 |
| GB | 1594694 | A | 8/1981 | JP | 2002533321 A | 10/2002 |
| GB | 2007521 | B | 6/1982 | JP | 03380543 B2 | 2/2003 |
| HK | 1025950 | A1 | 7/2003 | JP | 2003510385 A | 3/2003 |
| HK | 1026383 | A1 | 7/2004 | JP | 2003526688 A | 9/2003 |
| HK | 1052364 | A1 | 5/2007 | JP | 03478399 B2 | 12/2003 |
| JP | 48028423 | Y1 | 8/1973 | JP | 2004501058 A | 1/2004 |
| JP | 48028423 | B | 9/1973 | JP | 2004507550 A | 3/2004 |
| JP | 49043924 | Y1 | 12/1974 | JP | 03519410 B2 | 4/2004 |
| JP | 50059324 | U | 6/1975 | JP | 03535172 B2 | 6/2004 |
| JP | 50059326 | U | 6/1975 | JP | 03553952 B2 | 8/2004 |
| JP | 51007649 | B | 3/1976 | JP | 2004534032 A | 11/2004 |
| JP | 52012698 | B | 4/1977 | JP | 2004535929 A | 12/2004 |
| JP | 1013127 | C | 9/1980 | JP | 03621133 B2 | 2/2005 |
| JP | 55047031 | B | 11/1980 | JP | 2005503410 A | 2/2005 |
| JP | 57156454 | U | 10/1982 | JP | 2005505610 A | 2/2005 |
| JP | 57156455 | U | 10/1982 | JP | 2005505611 A | 2/2005 |
| JP | 57179144 | U | 11/1982 | JP | 2005510588 A | 4/2005 |
| JP | 1136333 | C | 2/1983 | JP | 2005510605 A | 4/2005 |
| JP | 58067658 | U | 5/1983 | JP | 2004509942X | 10/2005 |
| JP | 58126892 | U | 8/1983 | JP | 2005533095 A | 11/2005 |
| JP | 1170710 | C | 10/1983 | JP | 2005533096 A | 11/2005 |
| JP | 58159452 | U | 10/1983 | JP | 2005538075 A | 12/2005 |
| JP | 60044295 | A | 3/1985 | JP | 03739404 B2 | 1/2006 |
| JP | 60044295 | B | 10/1985 | JP | 2004534032X | 1/2006 |
| JP | 62294691 | A | 12/1987 | JP | 2004535929X | 1/2006 |
| JP | 63135363 | U | 9/1988 | JP | 2006000451 A | 1/2006 |
| JP | 1013127 | Y2 | 4/1989 | JP | 2006511591 A | 4/2006 |
| JP | 1209830 | A | 8/1989 | JP | 2006519797 A | 8/2006 |
| JP | 1136333 | U | 9/1989 | JP | 2006528616 A | 12/2006 |
| JP | 1050220 | B | 10/1989 | JP | 2007083057 A | 4/2007 |
| JP | 1173751 | U | 12/1989 | JP | 2007509885 A | 4/2007 |
| JP | 1565159 | C | 6/1990 | JP | 2007509886 A | 4/2007 |
| JP | 3001298 | B | 1/1991 | JP | 2007509887 A | 4/2007 |
| JP | 1615749 | C | 8/1991 | JP | 2007519516 A | 7/2007 |
| JP | 3205587 | A | 9/1991 | JP | 2007519663 A | 7/2007 |
| JP | 30699A5 | B | 11/1991 | JP | 2007519664 A | 7/2007 |
| JP | 1627124 | C | 11/1991 | JP | 2007519666 A | 7/2007 |
| JP | 1627146 | C | 11/1991 | JP | 2007519667 A | 7/2007 |
| JP | 3285878 | A | 12/1991 | JP | 2007519670 A | 7/2007 |
| JP | 1642102 | C | 2/1992 | JP | 2007519671 A | 7/2007 |
| JP | 4012248 | Y2 | 3/1992 | JP | 2007519672 A | 7/2007 |
| JP | 4057050 | U | 5/1992 | JP | 2007519673 A | 7/2007 |
| JP | 4166155 | A | 6/1992 | JP | 2007519674 A | 7/2007 |
| JP | 4230254 | A | 8/1992 | JP | 2007519675 A | 7/2007 |
| JP | 4057050 | B | 9/1992 | JP | 2007519677 A | 7/2007 |
| JP | 4060532 | B | 9/1992 | JP | 2007522122 A | 8/2007 |
| JP | 4118676 | U | 10/1992 | JP | 04012248 B2 | 11/2007 |
| JP | 4128141 | U | 11/1992 | JP | 2006515323X | 2/2008 |
| JP | 1729140 | C | 1/1993 | JP | 04057050 B2 | 3/2008 |
| JP | 1811422 | C | 12/1993 | JP | 04060532 B2 | 3/2008 |
| JP | 7025841 | Y2 | 6/1995 | JP | 2006512918X | 3/2008 |
| JP | 7188144 | A | 7/1995 | JP | 008516907 A | 5/2008 |
| JP | 2037346 | C | 3/1996 | JP | 2008515831 A | 5/2008 |
| JP | 8504814 | A | 5/1996 | JP | 04118676 B2 | 7/2008 |
| JP | 8157795 | A | 6/1996 | JP | 04128141 B2 | 7/2008 |
| JP | 2098106 | C | 10/1996 | JP | 04166155 B2 | 10/2008 |
| JP | 02521777 | Y2 | 1/1997 | JP | 04230254 B2 | 2/2009 |
| JP | 02623448 | B2 | 6/1997 | KR | 198802621 Y1 | 7/1988 |
| JP | 9505586 | A | 6/1997 | KR | 198802296 B | 10/1988 |
| JP | 9512013 | A | 12/1997 | KR | 198802296 B1 | 10/1988 |
| JP | 10505101 | A | 5/1998 | KR | 199003458 B1 | 5/1990 |
| JP | 10506911 | A | 7/1998 | KR | 199008166 B1 | 11/1990 |
| JP | 10509954 | A | 9/1998 | KR | 199104132 B1 | 6/1991 |
| JP | 02818503 | B2 | 10/1998 | KR | 199205087 Y1 | 7/1992 |
| JP | 10512879 | A | 12/1998 | KR | 2006132885 A | 12/2006 |
| JP | 11501660 | A | 2/1999 | MX | 2004PA002764 A | 6/2004 |

| | | | |
|---|---|---|---|
| NL | 197700262 A | 7/1977 | |
| NL | 188158 C | 4/1992 | |
| SU | 677650 A | 7/1979 | |
| TW | 387874 B | 4/2000 | |
| TW | 400249 B | 8/2000 | |
| TW | 453983 B | 9/2001 | |
| TW | 453985 B | 9/2001 | |
| TW | 455576 B | 9/2001 | |
| TW | 457244 B | 10/2001 | |
| TW | 458959 B | 10/2001 | |
| TW | 519496 B | 2/2003 | |
| TW | 527340 B | 4/2003 | |
| TW | 576837 B | 2/2004 | |
| TW | 580489 B | 3/2004 | |
| TW | 580490 B | 3/2004 | |
| TW | 584623 B | 4/2004 | |
| TW | 592821 B | 6/2004 | |
| TW | 226345 B | 1/2005 | |
| TW | 233438 B | 6/2005 | |
| TW | 245780 B | 12/2005 | |
| TW | 266650 B | 11/2006 | |
| WO | WO79/00193 A1 | 4/1979 | |
| WO | WO94/14752 A1 | 7/1994 | |
| WO | WO95/14659 A1 | 6/1995 | |
| WO | WO95/28228 A1 | 10/1995 | |
| WO | WO95/29253 A1 | 11/1995 | |
| WO | WO96/11182 A1 | 4/1996 | |
| WO | WO96/16022 A1 | 5/1996 | |
| WO | WO96/22968 A1 | 8/1996 | |
| WO | WO96/29303 A1 | 9/1996 | |
| WO | WO97/03040 A1 | 1/1997 | |
| WO | WO97/12857 A1 | 4/1997 | |
| WO | WO97/24183 A1 | 7/1997 | |
| WO | WO97/36855 A2 | 10/1997 | |
| WO | WO98/11051 A1 | 3/1998 | |
| WO | WO98/27054 A1 | 6/1998 | |
| WO | WO99/06356 | 2/1999 | |
| WO | WO99/06146 A2 | 2/1999 | |
| WO | WO99/06359 A1 | 2/1999 | |
| WO | WO99/13983 A1 | 3/1999 | |
| WO | WO99/64155 A1 | 12/1999 | |
| WO | WO00/01485 A2 | 1/2000 | |
| WO | WO00/37431 A1 | 6/2000 | |
| WO | WO01/21684 A1 | 3/2001 | |
| WO | WO01/36429 A1 | 5/2001 | |
| WO | WO01/68247 A2 | 9/2001 | |
| WO | WO02/11108 A1 | 2/2002 | |
| WO | WO02/13964 A2 | 2/2002 | |
| WO | WO02/18392 A1 | 3/2002 | |
| WO | WO02/26698 A1 | 4/2002 | |
| WO | WO02/30854 | 4/2002 | |
| WO | WO02/053527 A1 | 7/2002 | |
| WO | WO02/092551 A2 | 11/2002 | |
| WO | WO03/011457 A1 | 2/2003 | |
| WO | WO03/018540 A1 | 3/2003 | |
| WO | WO03/024919 A1 | 3/2003 | |
| WO | WO03/031392 A1 | 4/2003 | |
| WO | WO03/033141 A1 | 4/2003 | |
| WO | WO03/033509 A1 | 4/2003 | |
| WO | WO03/046019 A1 | 6/2003 | |
| WO | WO03/046049 A1 | 6/2003 | |
| WO | WO03/068729 A1 | 8/2003 | |
| WO | WO03/076394 A1 | 9/2003 | |
| WO | WO2004/007431 A1 | 1/2004 | |
| WO | WO2004/007432 A1 | 1/2004 | |
| WO | WO2004/007435 A2 | 1/2004 | |
| WO | WO2004/007508 A2 | 1/2004 | |
| WO | WO01/68247 A8 | 6/2004 | |
| WO | WO2004/060855 A1 | 7/2004 | |
| WO | WO2004/064994 A2 | 8/2004 | |
| WO | WO2004/065352 A2 | 8/2004 | |
| WO | WO2004/080924 A2 | 9/2004 | |
| WO | WO2004/080948 A1 | 9/2004 | |
| WO | WO2004/087314 A1 | 10/2004 | |
| WO | WO2005/019160 A1 | 3/2005 | |
| WO | WO2005/042156 A1 | 5/2005 | |
| WO | WO2005/042157 A2 | 5/2005 | |
| WO | WO2005/042547 | 5/2005 | |
| WO | WO2005/042547 A1 | 5/2005 | |
| WO | WO2005/042549 A1 | 5/2005 | |
| WO | WO2005/073167 A1 | 8/2005 | |
| WO | WO2005/073168 A1 | 8/2005 | |
| WO | WO2005/073169 A1 | 8/2005 | |
| WO | WO2005/073170 A1 | 8/2005 | |
| WO | WO2005/073171 A1 | 8/2005 | |
| WO | WO2005/073172 A1 | 8/2005 | |
| WO | WO2005/073173 A1 | 8/2005 | |
| WO | WO2005/073174 A1 | 8/2005 | |
| WO | WO2005/073175 A1 | 8/2005 | |
| WO | WO2005/073176 A1 | 8/2005 | |
| WO | WO2005/073178 A2 | 8/2005 | |
| WO | WO2005/073179 A1 | 8/2005 | |
| WO | WO2005/073241 A1 | 8/2005 | |
| WO | WO2006/040023 A1 | 4/2006 | |
| WO | WO2006/042675 A2 | 4/2006 | |
| WO | WO2005/073166 A3 | 3/2007 | |
| WO | WO2007/051374 A1 | 5/2007 | |
| WO | WO2007/096274 A1 | 8/2007 | |
| WO | WO2007/115936 A2 | 10/2007 | |
| WO | WO2008/008926 A2 | 1/2008 | |
| WO | WO2008/008928 A2 | 1/2008 | |
| WO | WO2008/008929 A2 | 1/2008 | |
| WO | WO2008/008930 A2 | 1/2008 | |
| WO | WO2008/028843 A1 | 3/2008 | |
| WO | WO2008/062058 A1 | 5/2008 | |

OTHER PUBLICATIONS

Homogeneous Nickel-Catalyzed Olefin Hydrocyanation, pp. 201-221—W. C. Seidel and C. A. Tolman, 1985.

Catalytic Hydrocyanation of Olefins by Nickel(0) Phosphite Complexes—Effects of Lewis Acids, Organometallics 1984, 3, 33-38—C. A. Tolman, W. C. Seidel et al.

Science of Synthesis—Houben-Weyl Methods of Molecular Transformations, 2003, Georg Thieme Verlag.

* cited by examiner

HYDROCYANATION OF PENTENENITRILES

CROSS-REFERENCE TO RELATED APPLICATION

This application claims the benefit of the filing date of U.S. Provisional Application No. 61/021,225, filed on Jan. 15, 2008, the entire contents of which are incorporated herein by reference.

FIELD OF THE INVENTION

The present process is directed to an integrated process for the hydrocyanation of ethylenically unsaturated nitriles having five carbon atoms to produce adiponitrile (ADN) and other dinitriles and for the refining of the reaction product mixture. More particularly, this invention relates to a continuous process for the hydrocyanation of 3-pentenenitriles (3PN) and/or 4-pentenenitrile (4PN), and optionally 2-pentenenitriles (2PN), using a catalyst composition comprising a zero-valent nickel and at least one bidentate phosphorus-containing ligand in the presence of at least one Lewis acid promoter, and refining of the reaction product mixture.

BACKGROUND OF THE INVENTION

Hydrocyanation catalyst systems, particularly pertaining to the hydrocyanation of ethylenically unsaturated compounds, have been described. For example, systems useful for the hydrocyanation of 1,3-butadiene (BD) to form pentenenitrile (PN) isomers and in the subsequent hydrocyanation of pentenenitriles to form adiponitrile (ADN) are known in the commercially important nylon synthesis field. ADN is of particular interest because it is a commercially versatile and important intermediate in the industrial production of nylon polyamides useful in forming films, fibers and molded articles.

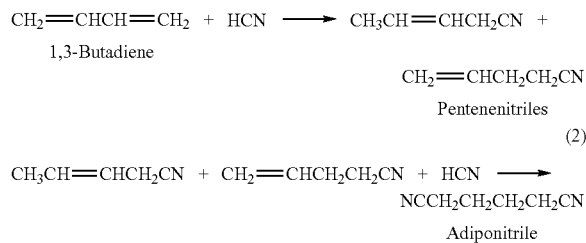

The hydrocyanation of ethylenically unsaturated compounds using transition metal complexes with monodentate phosphite ligands is recited in the prior art. See, for example, U.S. Pat. Nos. 3,496,215; 3,631,191; 3,655,723; and 3,766,237, and Tolman et. al., *Advances in Catalysis*, 1985, 33, 1. Improvements in the zero-valent nickel catalyzed hydrocyanation of ethylenically unsaturated compounds with the use of certain multidentate phosphite ligands are also disclosed. Such improvements are described, for example, in U.S. Pat. Nos. 5,821,378; 5,981,772; 6,020,516; and 6,284,865.

The hydrocyanation of activated ethylenically unsaturated compounds, such as with conjugated ethylenically unsaturated compounds (e.g., BD and styrene), and strained ethylenically unsaturated compounds (e.g., norbornene) proceed at useful rates without the use of a Lewis acid promoter. However, hydrocyanation of unactivated, ethylenically unsaturated compounds, such as 1-octene and 3PN, requires the use of a Lewis acid promoter to obtain industrially useful rates and yields for the production of linear nitriles, such as n-octyl cyanide and ADN, respectively.

The use of a promoter in the hydrocyanation reaction is disclosed, for example, in U.S. Pat. No. 3,496,217. This patent discloses an improvement in hydrocyanation using a promoter selected from a large number of metal cation compounds as nickel catalyst promoters with a wide variety of counterions. U.S. Pat No. 3,496,218 discloses a nickel hydrocyanation catalyst promoted with various boron-containing compounds, including triphenylboron and alkali metal borohydrides. U.S. Pat No. 4,774,353 discloses a process for the preparation of dinitriles, including ADN, from unsaturated nitriles, including pentenenitriles, in the presence of a zero-valent nickel catalyst and a triorganotin promoter. Moreover, U.S. Pat. No. 4,874,884 discloses a process for producing ADN by the zero-valent nickel catalyzed hydrocyanation of pentenenitriles in the presence of a synergistic combination of promoters selected in accordance with the desired reaction kinetics of the ADN synthesis. Furthermore, the use of Lewis acids to promote the hydrocyanation of pentenenitriles to produce ADN using zero-valent nickel catalysts with multidentate phosphite ligands is also disclosed. See, for example, U.S. Pat. Nos. 5,512,696; 5,723,641; 5,959,135; 6,127,567; and 6,646,148.

It is reported in the prior art that, concomitant with the hydrocyanation of 3PN and 4PN to produce ADN, some isomerization of 3PN to cis- and trans-2PN can occur. However, in the process of hydrocyanating 3PN and 4PN using nickel catalysts derived from monodentate phosphite ligands, such as $Ni[P(OC_6H_5)_3]_4$, U.S. Pat. No. 3,564,040 states that the presence of 2PN, even in low concentrations, is detrimental to catalyst efficiency and the production of 2PN is undesirable since they constitute a yield loss as well as a poison for the catalyst.

In order to address this issue, U.S. Pat. No. 3,564,040 describes a method to maintain the steady-state concentration of 2PN below 5 mole percent as based on the nitriles present in the reaction mixture. Because trans-2PN is difficult to separate from a mixture of 3PN and 4PN by distillation due to their close relative volatilities, the disclosed method involves the catalytic isomerization of trans-2PN to cis-2PN followed by fractional distillation of the mixture of pentenenitrile isomers to remove the more volatile cis-2PN isomer. The catalyst systems used to isomerize trans-2PN to cis-2PN are those that also serve to hydrocyanate pentenenitriles to ADN, in particular, nickel catalysts derived from monodentate phosphite ligands as described in U.S. Pat. Nos. 3,496,217 and 3,496,218.

Alternative catalyst systems for the isomerization of trans-2PN to cis-2PN are disclosed in U.S. Pat. No. 3,852,325 and 3,852,327. The primary advantage of the catalyst systems described therein is in avoiding appreciable carbon-carbon double bond migration in the pentenenitrile isomers, which allows for the isomerization of trans-2PN to cis-2PN without substantial further isomerization of the 3PN to 2PN. The catalysts described in U.S Pat. No. 3,852,325 are compounds of the general formula $R_3C$—X, such as triphenylmethyl bromide, wherein R is an aryl radical having up to 18 carbon atoms and —X is of the group consisting of —H, —Cl, —Br, —I, —SH, —B$(C_6H_5)_4$, —PF$_6$, —AsF$_6$, —SbF$_6$ and —BF$_4$, while the catalyst systems described in U.S. Pat. No. 3,852,327 are Lewis acid/Lewis base compositions, such as combinations of zinc chloride with triphenylphosphine.

A different method of removing the 2PN from mixtures of pentenenitrile isomers containing 3PN and 4PN is disclosed in U.S. Pat. No. 3,865,865. The 2PN and/or 2-methyl-2-butenenitriles (2M2BN) can be selectively separated from a mixture of pentenenitrile isomers containing 3PN and 4PN by contacting the mixture of nitriles with an aqueous solution of a treating agent comprising sulfite and bisulfite ions and ammonium or alkali metal cations to produce an aqueous phase containing the bisulfite adduct of the 2PN and/or 2M2BN and an organic phase containing the 3PN and 4PN, substantially free of 2PN and 2M2BN. The recovered organic phase can provide a feed material of pentenenitriles for further hydrocyanation to produce ADN with greatly reduced amounts of the undesired by-product 2PN that is detrimental to catalyst efficiency.

U.S. Pat No. 6,127,567 discloses nickel catalyst compositions derived from bidentate phosphite ligands and processes for the hydrocyanation of monoethylenically unsaturated compounds which are more rapid, selective, efficient, and stable than prior processes using nickel catalysts derived from monodentate phosphites. U.S. Pat. No. 5,688,986 discloses that at least one member of this class of catalysts is capable of hydrocyanating olefins conjugated to nitriles, for example 2PN. The present invention provides novel processes for the hydrocyanation of pentenenitriles to produce dinitriles, in particular ADN, using certain catalyst compositions described in U.S. Pat. No. 6,127,567 as well as other catalyst compositions. The present invention also provides novel processes for refining the reaction product mixture to obtain, for example, a stream comprising adiponitrile, a stream comprising a catalyst composition, and a stream comprising ethylenically unsaturated nitriles. Such processes can overcome the detrimental effect of 2PN on catalyst efficiency and can greatly reduce or eliminate yield losses to 2PN in the pentenenitrile hydrocyanation reaction. Such processes can also provide lower investment and operating costs for an adiponitrile manufacturing process by (1) avoiding the need for separation of unreacted ethylenically unsaturated nitriles from the reaction product mixture prior to liquid-liquid extraction, (2) avoiding a dedicated distillation column for cis-2PN removal from ethylenically unsaturated nitriles, and (3) enabling a simple and economical method of purging compounds that cannot be converted to ADN from the manufacturing process.

SUMMARY OF THE INVENTION

In a first aspect, the present invention provides a hydrocyanation process to produce adiponitrile and other dinitriles having six carbon atoms, the process comprising:
  a) forming a reaction mixture in the presence of at least one Lewis acid, said reaction mixture comprising ethylenically unsaturated nitriles having five carbon atoms, hydrogen cyanide, and at least one catalyst composition, by continuously feeding the ethylenically unsaturated nitriles, the hydrogen cyanide, and the catalyst composition; wherein
    the catalyst composition comprises a zero-valent nickel and at least one bidentate phosphorus-containing ligand;
    the bidentate phosphorus-containing ligand is selected from the group consisting of a phosphite, a phosphonite, a phosphinite, a phosphine, and
    a mixed phosphorus-containing ligand or a combination of such members; and the bidentate phosphorus-containing ligand gives acceptable results according to at least one protocol of the 2-Pentenenitrile Hydrocyanation Test Method;
  b) controlling X and Z, wherein
    X is the overall feed molar ratio of 2-pentenenitriles to all unsaturated nitriles; and
    Z is the overall feed molar ratio of hydrogen cyanide to all unsaturated nitriles;
  by selecting
    a value for X in the range of about 0.001 to about 0.5; and
    a value for Z in the range of about 0.5 to about 0.99; such that the value of quotient Q, wherein $$Q = \frac{X}{\left[\dfrac{(\text{moles } 3PN + 4PN \text{ in the feed})/}{(\text{moles all unsaturated nitriles in the feed})}\right] - Z}$$

is in the range from about 0.2 to about 10, wherein 3PN is 3-pentenenitriles and 4PN is 4-pentenenitrile;
  c) withdrawing a reaction product mixture comprising adiponitrile, 2-methylglutaronitrile, ethylenically unsaturated nitrites, the catalyst composition, and catalyst composition degradation products; and
    wherein the ratio of the concentration of 2-pentenenitriles to the concentration of 3-pentenenitriles in the reaction mixture is in the range from about 0.2/1 to about 10/1;
  d) extracting at least a portion of the reaction product mixture with an extraction agent selected from the group consisting of aliphatic hydrocarbons, cycloaliphatic hydrocarbons, and mixtures thereof to obtain an extract phase comprising the extraction agent and the catalyst composition and a raffinate phase comprising adiponitrile, 2-methylglutaronitrile, ethylenically unsaturated nitrites, catalyst composition degradation products, and the extraction agent; and
  e) distilling the extract phase to obtain a first stream comprising the extraction agent and a second stream comprising the catalyst composition.

Another aspect of the present invention is the process further comprising distilling the raffinate phase to obtain a third stream comprising the extraction agent and a fourth stream comprising adiponitrile, 2-methylglutaronitrile, ethylenically unsaturated nitrites, and catalyst composition degradation products.

Another aspect of the present invention is the process further comprising distilling the fourth stream to obtain a fifth stream comprising ethylenically unsaturated nitrites and a sixth stream comprising adiponitrile, 2-methylglutaronitrile, and catalyst composition degradation products.

Another aspect of the present invention is the process further comprising distilling the sixth stream to obtain a seventh stream comprising adiponitrile and 2-methylglutaronitrile and an eighth stream comprising catalyst degradation products.

Another aspect of the present invention is the process further comprising distilling the seventh stream to obtain a ninth stream comprising 2-methylglutaronitrile and a tenth stream comprising adiponitrile.

Another aspect of the present invention is the process further comprising returning at least a portion of the first stream, at least a portion of the third stream, or combinations thereof to the extraction.

Another aspect of the present invention is the process wherein at least a portion of the fifth stream is returned to the reaction mixture.

Another aspect of the present invention is the process wherein at least a portion of the second stream is combined with at least a portion of the fifth stream, and optionally returned to the reaction mixture.

Another aspect of the present invention is the process wherein the fifth stream further comprises compounds which cannot be converted to adiponitrile, and wherein at least a portion of the fifth stream is withdrawn to purge at least a portion of the compounds which cannot be converted to adiponitrile.

Another aspect of the present invention is the process wherein in the fifth stream the total content of compounds which cannot be converted to adiponitrile is greater than about 10 percent by weight.

Another aspect of the present invention is the process further comprising distilling at least a portion of the fifth stream to obtain an eleventh stream comprising cis-2-pentenenitrile and an twelfth stream comprising 3-pentenenitrile.

Another aspect of the present invention is the process wherein at least a portion of the twelfth stream is returned to the reaction mixture.

Another aspect of the present invention is the process further comprising contacting at least a portion of the second stream with nickel chloride and a reducing metal which is more electropositive than nickel in the presence of a nitrile solvent to obtain a fifteenth stream, and optionally returning at least a portion of the fifteenth stream to the reaction mixture.

Another aspect of the present invention is the process further comprising contacting with ammonia at least one stream selected from the group consisting of the reaction product mixture, the raffinate phase, the fourth stream, the sixth stream, and combinations thereof, wherein the reaction product mixture, the raffinate phase, the fourth stream, the sixth stream, and combinations thereof further comprise at least one Lewis acid.

Another aspect of the present invention is the process wherein distilling the extract phase is done in two stages with each distillation column base temperature being about 150° C. or less.

Another aspect of the present invention is the process wherein distilling the extract phase is done in two stages with each distillation column base temperature being about 120° C. or less.

Another aspect of the present invention is the process wherein the catalyst composition further comprises at least one monodentate phosphite ligand.

Another aspect of the present invention is the process wherein the bidentate phosphorus-containing ligand is a phosphite ligand selected from a member of the group represented by Formula XXXIII and Formula XXXIV:

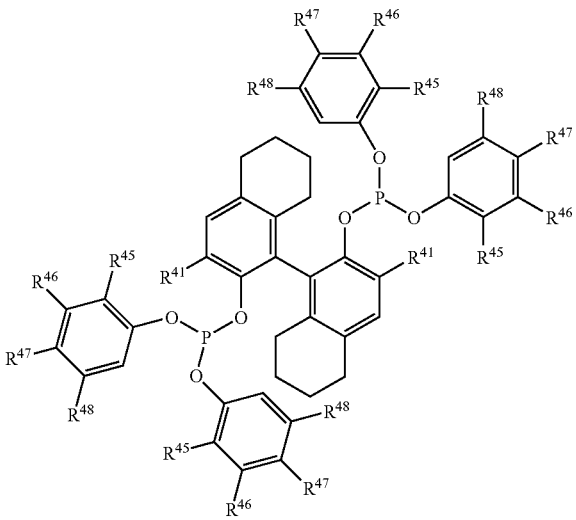

Formula XXXIV wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms.

Another aspect of the present invention is the process further comprising introducing a stream comprising a crude bidentate phosphite ligand mixture comprising a phosphite ligand selected from a member of the group represented by Formula XXXIII and Formula XXXIV:

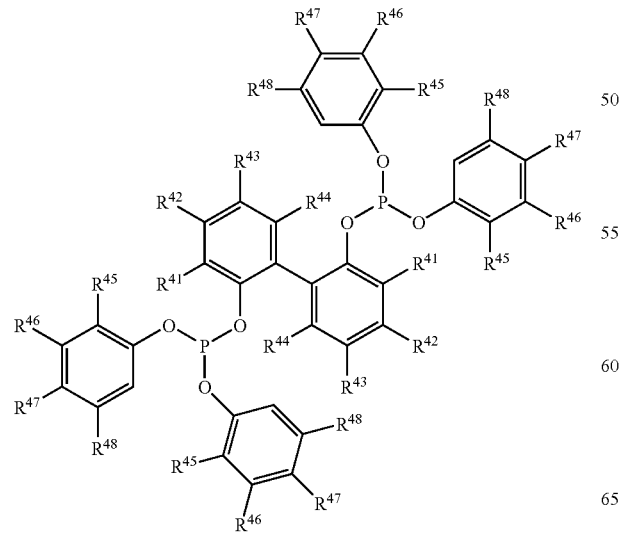

Formula XXXIII

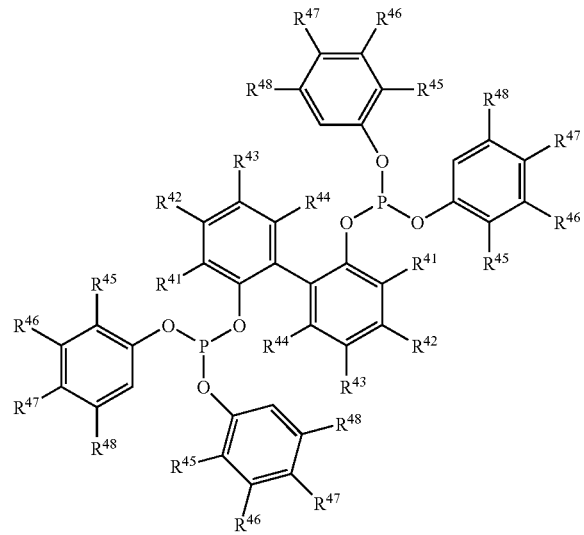

Formula XXXIII

-continued

Formula XXXIV

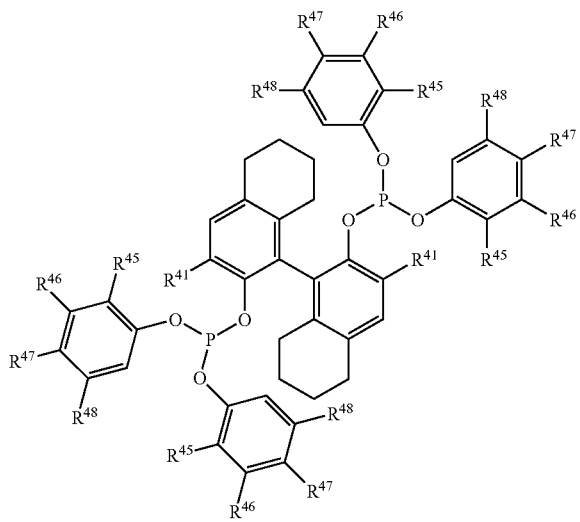

wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms, to the extraction of the reaction product mixture.

Another aspect of the present invention is the process wherein the at least one Lewis acid comprises zinc chloride and the extraction agent comprises cyclohexane.

Another aspect of the present invention is the process wherein at least a portion of the second stream is introduced into a 3-pentenenitrile manufacturing process comprising 1,3-butadiene hydrocyanation, 2-methyl-3-butenenitrile isomerization, or a combination thereof.

DETAILED DESCRIPTION OF THE DRAWINGS

FIG. 1 schematically illustrates one embodiment of the processes of the invention.

Figure 2:
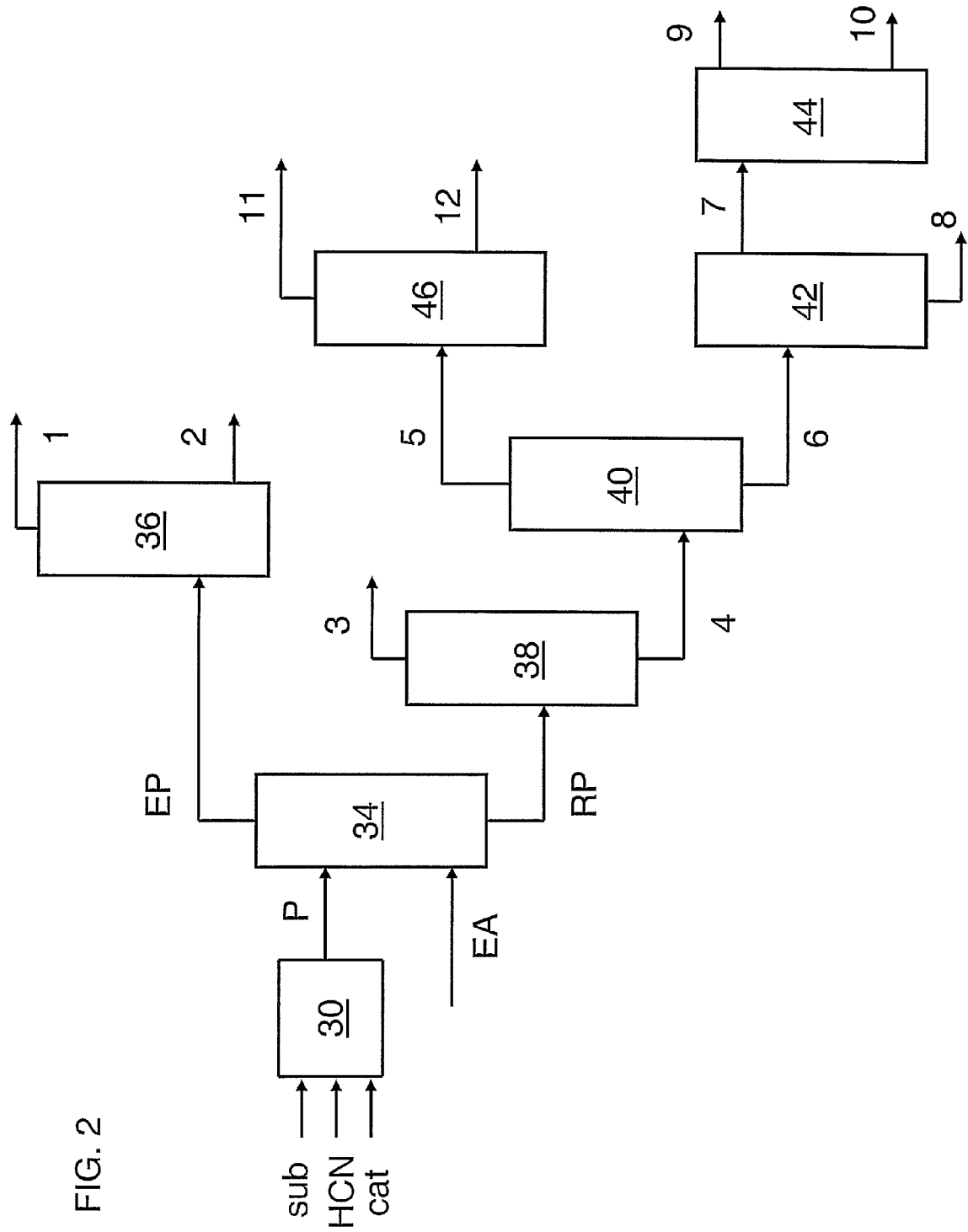

FIG. 2 schematically illustrates another embodiment of the processes of the invention.

Figure 3:
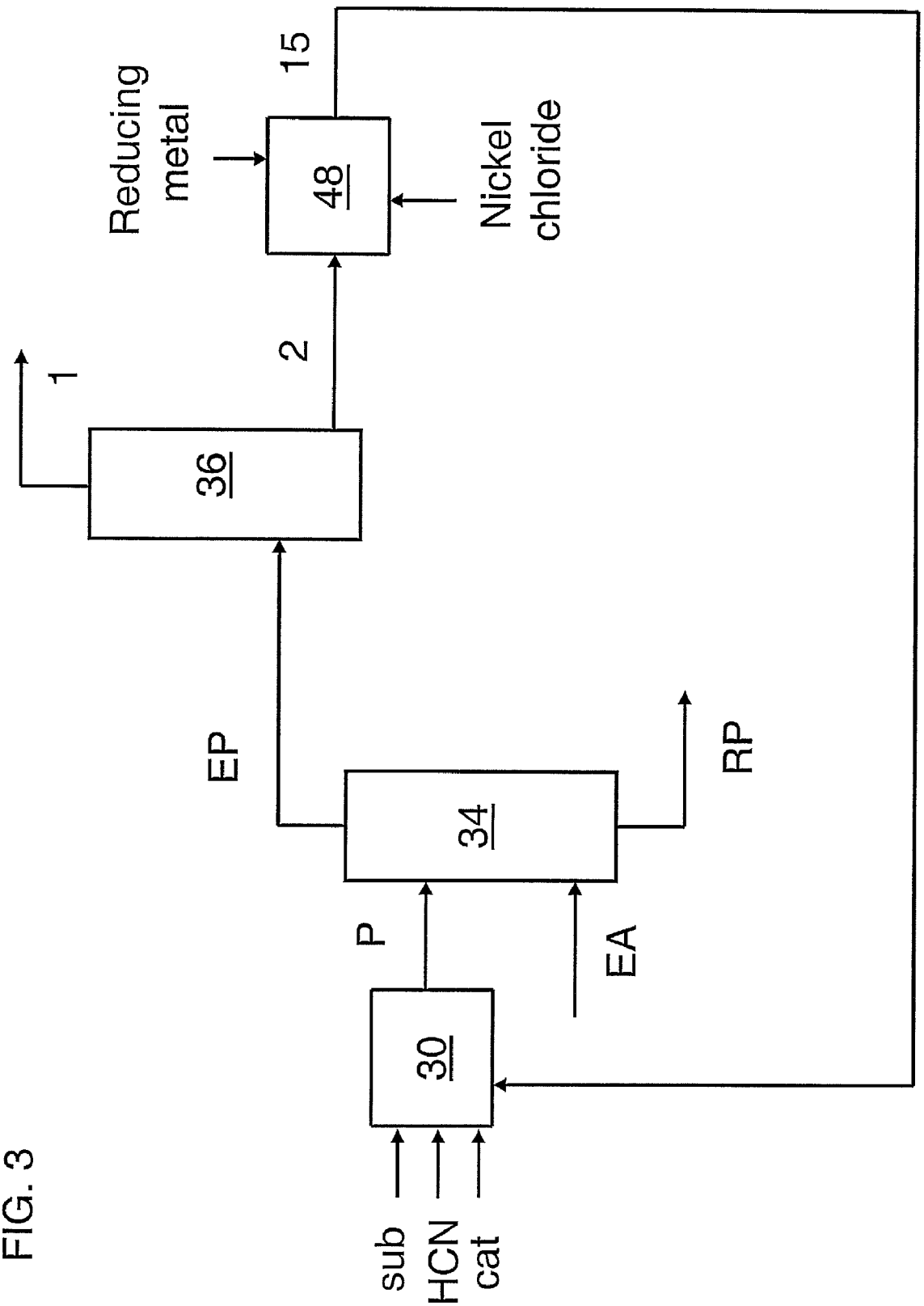

FIG. 3 schematically illustrates one embodiment of the processes of the invention, in which the second stream is contacted with nickel chloride and a reducing metal which is more electropositive than nickel to obtain a fifteenth stream, which is returned to the reaction mixture.

Figure 4:
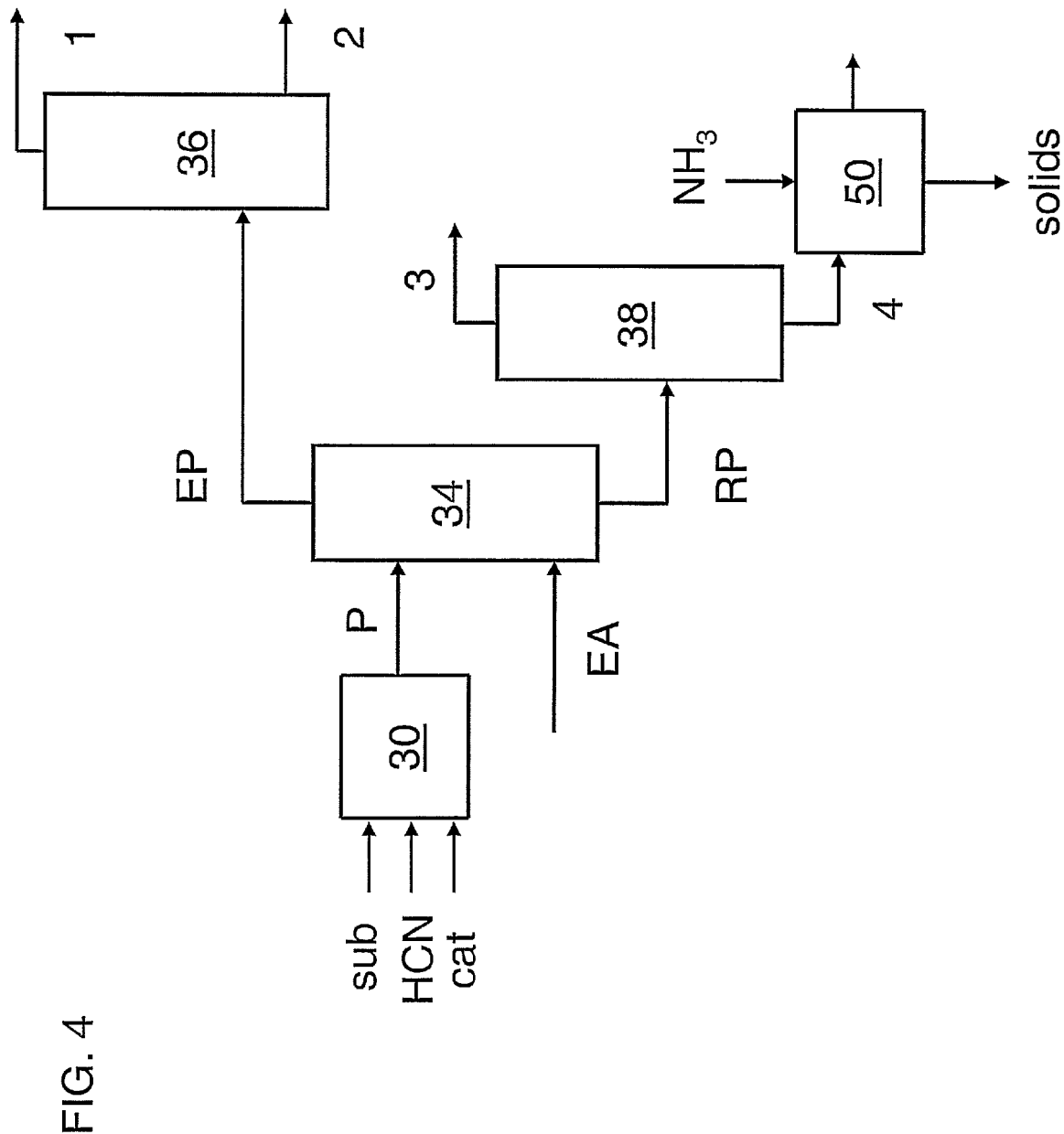

FIG. 4 schematically illustrates one embodiment of the processes of the invention, in which the fourth stream is contacted with ammonia.

DETAILED DESCRIPTION OF THE INVENTION

As used herein, the terms "2PN", "2-pentenenitrile", and "2-pentenenitriles" include both cis-2-pentenenitrile (cis-2PN) and trans-2-pentenenitrile (trans-2PN), unless otherwise specified. Similarly, the terms "3PN", "3-pentenenitrile," and "3-pentenenitriles" include both cis-3-pentenenitrile (cis-3PN) and trans-3-pentenenitrile (trans-3PN), unless otherwise specified. The term "4PN" refers to 4-pentenenitrile. The term "2M3BN" refers to 2-methyl-3-butenenitrile. The term "2M2BN" refers to 2-methyl-2-butenenitrile and includes both (Z)-2-methyl-2-butenenitrile [(Z)-2M2BN] and (E)-2-methyl-2-butenenitrile [(E)-2M2BN], unless otherwise specified.

As used herein, the terms "ethylenically unsaturated nitriles having five carbon atoms" and "ethylenically unsaturated nitriles" mean pentenenitriles and methylbutenenitriles and include 2PN, 3PN, 4PN, 2M3BN, and 2M2BN, separately or in combination. As used herein, the term "unsaturated nitriles" also means pentenenitriles and methylbutenenitriles.

As used herein, the term "ADN" refers to adiponitrile. The term "MGN" refers to 2-methylglutaronitrile.

Distillation "base temperature" refers to the temperature of the bottoms material within a distillation apparatus, for example, being circulated through a heat-exchanger.

The present invention provides a process for the hydrocyanation of ethylenically unsaturated nitriles having five carbon atoms to produce adiponitrile and other dinitriles having six carbon atoms and for the refining of the reaction product mixture. A reaction mixture comprising ethylenically unsaturated nitriles having five carbon atoms, hydrogen cyanide, and at least one catalyst composition is formed by continuously feeding these materials in the presence of at least one Lewis acid. A reaction product mixture comprising ADN, MGN, ethylenically unsaturated nitriles, the catalyst composition, and catalyst composition degradation products, wherein the ratio of the concentration of 2PN to the concentration of 3PN in the reaction mixture is in the range from about 0.2/1 to about 10/1, is withdrawn from the reaction zone.

In the case where the reaction product mixture is suitable for catalyst composition recovery via liquid-liquid extraction through contact with an extraction agent, that is, where phase separation occurs in extraction, at least a portion of the reaction product mixture is extracted to obtain an extract phase and a raffinate phase. The extract and raffinate phases are then refined in a series of distillations, to provide, for example, refined ADN, ethylenically unsaturated nitriles, the catalyst composition, catalyst composition degradation products, and the extraction agent.

For example, the extract phase, which comprises the extraction agent and the catalyst composition, is distilled to obtain a first stream comprising the extraction agent and a second stream comprising the catalyst composition. Distilling the extract phase can be done, for example, in two stages with each distillation column base temperature being about 150° C. or less, for example about 120° C. or less.

Optionally, in order to increase the concentration of nickel in the catalyst composition to a desired level, at least a portion of the second stream is contacted with nickel chloride in the presence of a reducing metal which is more electropositive than nickel to obtain a fifteenth stream. Optionally, at least a portion of the fifteenth stream is returned to the reaction mixture as at least a portion of the catalyst composition feed.

Optionally, at least a portion of the second stream is introduced into a 3PN manufacturing process comprising 1,3-butadiene hydrocyanation, 2-methyl-3-butenenitrile isomerization, or a combination thereof.

The raffinate phase is distilled to obtain a third stream comprising the extraction agent and a fourth stream comprising ADN, MGN, ethylenically unsaturated nitriles, and catalyst composition degradation products. The fourth stream is distilled to obtain a fifth stream comprising ethylenically unsaturated nitriles and a sixth stream comprising ADN, MGN, and catalyst composition degradation products. The sixth stream is distilled to obtain a seventh stream comprising ADN and MGN and an eighth stream comprising catalyst composition degradation products. The seventh stream is distilled to obtain a ninth stream comprising MGN and a tenth stream comprising ADN.

Optionally, at least a portion of the first stream and at least a portion of the third stream, or combinations thereof, can be returned to the extraction step.

Optionally, at least a portion of the fifth stream is returned to the reaction mixture. Optionally, at least a portion of the fifth stream can be combined with the second stream, and this combined stream can be returned to the reaction mixture. Optionally, at least a portion of the fifth stream is combined with the second stream prior to or subsequent to the second stream being contacted with nickel chloride in the presence of a reducing metal which is more electropositive than nickel to obtain the fifteenth stream.

The fifth stream can further comprise compounds which cannot be converted to ADN, and at least a portion of the fifth stream can be withdrawn to purge at least a portion of the compounds which cannot be converted to ADN from the manufacturing process. The total content in the fifth stream of compounds which cannot be converted to ADN can be, for example, greater than about 10 percent by weight.

Optionally, the fifth stream is distilled to obtain an eleventh stream comprising cis-2PN and an twelfth stream comprising 3PN. At least a portion of the twelfth stream can be returned to the reaction mixture. At least a portion of the eleventh stream can be withdrawn and purged from the process to remove compounds which cannot be converted to ADN.

In one embodiment of the process, the at least one Lewis acid comprises zinc chloride and the extraction agent comprises cyclohexane.

In the case where the reaction product mixture comprising ADN, MGN, ethylenically unsaturated nitriles, the catalyst composition, and catalyst composition degradation products, wherein the ratio of the concentration of 2PN to the concentration of 3PN in the reaction mixture is in the range from about 0.2/1 to about 10/1, is not suitable for catalyst composition recovery via liquid-liquid extraction through contact with an extraction agent, the content of ethylenically unsaturated nitriles in the reaction product mixture should be adjusted in order for phase separation to occur in extraction. In this case, for example, the reaction product mixture can be distilled before extraction to obtain a thirteenth stream comprising ethylenically unsaturated nitriles and a fourteenth stream depleted in ethylenically unsaturated nitriles and comprising the catalyst composition, catalyst degradation products, ADN, MGN, and ethylenically unsaturated nitriles. The fourteenth stream is extracted to obtain the extract phase and the raffinate phase, and these phases are subsequently refined as described above, for example in a series of distillations, to obtain, for example, refined ADN, the catalyst composition, ethylenically unsaturated nitriles, and the extraction agent. Optionally, at least a portion of the thirteenth stream can be returned to the reaction mixture as a portion of the ethylenically unsaturated nitrile feed. In one embodiment of the process, the at least one Lewis acid comprises zinc chloride and the extraction agent comprises cyclohexane.

Irrespective of whether or not the reaction product mixture has characteristics suitable for phase separation in extraction, streams containing the Lewis acid can be contacted with ammonia to separate at least partially the Lewis acid, for example zinc chloride, from the other components of the stream. Streams containing the Lewis acid include, for example, the reaction product mixture, the raffinate phase, the fourth stream, the sixth stream, the fourteenth stream, and combinations thereof.

By utilizing appropriate catalyst compositions in the hydrocyanation reaction of ethylenically unsaturated nitriles having five carbon atoms to produce ADN and other dinitriles having six carbon atoms, the yield losses due to the concurrent production of 2PN from 3PN can be greatly reduced or eliminated through the control of the ratio of the concentration of 2PN to the concentration of 3PN, in the reaction mixture, from about 0.2/1 to about 10/1.

Control of the ratio of the concentration of 2PN to the concentration of 3PN in the reaction mixture can be achieved by both controlling X, the overall feed molar ratio of 2PN to all unsaturated nitrites, and controlling Z, the overall feed molar ratio of hydrogen cyanide (HCN) to all unsaturated nitriles. X and Z can be controlled by selecting a value for X in the range from about 0.001 to about 0.5 and by selecting a value for Z in the range from about 0.5 to about 0.99, such that the value of quotient Q, wherein $$Q = \frac{X}{\left[\frac{(\text{moles } 3PN + 4PN \text{ in the feed})/}{(\text{moles all unsaturated nitriles in the feed})}\right] - Z}$$

is in the range from about 0.2 to about 10, wherein 3PN is 3-pentenenitriles and 4PN is 4-pentenenitrile. When the ratio of the concentration of 2PN to the concentration of 3PN in the reaction mixture is controlled from about 1/1 to about 5/1, for example, X and Z can be controlled by selecting a value for X in the range from about 0.01 to about 0.25 and by selecting a value for Z in the range from about 0.70 to about 0.99, such that the value of the quotient Q is in the range from about 1 to about 5.

Advantageously, a zero-valent nickel catalyst system and far less process equipment can be utilized for conversion of 2PN to the valuable products 3PN, 4PN, and ADN. Utilizing an appropriate catalyst composition, which can be expected to be more rapid, selective, efficient, and stable than prior catalyst composition derived from monodentate phosphite ligands used in the hydrocyanation of ethylenically unsaturated compounds, can overcome the prior art limitations of maintaining the steady-state concentrations of 2PN below 5 mole percent (based on the nitriles present in the reaction mixture). With appropriate catalyst compositions, 2PN can be converted to useful products, for example 3PN and 4PN, and is not a yield loss. Also, as control of the overall feed molar ratio of 2PN to all unsaturated nitriles can be achieved by direct recycle of the ethylenically unsaturated nitriles comprising 2PN from the reaction product mixture within the process or by addition of 2PN produced in an independent process, a distillation column dedicated to removal of cis-2PN in order to enable reduction of 2PN in the hydrocyanation reaction is not required. This can result in savings in both investment and operating costs, as well as process simplification.

The ethylenically unsaturated nitriles having five carbon atoms can be prepared by the reaction of hydrogen cyanide (HCN) with 1,3-butadiene (BD).

(3)

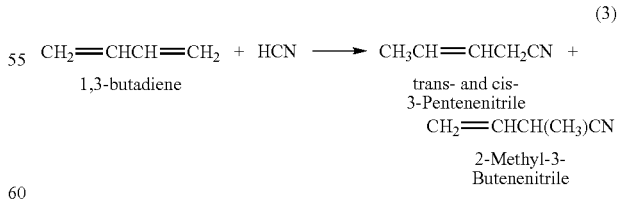

Using transition metal complexes with monodentate phosphites (for example, U.S. Pat. Nos. 3,496,215; 3,631,191; 3,655,723; and 3,766,237) and zero-valent nickel catalysts with multidentate phosphite ligands (for example, U.S. Pat. Nos. 5,821,378; 5,981,772; 6,020,516; and 6,284,865), the predominant linear pentenenitrile product formed by the hydrocyanation of BD is trans-3PN. As described in the prior art, the branched BD hydrocyanation product, 2-methyl-3-butenenitrile (2M3BN), can be isomerized to predominantly trans-3PN using the same catalyst compositions employed for the hydrocyanation of BD. See, for example, U.S. Pat. Nos. 3,536,748 and 3,676,481. The predominant trans-3PN product from the hydrocyanation of BD and isomerization of 2M3BN can also contain smaller quantities of 4PN, cis-3PN, 2PN, and 2M2BN isomers.

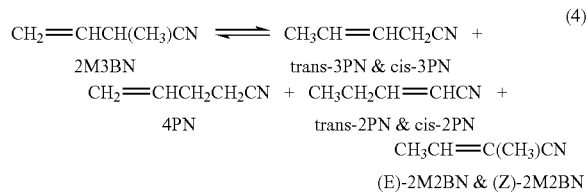

The 2PN useful in the present invention can be made in larger quantities during the hydrocyanation of 3PN and/or 4PN to form ADN, among other dinitriles, from the concurrent isomerization of 3PN to 2PN, as described in the prior art. Separation of the cis-2PN isomer by the fractional distillation of mixtures of pentenenitrile isomers, as disclosed in the art, can provide a source of isolated 2PN to be used with the present invention. See, for example, U.S. Pat. No. 3,852,327. Alternatively, the cis-2PN need not be isolated from mixtures of pentenenitrile isomers. For example, 2PN mixtures comprising 2PN, 3PN, and 4PN may be separated by vacuum distillation from the pentenenitrile hydrocyanation reaction product comprising unreacted pentenenitriles, ADN and other six carbon dinitriles, catalyst, and promoter, by methods known in the art. The 2PN mixture, as a distillation column sidestream or overhead make, may then be recycled directly to the pentenenitrile hydrocyanation process. Alternatively, the hydrocyanation reaction process of the present invention may be operated at sufficiently high conversion of pentenenitriles to enable the hydrocyanation reaction product, comprising unreacted ethylenically unsaturated nitriles, ADN and other six carbon dinitriles, catalyst composition, and Lewis acid promoter, to be fed directly to a liquid-liquid extraction process as described, for example, in U.S. Pat. No. 6,936,171, wherein the pentenenitrile to dinitrile molar ratio is from about 0.65 to about 2.5. Pentenenitrile mixtures comprising 2PN, 3PN, and 4PN, can be recovered, for example, by distillation of the extract, raffinate, or extract and raffinate phases of a liquid-liquid extraction process may also be recycled to the hydrocyanation process of the present invention, for example as a portion of the ethylenically unsaturated nitrile feed.

The hydrocyanation process to produce ADN and other dinitriles having six carbon atoms is performed in the presence of at least one Lewis acid and using a catalyst composition comprising a zero-valent nickel and at least one multidentate phosphorus-containing (P-containing) ligand, wherein the P-containing ligand is selected from the group consisting of a phosphite, a phosphonite, a phosphinite, a phosphine, and a mixed phosphorus-containing ligand or a combination of such members. As used herein, the term "mixed phosphorus-containing ligand" means a multidentate phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

The catalyst composition may also further comprise at least one Lewis acid promoter.

The catalyst composition may comprise at least one monodentate P-containing ligand selected from the group consisting of a phosphite, a phosphonite, a phosphinite, and a phosphine or a combination of such members, provided that the monodentate P-containing ligand does not detract from the beneficial aspects of the invention. The monodentate P-containing ligand may be present as an impurity from the synthesis of the P-containing ligand, or the monodentate P-containing ligand may be added as a single or additional component of the catalyst. The monodentate P-containing ligand may be a mixture of P-containing ligands.

As used herein, the term "catalyst composition" includes within its meaning a catalyst precursor composition, indicating that that the zero-valent nickel at some point becomes bound to at least one P-containing ligand, and further in all likelihood, additional reactions occur during hydrocyanation, such as, for example, complexing of the initial catalyst composition to an ethylenically unsaturated compound. As used herein, the term "catalyst composition" also includes within its meaning recycled catalyst, that is, a catalyst composition comprising a zero-valent nickel and at least one P-containing ligand which, having been used in the process of the invention, is returned or may be returned to the process and used again.

During hydrocyanation and the subsequent refining processes, partial degradation of the catalyst composition may occur, as disclosed, for example, in U.S. Pat. Nos. 3,773,809, which is incorporated herein by reference. Catalyst composition degradation products are disclosed, for example, in U.S. Pat. No. 3,773,809, which is incorporated herein by reference. The resulting degradation products can include oxidized nickel compounds such as nickel(II) cyanide-containing species. Additional degradation products can include, for example, hydrolyzed phosphorus compounds which are derived from reaction of the P-containing ligand with traces of water which may be present in the feedstocks, for example in the HCN. Catalyst composition degradation products can also include oxidized phosphorus compounds having phosphorus atoms in the oxidation state (V) which are derived from reaction of the P-containing ligand with oxygen or with peroxides. Oxygen or peroxides can be present in the feedstocks, for example in the ethylenically unsaturated nitriles, for example as a result of leakage in the equipment or by dissolution of oxygen in the ethylenically unsaturated nitriles, for example during storage, with subsequent formation of peroxides. Additional catalyst composition degradation products can include monodentate phosphorus-containing compounds derived, for example, from thermally induced, or proton- or base-catalyzed, rearrangement of the radicals on the phosphorus atoms of the P-containing ligands. As used herein, the term "catalyst composition degradation products" is intended to include the types of degradation products described herein, and comprises at least one compound selected from the group consisting of an oxidized nickel compound, a hydrolyzed P-containing ligand compound, an oxidized P-containing ligand compound, and combinations thereof.

The term "hydrocarbyl" is well known in the art and designates a hydrocarbon molecule from which at least one hydrogen atom has been removed. Such molecules can contain single, double, or triple bonds.

The term "aryl" is well-known in the art and designates an aromatic hydrocarbon molecule from which at least one hydrogen atom has been removed. Examples of suitable aryl groups include, for example, those containing 6 to 10 carbon atoms, which can be unsubstituted or singly or multiply substituted. Suitable substituents include, for example, $C_1$-$C_4$ hydrocarbyl, or halogen such as fluorine, chlorine, or bromine, or halogenated hydrocarbyl such as trifluoromethyl, or aryl such as phenyl.

The P-containing ligands of the Ni(0) complexes and the free P-containing ligands may be monodentate or multidentate, for example bidentate or tridentate. The term "bidentate" is well known in the art and means both phosphorus atoms of the ligand are bonded to a single metal atom. The term "tridentate" means the three phosphorus atoms on the ligand are bonded to a single metal atom. The P-containing ligand may be a single compound or a mixture of compounds. The P-containing ligand may be selected from the group consisting of a phosphite, a phosphonite, a phosphinite, a phosphine, and a mixed P-containing ligand or a combination of such members. A multidentate P-containing ligand may be represented by Formula I

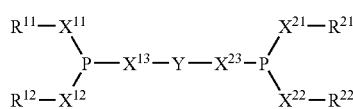

Formula I wherein $X^{11}$, $X^{12}$, $X^{13}$, $X^{21}$, $X^{22}$, $X^{23}$ independently represent oxygen or a single bond, $R^{11}$, $R^{12}$ independently represent identical or different, single or bridged organic radicals, $R^{21}$, $R^{22}$ independently represent identical or different, single or bridged organic radicals, and Y represents a bridging group.

It is to be understood that Formula I may represent a single compound or a mixture of different compounds having the indicated formula.

In one embodiment, all of the groups $X^{11}$, $X^{12}$, $X^{13}$, $X^{21}$, $X^{22}$, $X^{23}$ may represent oxygen. In such a case, the bridging group Y is joined to phosphite groups. In such a case, the multidentate P-containing ligand represented by Formula I is a phosphite.

In another embodiment, $X^{11}$ and $X^{12}$ may each represent oxygen, and $X^{13}$, a single bond; or $X^{11}$ and $X^{13}$ may each represent oxygen and $X^{12}$, a single bond, so that the phosphorus atom surrounded by $X^{11}$, $X^{12}$, and $X^{13}$ is the central atom of a phosphonite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$ and $X^{22}$ may each represent oxygen and $X^{23}$, a single bond; or $X^{21}$ and $X^{23}$ may each represent oxygen and $X^{22}$, a single bond, so that the phosphorus atom surrounded by $X^{21}$, $X^{22}$, and $X^{23}$ may be the central atom of a phosphonite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphite, the multidentate ligand represented by Formula I is a phosphite-phosphonite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphonite, the multidentate P-containing ligand represented by Formula I is a phosphonite. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphinite, the multidentate P-containing ligand represented by Formula I is a phosphonite-phosphinite and is an example of a mixed P-containing ligand. When the phosphorus atom surrounded by $X^{11}$, $X^{12}$, and $X^{13}$ is the central atom of a phosphonite and the phosphorus atom surrounded by $X^{21}$, $X^{22}$, and $X^{23}$ is the central atom of a phosphine, the multidentate P-containing ligand represented by Formula I is a phosphonite-phosphine and is an example of a mixed P-containing ligand.

In another embodiment, $X^{13}$ may represent oxygen and $X^{11}$ and $X^{12}$, each a single bond; or $X^{11}$ may represent oxygen and $X^{12}$ and $X^{13}$, each a single bond, so that the phosphorus atom surrounded by $X^{11}$, $X^{12}$, and $X^{13}$ is the central atom of a phosphinite. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}$, $X^{22}$, and $X^{23}$ may be the central atom of a phosphinite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphite, the multidentate P-containing ligand represented by Formula I is a phosphite-phosphinite and is an example of a mixed P-containing ligand. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphinite, the multidentate P-containing ligand represented by Formula I is a phosphinite. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphine, the multidentate P-containing ligand represented by Formula I is a phosphinite-phosphine and is an example of a mixed P-containing ligand.

In another embodiment, $X^{11}$, $X^{12}$, and $X^{13}$ may each represent a single bond, so that the phosphorus atom surrounded by $X^{11}$, $X^{12}$, and $X^{13}$ is the central atom of a phosphine. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphite, the multidentate P-containing ligand represented by Formula I is a phosphite-phosphine and is an example of a mixed P-containing ligand. When the phosphorus atom surrounded by $X^{11}$, $X^{12}$, and $X^{13}$ is the central atom of a phosphine and the phosphorus atom surrounded by $X^{21}$, $X^{22}$, and X²³ is the central atom of a phosphine, the multidentate P-containing ligand represented by Formula I is a phosphine.

Bridging group Y may be aryl groups substituted, for example, with $C_1$-$C_4$ hydrocarbyl, or halogen such as fluorine, chlorine, or bromine, or halogenated hydrocarbyl such as trifluoromethyl, or aryl such as phenyl, or unsubstituted aryl groups, for example those with 6 to 20 carbon atoms in the aromatic system, for example 2,2'-biphenyl, 1,1'-bi-2-naphthyl, or pyrocatechol.

Radicals $R^{11}$ and $R^{12}$ may independently represent identical or different organic radicals. $R^{11}$ and $R^{12}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{21}$ and $R^{22}$ may independently represent identical or different organic radicals. $R^{21}$ and $R^{22}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{11}$ and $R^{12}$ may be single or bridged. Radicals $R^{21}$ and $R^{22}$ may also be single or bridged. Radicals $R^{11}$, $R^{12}$, $R^{21}$, and $R^{22}$ may all be single, or two may be bridged and two single, or all four may be bridged in the manner described.

The P-containing ligand may also be a polymeric ligand composition, as disclosed, for example, in U.S. Pat. Nos. 6,284,865; 6,924,345; or United States Published Patent Application No. 2003/135014. Methods for preparing such polymeric ligand compositions are well known in the art and are disclosed, for example, in the above cited references.

The catalyst may comprise at least one monodentate P-containing ligand selected from the group consisting of a phosphite, a phosphonite, a phosphinite, and a phosphine or a combination of such members. The monodentate P-containing ligand may be added as an additional component of the catalyst when a multidentate P-containing ligand is used, or it may be present, for example, as an impurity from the synthesis of the P-containing ligand, or the monodentate P-containing ligand may be used without a multidentate P-containing ligand. The monodentate P-containing ligand may be represented by Formula II $$P(X^1R^{31})(X^2R^{32})(X^3R^{33}) \quad \text{Formula II}$$

wherein $X^1$, $X^2$, $X^3$ independently represent oxygen or a single bond, and $R^{31}$, $R^{32}$, $R^{33}$ independently represent identical or different, single or bridged organic radicals.

It is to be understood that Formula II may represent a single compound or a mixture of different compounds having the indicated formula.

In one embodiment, all of the groups $X^1$, $X^2$, and $X^3$ may represent oxygen, so that Formula II represents a phosphite of formula $P(OR^{31})(OR^{32})(OR^{33})$, wherein $R^{31}$, $R^{32}$, and $R^{33}$ have the meanings defined herein.

If one of the groups $X^1$, $X^2$, and $X^3$ represents a single bond and two groups represent oxygen, Formula II represents a phosphonite of formula $P(OR^{31})(OR^{32})(R^{33})$, $P(R^{31})(OR^{32})(OR^{33})$, or $P(OR^{31})(R^{32})(OR^{33})$, wherein $R^{31}$, $R^{32}$, and $R^{33}$ have the meanings defined herein.

If two of the groups $X^1$, $X^2$, and $X^3$ represent single bonds and one group represents oxygen, Formula II represents a phosphinite of formula $P(OR^{31})(R^{32})(R^{33})$ or $P(R^{31})(OR^{32})(R^{33})$ or $P(R^{31})(R^{32})(OR^{33})$, wherein $R^{31}$, $R^{32}$, and $R^{33}$ have the meanings defined herein.

The groups $X^1$, $X^2$, $X^3$ may independently represent oxygen or a single bond. If all the groups $X^1$, $X^2$, and $X^3$ represent single bonds, Formula II represents a phosphine of formula $P(R^{31})(R^{32})(R^{33})$, wherein $R^{31}$, $R^{32}$, and $R^{33}$ have the meanings defined herein.

Radicals $R^{31}$, $R^{32}$, and $R^{33}$ may independently represent identical or different organic radicals, for example hydrocarbyl radicals comprising 1 to 10 carbon atoms, such as methyl, ethyl, n-propyl, isopropyl, n-butyl, isobutyl, s-butyl, and t-butyl, aryl groups such as phenyl, o-tolyl, m-olyl, p-tolyl, 1-naphthyl, or 2-naphthyl, or hydrocarbyl radicals comprising 1 to 20 carbon atoms, such as 1,1'-biphenol or 1,1'-binaphthol. The $R^{31}$, $R^{32}$, and $R^{33}$ radicals may be connected to one another directly, meaning not solely via the central phosphorus atom. Alternatively, the $R^{31}$, $R^{32}$, and $R^{33}$ radicals may be not directly connected to one another.

For example, $R^{31}$, $R^{32}$, and $R^{33}$ may be selected from the group composed of phenyl, o-tolyl, m-tolyl, and p-tolyl. As another example, a maximum of two of the $R^{31}$, $R^{32}$, and $R^{33}$ groups may be phenyl. Alternatively, a maximum of two of the $R^{31}$, $R^{32}$, and $R^{33}$ groups may be o-tlyl.

Compounds of Formula IIa,

$$(\text{o-tolyl-O}—)_w(\text{m-tolyl-O}—)_x(\text{p-tolyl-O}—)_y(\text{phenyl-O}—)_zP \quad \text{Formula IIa}$$

may be used as the monodentate P-containing ligand, wherein w, x, y, and z are integers, and the following conditions apply: w+x+y+z=3 and w, z≤2.

Examples of compounds of Formula IIa include (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-toyl-O—)P, (o-tolyl-O—)$_2$(p-tolyl-O—)P, (o-tolyl-O—)(m-tolyl-O—)(p-tolyl-O—)P, (m-toyl-O—)$_3$P, (o-tolyl-O—)(m-tolyl-O—)$_2$P, (o-tolyl-O—)$_2$(m-tolyl-O—)P, or mixtures of such compounds.

Mixtures containing (m-tolyl-O—)$_3$P, (m-tolyl-O—)$_2$(p-tolyl-O—)P, (m-tolyl-O—) (p-tolyl-O—)$_2$P, and (p-tolyl-O—)$_3$P can be obtained, for example, by reacting a mixture containing m-cresol and p-cresol, in particular in a molar ratio of 2:1 as occurs in the distillative processing of crude oil, with a phosphorus trihalide such as phosphorus trichloride.

Additional examples of monodentate P-containing ligands are the phosphites disclosed in U.S. Pat. No. 6,770,770 and referred to herein as phosphites of Formula IIb,

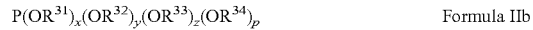

$$P(OR^{31})_x(OR^{32})_y(OR^{33})_z(OR^{34})_p \quad \text{Formula IIb}$$

wherein $R^{31}$ is an aromatic radical having a $C_1$-$C_{18}$ alkyl substituent in the o-position relative to the oxygen atom which connects the phosphorus atom to the aromatic system, or having an aromatic substituent in the o-position relative to the oxygen atom which connects the phosphorus atom to the aromatic system, or having an aromatic system fused on in the o-position relative to the oxygen atom which connects the phosphorus atom to the aromatic system;

$R^{32}$ is an aromatic radical having a $C_1$-$C_{18}$ alkyl substituent in the m-position relative to the oxygen atom which connects the phosphorus atom to the aromatic system, or having an aromatic substituent in the m-position relative to the oxygen atom which connects the phosphorus atom to the aromatic system, or having an aromatic system fused on in the m-position relative to the oxygen atom which connects the phosphorus atom to the aromatic system, where the aromatic radical bears a hydrogen atom in the o-position relative to the oxygen atom which connects the phosphorus atom to the aromatic system;

$R^{33}$ is an aromatic radical having a $C_1$-$C_{18}$ alkyl substituent in the p-position relative to the oxygen atom which connects the phosphorus atom to the aromatic system, or having an aromatic substituent in the p-position relative to the oxygen atom which connects the phosphorus atom to the aromatic system, where the aromatic radical bears a hydrogen atom in the o-position relative to the oxygen atom which connects the phosphorus atom to the aromatic system;

$R^{34}$ is an aromatic radical which bears substituents other than those defined for $R^{31}$, $R^{32}$, and $R^{33}$ in the o-, m-, and p-position relative to the oxygen atom which connects the phosphorus atom to the aromatic system, where the aromatic radical bears a hydrogen atom in the o-position relative to the oxygen atom which connects the phosphorus atom to the aromatic system;

x is 1 or 2; and y, z, and p independently of one another are 0, 1, or 2, provided that x+y+z+p=3.

Examples of radical $R^{31}$ include o-tolyl, o-ethylphenyl, o-n-propylphenyl, o-isopropylphenyl, o-n-butylphenyl, o-sec-butylphenyl, o-tert-butylphenyl, (o-phenyl)phenyl, or 1-naphthyl groups.

Examples of radical $R^{32}$ include m-tolyl, m-ethylphenyl, m-n-propylphenyl, m-isopropylphenyl, m-n-butylphenyl, m-sec-butylphenyl, m-tert-butylphenyl, (m-phenyl)-phenyl, or 2-naphthyl groups.

Examples of radical $R^{33}$ include p-tolyl, p-ethylphenyl, p-n-propylphenyl, p-isopropylphenyl, p-n-butylphenyl, p-sec-butylphenyl, p-tert-butylphenyl, or (p-phenyl)phenyl groups.

Radical $R^{34}$ may be, for example, phenyl.

The indices x, y, z, and p in compounds of Formula IIb may have the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Examples of phosphites of Formula IIb are those in which p is zero, and $R^{31}$, $R^{32}$, and $R^{33}$ are independently selected from o-isopropylphenyl, m-tolyl, and p-tolyl.

Additional examples of phosphites of Formula IIb are those in which $R^{31}$ is the o-isopropylphenyl radical, $R^{32}$ is the m-tolyl radical, and $R^{33}$ is the p-tolyl radical, with the indices listed in the above table; also those in which $R^{31}$ is the o-tolyl radical, $R^{32}$ is the m-tolyl radical, and $R^{33}$ is the p-tolyl radical, with the indices listed in the table; also those in which $R^{31}$ is the 1-naphthyl radical, $R^{32}$ is the m-tolyl radical, and $R^{33}$ is the p-tolyl radical, with the indices listed in the table; also those in which $R^{31}$ is the o-tolyl radical, $R^{32}$ is the 2-naphthyl radical, and $R^{33}$ is the p-tolyl radical, with the indices listed in the table; and lastly, those in which $R^{31}$ is the o-isopropylphenyl radical, $R^{32}$ is the 2-naphthyl radical, and $R^{33}$ is the p-tolyl radical, with the indices listed in the table; and mixtures of these phosphites.

Phosphites having the Formula IIb can be obtained as follows:

a) phosphorus trihalide is reacted with alcohol selected from the group comprising $R^{31}OH$, $R^{32}OH$, $R^{33}OH$ and $R^{34}OH$ or mixtures thereof to obtain a dihalogenophosphoric acid monoester, b) the aforementioned dihalogenophosphoric acid monoesters are reacted with alcohol selected from the group comprising $R^{31}OH$, $R^{32}OH$, $R^{33}OH$ and $R^{34}OH$ or mixtures thereof to obtain a dihalogenophosphoric acid diester, and c) the aforementioned monohalogenophosphoric acid diester is reacted with alcohol selected from the group comprising $R^{31}OH$, $R^{32}OH$, $R^{33}OH$ and $R^{34}H$ or mixtures thereof to obtain phosphite having the Formula IIb.

The reaction can be performed in three separate steps. It is also possible to combine two of the three steps, for example a) with b) or b) with c). Alternatively, all steps a), b), and c) can be combined with each other.

Suitable parameters and quantities of the alcohols selected from the group comprising $R^{31}OH$, $R^{32}OH$, $R^{33}OH$ and $R^{34}OH$ or mixtures thereof can be easily determined by conducting a few simple preliminary experiments.

Suitable phosphorus trihalides are in principle all phosphorus trihalides in which preferable Cl, Br, I, particularly Cl is used as the halide, as well as mixtures thereof. It is also possible to use mixtures of different equally or differently halogen-substituted phosphines as the phosphorus trihalide, for example $PCl_3$. Further details regarding the reaction conditions during the production of phosphites of Formula IIb and regarding the treatment are disclosed in DE-A 199 53 058.

Phosphites of Formula IIb can also be used as a mixture of different phosphites as ligand. Such a mixture can be formed, for example, in the preparation of phosphites of Formula IIb.

In one embodiment of the process of the invention, the phosphorus-containing ligand of the catalyst and/or the free phosphorus-containing ligand is selected from at least one multidentate P-containing ligand selected from the group consisting of a phosphite, a phosphonite, a phosphinite, a phosphine, and a mixed P-containing ligand or a combination of such members, and at least one monodentate P-containing ligand selected from tritolyl phosphite and the phosphites of Formula IIb wherein $R^{31}$, $R^{32}$, and $R^{33}$ are independently selected from o-isopropylphenyl, m-tolyl, and p-tolyl, $R^{34}$ is phenyl, x is 1 or 2, and y, z, and p are independently 0, 1, or 2, provided that x+y+z+p=3; and mixtures thereof.

Examples of multidentate P-containing ligands include the following:

1) the compounds of Formula I, II, III, IV, and V disclosed in U.S. Pat. No. 5,723,641;
2) the compounds of Formula I, II, III, IV, V, VI, and VII disclosed in U.S. Pat. No. 5,512,696, for example the compounds used in Examples 1 through 31 therein;
3) the compounds of Formula I, II, III, IV, V, VI, VII, VIII, IX, X, XI, XII, XIII, XIV, and XV disclosed in U.S. Pat. No. 5,821,378, for example the compounds used in Examples 1 through 73 therein;
4) the compounds of Formula I, II, III, IV, V, and VI disclosed in U.S. Pat. No. 5,512,695, for example the compounds used in Examples 1 through 6 therein;
5) the compounds of Formula I, II, III, IV, V, VI, VII, VIII, IX, X, XI, XII, XIII, and XIV disclosed in U.S. Pat. No.

5,981,772, for example the compounds used in Examples 1 through 66 therein;

6) the compounds disclosed in U.S. Pat. No. 6,127,567, for example the compounds used in Examples 1 through 29 therein;

7) the compounds of Formula I, II, III, IV, V, VI, VII, VIII, IX, and X disclosed in U.S. Pat. No. 6,020,516, for example the compounds used in Examples 1 through 33 therein;

8) the compounds disclosed in U.S. Pat. No. 5,959,135, for example the compounds used in Examples 1 through 13 therein;

9) the compounds of Formula I, II, and III disclosed in U.S. Pat. No. 5,847,191;

10) the compounds disclosed in U.S. Pat. No. 5,523,453, for example the compounds of Formula 1, 2, 3, 4, 5, 6, 7, 8, 9, 10, 11, 12, 13, 14, 15, 16, 17, 18, 19, 20, and 21 therein;

11) the compounds disclosed in U.S. Pat. No. 5,693,843, for example the compounds of Formula I, II, III, IV, V, VI, VII, VII, IX, X, XI, XII, and XIII, for example the compounds used in Examples 1 through 20 therein;

12) the compounds of Formula V, VI, VII, VIII, IX, X, XI, XII, XIII, XIV, XV, XVI, XVII, XVIII, XIX, XX, XXI, XXII, XXIII, XXIV, XXV, and XXVI disclosed in U.S. Pat. No. 6,893,996;

13) the compounds disclosed in published patent application WO 01/14392, for example the compounds illustrated in Formula V, VI, VII, VIII, IX, X, XI, XII, XIII, XIV, XV, XVI, XVII, XXI, XXII, and XXIII therein;

14) the chelating compounds disclosed in U.S. Pat. No. 6,242,633, for example the compounds of Formula If, Ig, and Ih;

15) the compounds disclosed in U.S. Pat. No. 6,521,778, for example the compounds of Formula I, Ia, Ib, and Ic, for example the compounds referred to as Ligand I and II;

16) the compounds disclosed in published patent application WO 02/13964, for example the compounds of Formula Ia, Ib, Ic, Id, Ie, If, Ig, Ih, Ii, Ij, and Ik, for example the compounds referred to as Ligand 1, 2, 3, 4, 5, and 6;

17) the compounds disclosed in German Patent Application DE 100 460 25;

18) the chelating compounds disclosed in U.S. Pat. No. 7,022,866, for example the compounds of Formula 1 and 2, for example the compounds referred to as Ligand 1 and 2;

19) the compounds disclosed in United States Published Patent Application No. 2005/0090677, for example the compounds of Formula 1, 1a, 1b, 1c, 1d, 1e, 1f, 1g, 1h, 1i, 1j, 1k, 1l, 1m, 1n, 1o, 2, and 3;

20) the compounds disclosed in United States Published Patent Application No. 2005/0090678, for example the compounds of Formula 1 and 2, for example the compounds referred to as Ligand 1, 2, 3, 4, 5, and 6;

21) the compounds disclosed in published patent application WO 2005/042547, for example the compounds of Formula 1, 1a, 1b, 1c, 1d, 1e, 1f, 1g, 1h, 1i, 1j, 1k, 1l, 1m, 1n, 1o, 2, 3, 4, 5, and 6, for example the compounds referred to as Ligand 1, 2, 3, and 4;

22) the chelating compounds disclosed in U.S. Pat. No. 6,169,198, for example the compounds of Formula I;

23) the compounds disclosed in U.S. Pat. No. 6,660,877, for example the compounds of Formula I, II, and III, for example the compounds used in Examples 1 through 27 therein;

24) the compounds disclosed in U.S. Pat. No. 6,197,992, for example the compounds of Ligand A and B: and 25) the compounds disclosed in U.S. Pat. No. 6,242,633, for example the compounds of Formula I, Ia, Ib, Ic, Id, Ie, If, Ig, and Ih.

These references also disclose methods for preparing multidentate ligands of Formula I.

Additional examples of ligands which, in combination with nickel, form highly active catalysts for the hydrocyanation of 1,3-butadiene or 3-pentenenitrile and the isomerization of 2-methyl-3-butenenitrile to 3-pentenenitrile are bidentate phosphite ligands are of the following structural formulas:

Formula IIIa

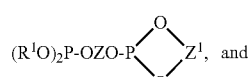

Formula IIIb

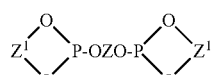

Formula IIIc wherein in IIIa, IIIb, and IIIc $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulas IV, V, VI, VII, and VIII:

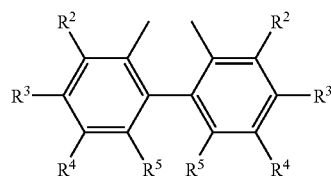

IV

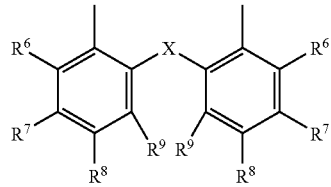

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or $CH(R^{10})$;
$R^{10}$ is H or $C_1$ to $C_{12}$ alkyl;

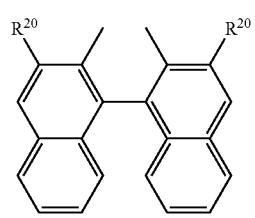

VI

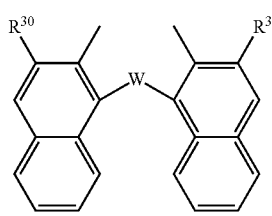

and wherein
$R^{20}$ and $R^{30}$ are independently selected from the group consisting of H, $C_1$ to $C_{12}$ alkyl, and $C_1$ to $C_{12}$ alkoxy; and $CO_2R^{13}$,
$R^{13}$ is $C_1$ to $C_{12}$ alkyl or $C_6$ to $C_{10}$ aryl, unsubstituted or substituted with $C_1$ to $C_4$ alkyl;
W is O, S, or $CH(R^{14})$;
$R^{14}$ is H or $C_1$ to $C_{12}$ alkyl;

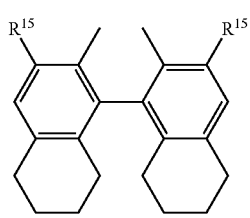

wherein $R^{15}$ is selected from the group consisting of H, $C_1$ to $C_{12}$ alkyl, and $C_1$ to $C_{12}$ alkoxy and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl In the structural formulas IIIa, IIIb, IIIc, and IV through VIII, the $C_1$ to $C_{12}$ alkyl, and $C_1$ to $C_{12}$ alkoxy groups may be straight chain or branched.

It is to be understood that structural formulas IIIa, IIIb, and IIIc may represent a single compound or a mixture of different compounds having the indicated formulas.

Examples of bidentate phosphite ligands that are useful in the present process include those having the formulas IX to XXXII, shown below wherein for each formula, $R^{17}$ is selected from the group consisting of methyl, ethyl or isopropyl, and $R^{18}$ and $R^{19}$ are independently selected from H or methyl:

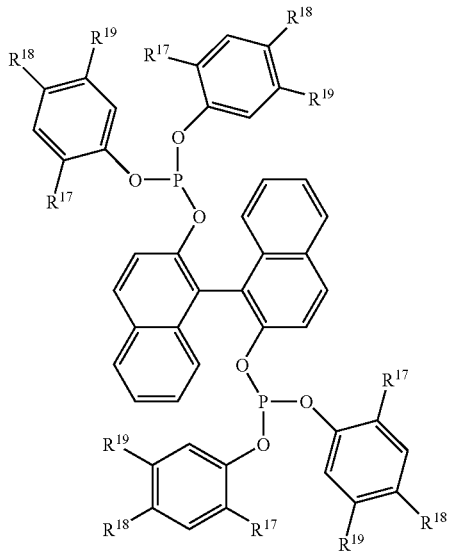

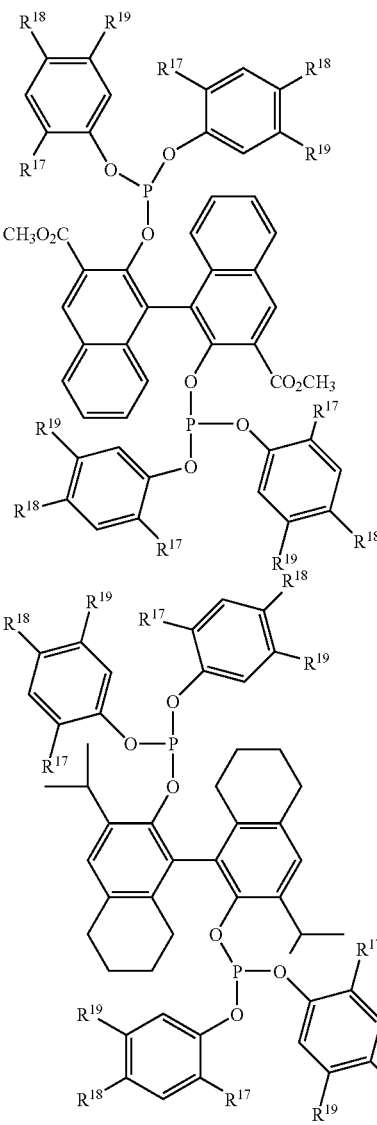

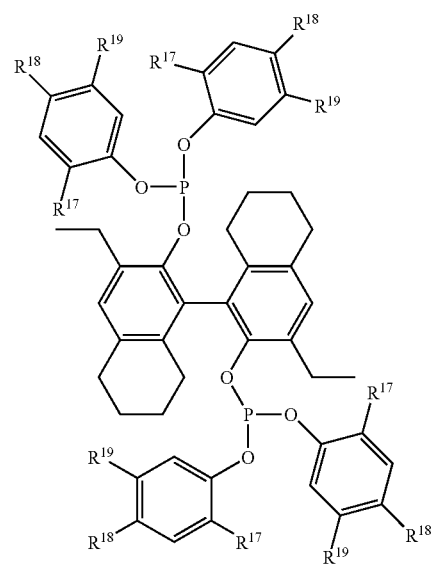

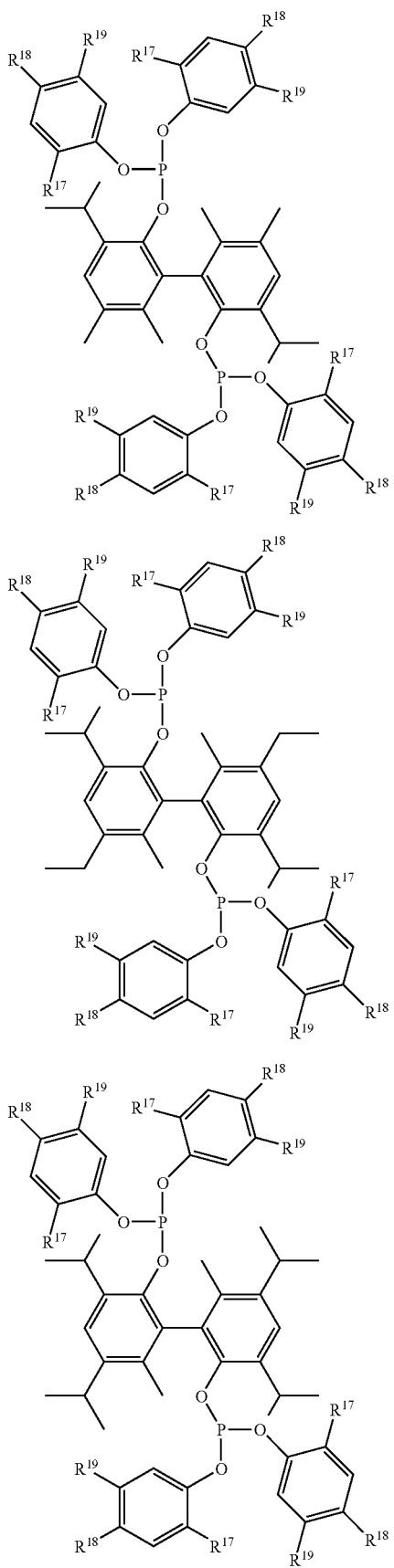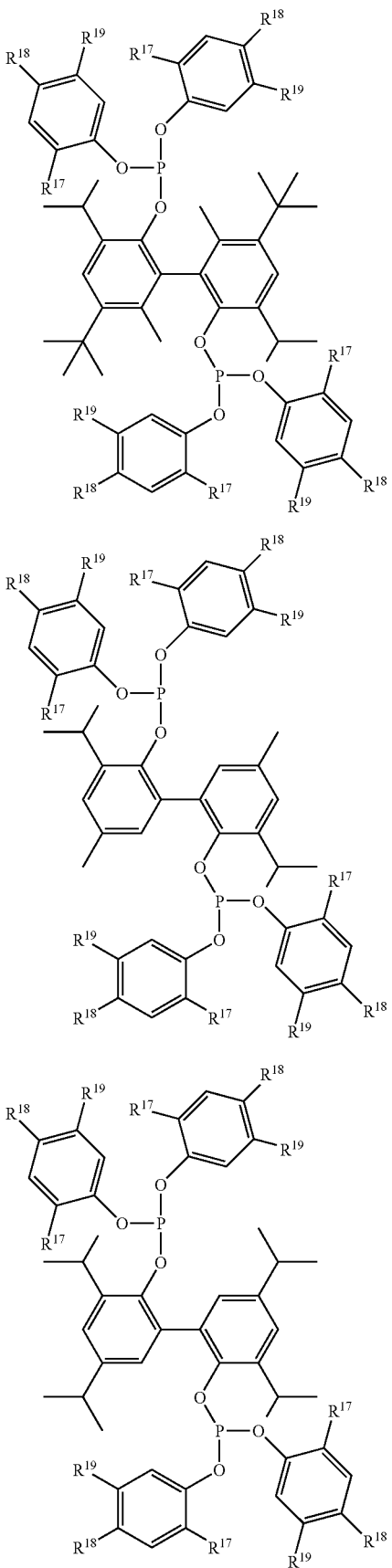

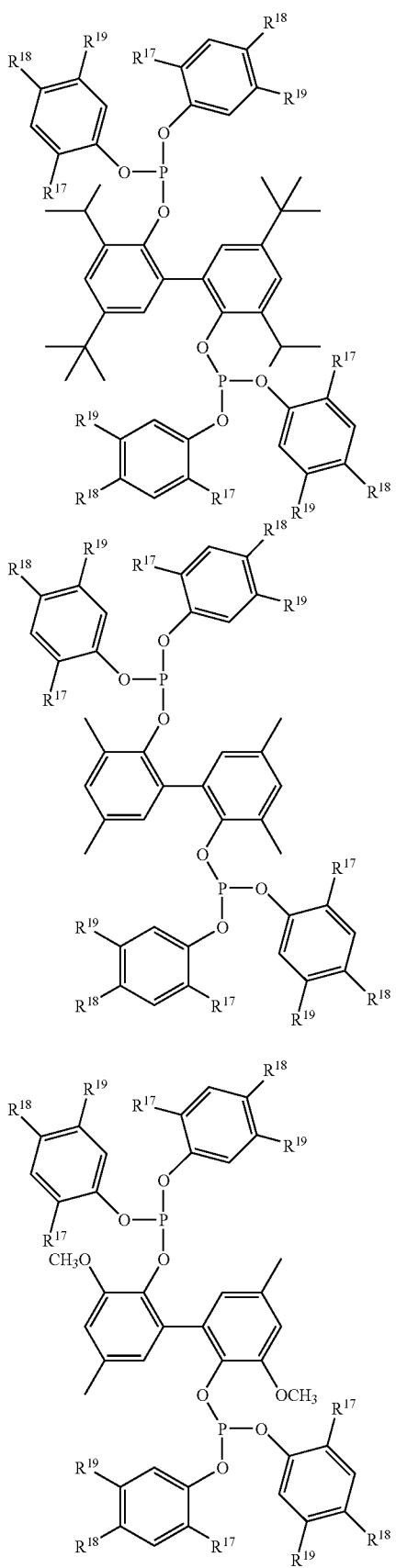
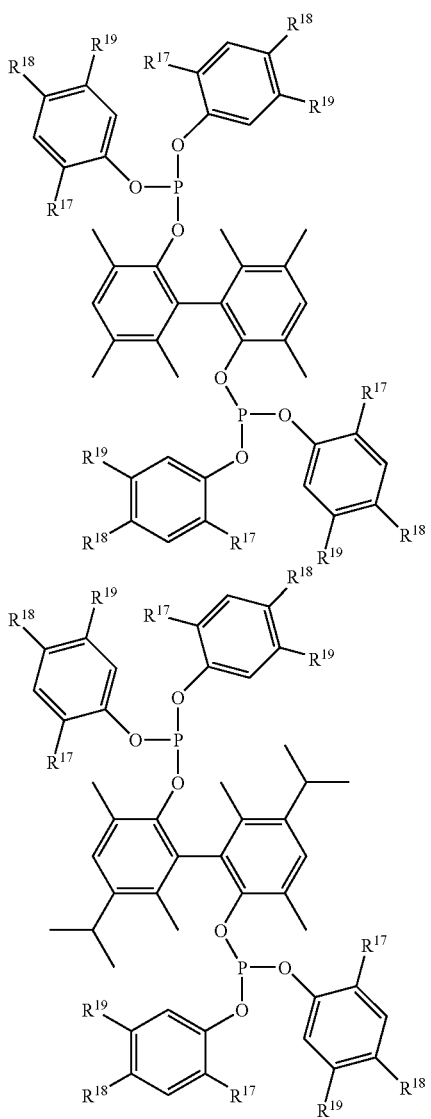
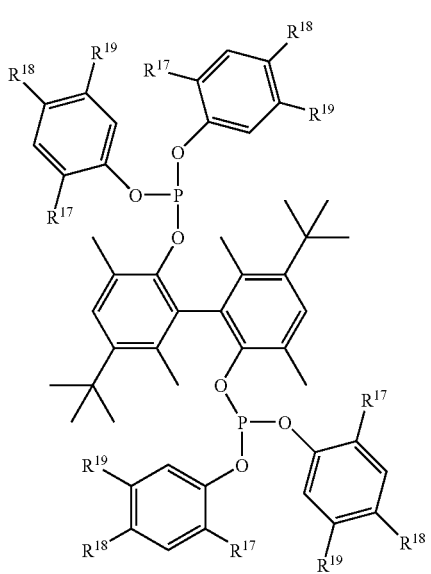

XXV
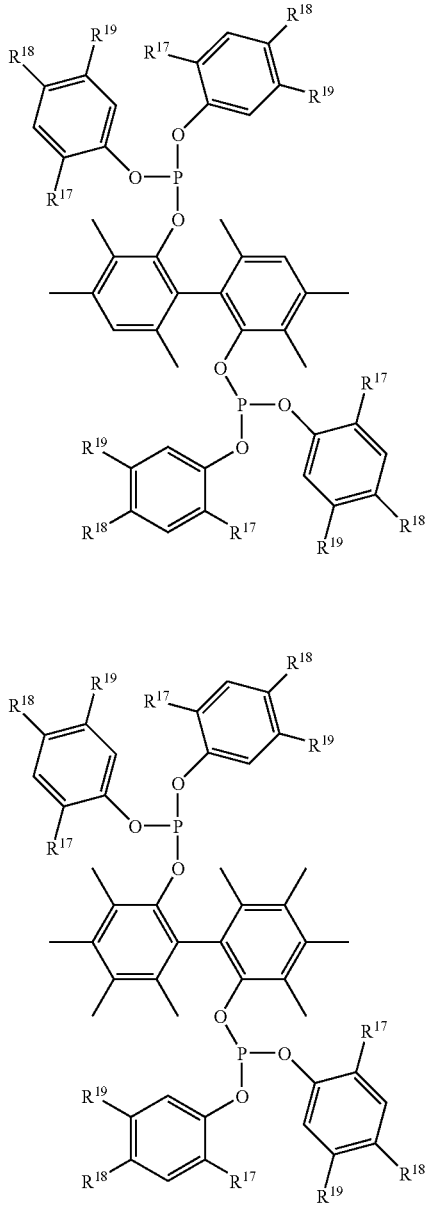
XXVI
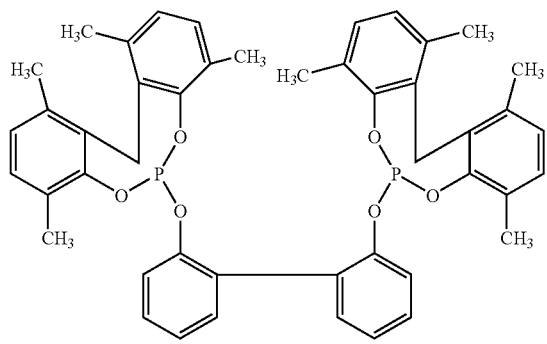
XXVII
XXVIII
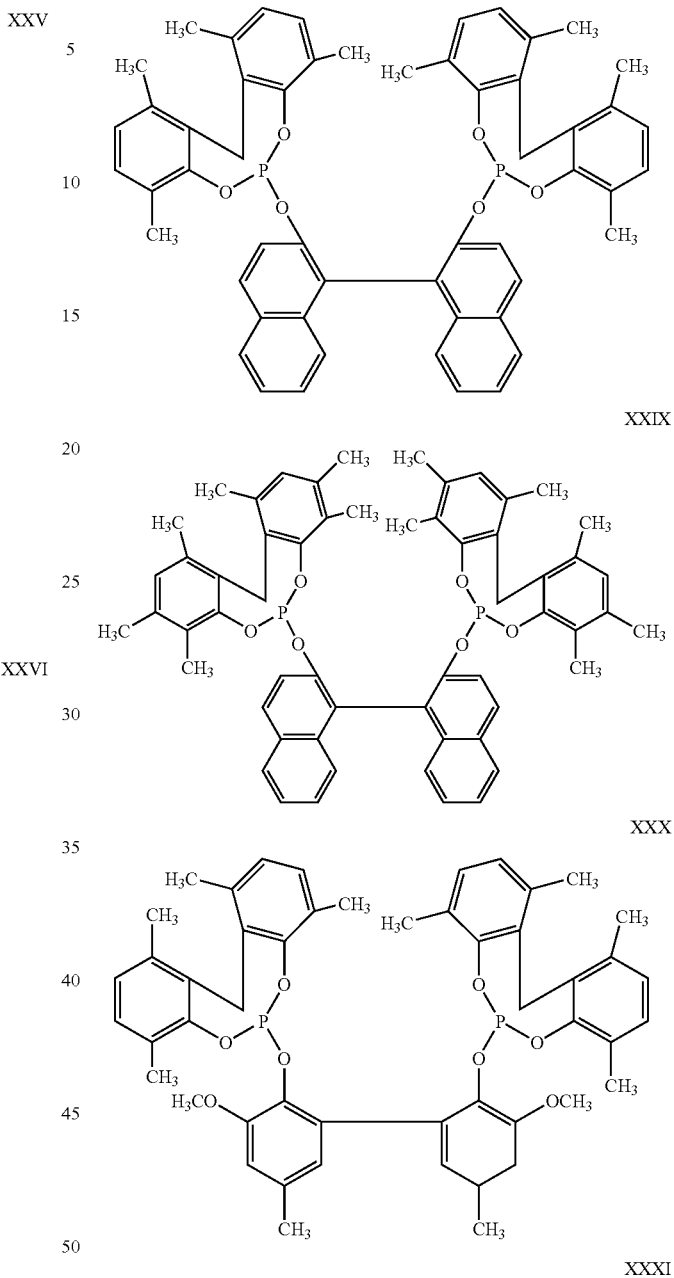
XXIX
XXX
XXXI
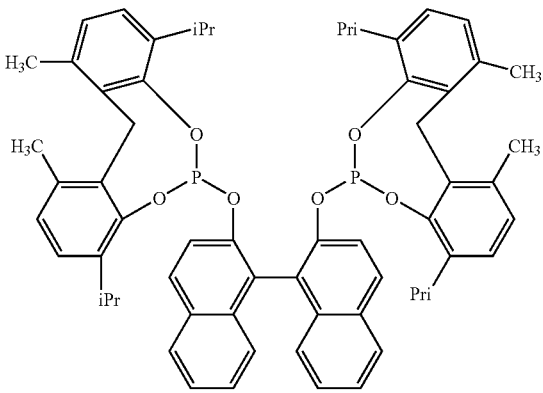

XXXII

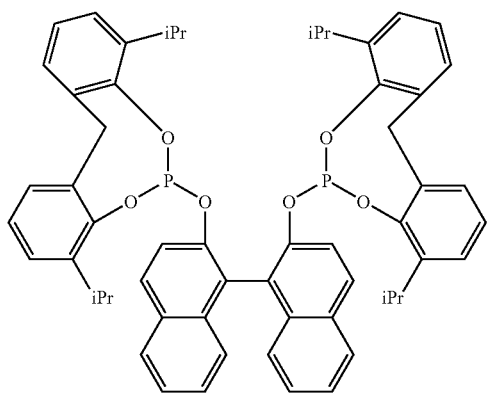

Additional examples of bidentate phosphite ligands that are useful in the present process include a ligand selected from a member of the group represented by Formulas XXXIII and XXXIV, in which all like reference characters have the same meaning, except as further explicitly limited:

Formula XXXIII

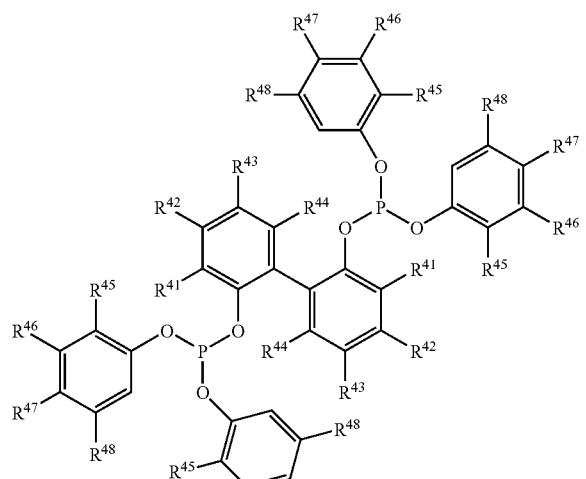

Formula XXXIV

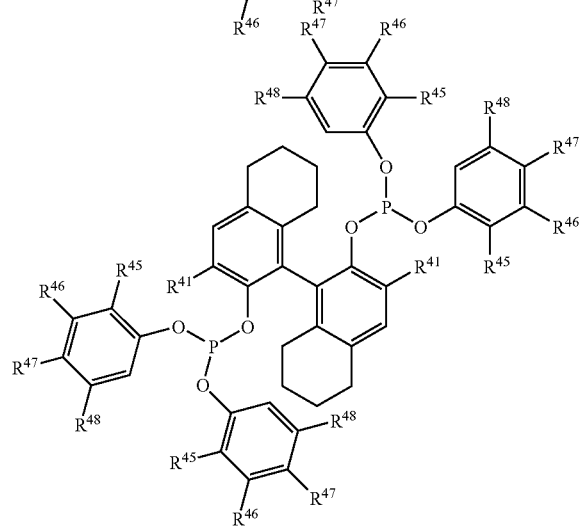

wherein each $R^{41}$ is independently selected from the group consisting of primary and secondary hydrocarbyl of 1 to 6 carbon atoms;

each $R^{45}$ is independently selected form the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms.

Some ligands useful in the catalyst compositions of the present invention are generally described in U.S. Pat. Nos. 6,171,996 and 5,512,696 and are illustrated above by Formula XXXIII and Formula XXXIV, as defined above. In one preferred Formula XXXIII ligand (Ligand "A" in the Examples), each $R^{41}$ is isopropyl, each $R^{45}$ is methyl, each $R^{42}$, $R^{46}$, $R^{47}$, and $R^{48}$ is hydrogen, and each $R^{43}$ and $R^{44}$ is methyl. In a second preferred Formula XXXIII ligand (Ligand "B" in the Examples), each $R^{41}$ is isopropyl, each $R^{45}$ is methyl, each $R^{42}$ $R^{46}$, and $R^{48}$ is hydrogen, and each $R^{43}$, $R^{44}$, and $R^{47}$ is methyl. In one preferred Formula XXXIV ligand (Ligand "C" in the Examples), each $R^{41}$ is isopropyl, each $R^{45}$ is methyl, and each $R^{46}$, $R^{47}$, and $R^{48}$ is hydrogen.

It is to be understood that the formulas above are two-dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Formula XXXIII and Formula XXXIV, respectively, can bring the two phosphorus atoms of each Formula in closer proximity to one another and can allow the phosphite ligand to bind to nickel in a bidentate fashion.

The P-containing ligands useful in the present invention may be prepared by any suitable synthetic means known in the art. For example, in general the multidentate P-containing ligands may be synthesized analogously to the method described in U.S. Pat. Nos. 6,171,996 and 5,512,696, both of which are incorporated herein by reference. For example, the reaction of two equivalents of an ortho-substituted phenol with phosphorus trichloride gives the corresponding phosphorochloridite. The reaction of the phosphorochloridite with the desired substituted biphenol or octahydrobinaphthol in the presence of triethylamine gives the bidentate phosphite ligand. The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture.

The multidentate P-containing ligand itself or mixtures of the multidentate P-containing ligand and at least one monodentate P-containing ligand are suitable for use, that is, appropriate, in the process of the invention if the ligand or ligand mixture gives acceptable results according to at least one protocol of the 2PN Hydrocyanation Test Method specified herein. The 2PN Hydrocyanation Test Method utilizes three protocols which differ in the method of HCN delivery to the reaction mixture. A catalyst composition comprising a zero-valent nickel and the multidentate P-containing ligand is first prepared by combining the zero-valent nickel compound Ni(COD)$_2$, wherein COD is 1,5-cyclooctadiene, with the multidentate P-containing ligand in toluene solvent. The resulting catalyst composition is then contacted with a solution comprising cis-2PN and a Lewis acid promoter. The next step is to contact this reaction solution with anhydrous, uninhibited HCN at about 50° C. for about 16 hours according to one of three protocols. The mole ratio of promoter to nickel present in the reaction mixture is about 0.96/1; the mole ratio of multidentate P-containing ligand to zero-valent nickel in the reaction mixture is in the range of about 1/1 to about 1.2/1; and the initial mole ratio of 2PN to nickel is about 110/1 to about 130/1.

Acceptable results according to the 2PN Hydrocyanation Test Method are those wherein the 2PN (that is, cis-2PN and trans-2PN) conversion to dinitriles is at least 0.1% according to at least one protocol of the 2PN Hydrocyanation Test Method. Also included in the 2PN conversion is the conversion to dinitriles of any 3PN and/or 4PN derived from isomerization of the 2PN. As used herein, the term dinitriles includes ADN, MGN, and 2-ethylsuccinonitrile. An analytical method such as gas chromatography can be used to determine the amounts of dinitriles produced. Acceptable results according to the 2PN Hydrocyanation Test Method are indicative of a ligand or a ligand mixture's ability to form an active catalyst, within a catalyst composition, to convert cis-2PN to useful products, such as dinitriles, 3PN, and 4PN, under the conditions of the 2PN Hydrocyanation Test Method.

The multidentate P-containing ligands useful in the catalyst compositions employed in the present invention may be prepared by any suitable synthetic means known in the art, for example as disclosed in at least some of the references disclosing examples of multidentate P-containing ligands. For example, the multidentate P-containing ligands of Formula II may be synthesized as described in U.S. Pat. No. 6,171,996, which is incorporated herein by reference. For Ligand "A," for example, the reaction of two equivalents of o-cresol with phosphorus trichloride gives the corresponding phosphorochloridite. The reaction of the phosphorochloridite with 3,3'-di-iso-propyl-5,5',6,6'-tetra-methyl-2,2'-biphenol in the presence of triethylamine gives Ligand "A." The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture. The bidentate phosphite ligand itself or these bidentate/monodentate phosphite ligand mixtures are suitable for use with the present invention.

The catalyst compositions employed for this process should ideally be substantially free of carbon monoxide, oxygen, and water and may be preformed or prepared in situ according to techniques well known in the art, as also described in U.S. Pat. No. 6,171,996. For example, the catalyst composition may be formed by contacting a bidentate phosphite ligand with a zero-valent nickel compound having ligands easily displaced by multidentate P-containing ligands, such as $Ni(COD)_2$, $Ni[P(O-o-C_6H_4CH_3)_3]_3$, and $Ni[P(O-o-C_6H_4CH_3)_3]_2(C_2H_4)$, all of which are well known in the art, wherein 1,5-cyclooctadiene (COD), tris(orthotolyl)phosphite $[P(O-o-C_6H_4CH_3)_3]$, and ethylene $(C_2H_4)$ are the easily displaced ligands. Elemental nickel, preferably nickel powder, when combined with a halogenated catalyst, as described in U.S. Pat. No. 3,903,120, is also a suitable source of zero-valent nickel. Alternatively, divalent nickel compounds may be combined with a reducing agent, to serve as a source of zero-valent nickel in the reaction, in the presence of the multidentate P-containing ligands. Suitable divalent nickel compounds include compounds of the formula $NiY_2$ where Y is halide, carboxylate or acetylacetonate. Suitable reducing agents include metal borohydrides, metal aluminum hydrides, metal alkyls, Zn, Fe, Al, Na, or $H_2$. See, for example, U.S. Pat. No. 6,893,996, which is incorporated herein by reference.

In the catalyst composition, the multidentate P-containing ligand may be present in excess of what can theoretically be coordinated to the nickel at a given time, unless it detracts from the beneficial aspects of the invention. For example, the nature of the catalyst compositions of ligands of Formula XXXIII and XXXIV is such that effective catalysts may be formed at any molar ratio of ligand to nickel, but the preferred range of the molar ratio of ligand to nickel is from about 1/1 to about 4/1.

The pentenenitrile hydrocyanation process can be carried out in the presence of at least one Lewis acid promoter which affects both the activity and selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin, as described in the prior art. Examples include, but are not limited to, $BPh_3$, $ZnCl_2$, $CoI_2$, $SnCl_2$, $PhAlCl_2$, $Ph_3Sn(O_3SC_6H_5CH_3)$ and $Cu(O_3SCF_3)_2$. Preferred promoters include zinc chloride $ZnCl_2$, iron(II) chloride $FeCl_2$, and manganese(II) chloride $MnCl_2$, and mixtures thereof. U.S. Pat. No. 4,874,884 describes how synergistic combinations of promoters can be chosen to increase the catalytic activity of the catalyst system. The mole ratio of promoter to nickel present in the reaction can, for example, be in the range of about 0.1/1 to about 10/1, for example in the range of about 0.5/1 to about 1.2/1.

The catalyst composition may be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst composition.

To maximize pentenenitrile hydrocyanation rates while minimizing catalyst consumption through active nickel oxidation by HCN, the hydrocyanation reaction of the present invention should be performed in reactor systems providing efficient mass transfer of pentenenitriles, HCN, and catalyst and efficient removal of the heat of reaction. Such reactor systems are known in the art. The hydrocyanation reaction of the present invention can, in at least one embodiment, be effectively practiced in a continuous stirred tank reactor in which the reactor product is back-mixed well with the reaction mixture. In such a reactor system, the kinetics of the hydrocyanation reaction may be expected to be primarily governed by the reactor product composition. In another suitable embodiment, the hydrocyanation reaction of the present invention can be practiced in the reactor system disclosed in U.S. Pat. No. 4,382,038. In this reactor system, the primary reaction zone comprises a plurality of stages in series with the product from one stage continuously directed to a subsequent stage and the HCN added to each stage. The effluent from the primary reaction zone, comprising zero-valent nickel catalyst, unreacted pentenenitriles, unreacted HCN, and the dinitrile products is then sent to a secondary reaction zone where its temperature can be controlled and where no HCN is added to the effluent.

The continuous hydrocyanation reaction can, for example, be conducted between about 20° C. to about 90° C., for example in the range of about 35° C. to about 70° C., or for example in the range of about 45° C. to about 60° C.

While atmospheric pressure is satisfactory for carrying out the hydrocyanation, higher and lower pressures can be used. In this regard, pressures of from about 0.5 to about 10 atmospheres (about 50.7 to about 1013 kPa), for example, may be used. Higher pressures, up to 20,000 kPa or more, may be used, if desired, but any benefit that may be obtained thereby may not be justified in view of the increased cost of such operations.

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The overall feed molar ratio of HCN to zero-valent nickel may, for example, be in the range of about 100/1 to about 3000/1, for example in the range of about 300/1 to about 2000/1. At reactor startup, the reaction vessel may be partially charged, for example, with either a solution of a catalyst composition in substrate pentenenitriles or the reactor product from a previous reaction campaign, followed by the initiation of all reactor feeds. Continuous reactor product removal may begin upon establishing the desired fluid levels within the reaction vessel.

At least one potential advantage of using the catalyst compositions described above for the hydrocyanation of ethylenically unsaturated nitriles with reduced yield losses from the concurrent isomerization of 3PN to 2PN may be realized when the ratio of the concentration of 2PN to the concentration of 3PN in the reaction mixture is maintained from about 0.2/1 to about 10/1. Control of the ratio of the concentration of 2PN to the concentration of 3PN in the reaction mixture in this range can be established by controlling X, the overall feed molar ratio of 2PN to all unsaturated nitriles, by selecting a value for X in the range from about 0.001 to about 0.5, and controlling Z, the overall feed molar ratio of HCN to all unsaturated nitriles, by selecting a value for Z in the range from about 0.5 to about 0.99, such that the value of quotient Q, wherein $$Q = \frac{X}{\left[\frac{(\text{moles } 3PN + 4PN \text{ in the feed})/}{(\text{moles all unsaturated nitriles in the feed})}\right] - Z}$$

is in the range from about 0.2 to about 10, wherein 3PN is 3-pentenenitriles and 4PN is 4-pentenenitrile. Similarly, reduced yield losses from the concurrent isomerization of 3PN to 2PN may be realized when the ratio of the concentration of 2PN to the concentration of 3PN in the reaction mixture is maintained from about 1/1 to about 5/1. Control of this ratio in this range can be established by controlling X and Z by selecting a value for X in the range from about 0.01 to about 0.25, and by selecting a value for Z in the range from about 0.70 to about 0.99, such that Q is in the range from about 1 to about 5.

While not limited to any particular method, establishing the overall feed molar ratio of 2PN to all unsaturated nitrites may be accomplished by at least two different methods and/or combinations thereof. For example, the overall feed molar ratio of 2PN to all unsaturated nitrites can be controlled by addition of 2PN produced in an independent process or by direct recycle of the 2PN from the reaction product mixture within the process. The first method involves obtaining 2PN produced by a different process or prepared in a separate manufacturing facility. The desired feed molar ratio may then be achieved by blending the 2PN thus obtained with the other substrate pentenenitrile isomers in the appropriate proportions. Alternatively, the 2PN can originate from a pentenenitrile hydrocyanation process. For example, the 2PN in the reactor product of the present invention may be physically separated, along with the other unreacted unsaturated nitrites, from the dinitrile product and catalyst composition, for example, by vacuum distillation. Establishing the overall feed molar ratio of 2PN to all unsaturated nitriles may be accomplished, for example, by returning to the reaction mixture at least a portion of a stream selected from the group consisting of the fifth stream, the eleventh stream, the twelfth stream, the fifteenth stream and combinations thereof. (See sections below regarding these streams.) The stream(s) comprising the recovered 2PN may be recycled and/or blended with each other and/or other streams, for example refined 3PN, in the appropriate proportions to constitute a feed of ethylenically unsaturated nitrites to the reaction of the present invention with the desired molar ratios. The stream(s) comprising 2PN can be substantially free of other nitrites, or the 2PN can be present in a process stream which comprises additional nitrites.

In order for catalyst composition recovery to be possible via liquid-liquid extraction through contact with an extraction agent, phase separation of the extract and raffinate phases must occur in the extraction process. U.S. Pat. No. 3,773,809, which is incorporated herein in its entirety, discloses a process for separating an organic phosphorus compound or a zerovalent nickel complex of the organic phosphorus compound from a product fluid with a paraffin or cycloparaffin hydrocarbon solvent at a temperature of about 0° C. to about 100° C. to product a multiphase mixture wherein the organic phosphorus compounds and their metal complexes are contained predominantly in the hydrocarbon phase and the organic mono- and dinitrile and degradation products are contained in a separate phase. The reference also notes that the composition of the product fluid must be controlled so that the molar ratio of organic mononitrile to organic dinitrile contained therein is less than about 0.65 and preferably about 0.3 in order that a multiphase mixture is formed; separation of nickel is most effective from a dinitrile-rich system. Three methods given for controlling the molar ratio of mononitrile to dinitrile are controlling the level of hydrocyanation of the mononitrile, that is, the extent of mononitrile conversion to dinitrile, removing mononitrile, for example by flash distillation, and introducing added quantities of dinitrile. U.S. Pat. No. 3,773,809 further discloses that in the extraction process, the ratio of organic phosphorus compound to the nitrile being extracted may range from 1/1000 parts to 90/100 parts; and the ratio of hydrocarbon to organic phosphorus compound may range from 2/1 parts to 100/1 parts, all parts being by weight. The reference discloses monodentate P-containing ligands.

U.S. Pat. No. 6,936,171 claims a process for recovering diphosphite-containing compounds from a mixture comprising diphosphite-containing compounds and organic mononitriles and organic dinitriles, using liquid-liquid extraction, wherein the molar ratio of organic mononitrile present to organic dinitrile is from about 0.65 to about 2.5 and wherein the extraction solvent is a saturated or unsaturated alkane or saturated or unsaturated cycloalkane. The reference discloses a preferred mononitrile to dinitrile ratio range of 0.01 to 2.5. The reference discloses that catalysts comprising diphosphite complexes of Ni allow recovery via liquid-liquid extraction to occur at a higher ratio of organic mononitrile to organic dinitrile than described in U.S. Pat. No. 3,773,809. Consequently, under hydrocyanation reaction conditions that produce mononitrile to dinitrile ratios of greater than 0.65, the unreacted mononitriles do not have to be removed before extraction in order to recover the catalyst. The process may be carried out for the recovery of various bidentate P-containing ligands and nickel complex catalysts thereof, including bidentate P-containing ligands selected from the group consisting of bidentate phosphites and bidentate phosphinites. Introducing monodentate phosphites to the catalyst mixture can improve the extraction recovery.

The reaction product mixture of the present process is suitable for catalyst composition recovery via liquid-liquid extraction through contact with an extraction agent where, for example, the catalyst composition comprises at least one bidentate P-containing ligand, for example a bidentate phosphite or bidentate diphosphinite, and the mononitrile to dinitrile molar ratio is about 2.5 or less. The reaction product mixture is also suitable for catalyst composition recovery via liquid-liquid extraction through contact with an extraction agent where, for example, the catalyst composition comprises a monodentate P-containing ligand and the mononitrile to dinitrile molar ratio is less than about 0.65. U.S. Pat. No. 6,936,171 and published United States Patent Application No. 2007/0260086 describe conditions for recovering catalyst compositions that comprise both bidentate and monodentate P-containing ligands without and with adjustment of the mononitrile to dinitrile molar ration prior to liquid-liquid extraction. When the reaction product mixture is not suitable for catalyst composition recovery via liquid-liquid extraction through contact with an extraction agent under the conditions disclosed in the section below, this will become apparent when liquid-liquid extraction is attempted because phase separation will not occur.

After the reaction product mixture suitable for catalyst composition recovery via liquid-liquid extraction is withdrawn, wherein the ratio of the concentration of 2PN to the concentration of 3PN in the reaction mixture is in the range from about 0.2/1 to about 10/1, at least a portion of the reaction product mixture is extracted with an extraction agent to obtain an extract phase comprising the extraction agent and the catalyst composition and a raffinate phase comprising ADN, MGN, ethylenically unsaturated nitriles, catalyst composition degradation products, and optionally the extraction agent. The extraction agent is selected from the group consisting of aliphatic hydrocarbons, cycloaliphatic hydrocarbons, and mixtures thereof having a boiling point in the range of about 30° C. to about 135° C. For example, n-pentane, n-hexane, n-heptane, n-octane, the corresponding $C_5$-$C_8$ aliphatic hydrocarbon isomers having a boiling point within the specified range, cyclopentane, cyclohexane, cycloheptane, methylcyclohexane, alkyl-substituted cycloaliphatic hydrocarbons having a boiling point within the specified range, and mixtures thereof can be used as the extraction agent. The extraction agent is preferably anhydrous, for example having less than about 100 ppm of water, or for example less than about 50 ppm of water, or for example less than about 10 ppm of water. The extraction agent can be dried by appropriate methods known to those skilled in the art, for example by adsorption or azeotropic distillation.

Extracting the reaction product mixture can be carried out in any appropriate apparatus known to those skilled in the art. Examples of conventional equipment suitable for this extraction include counter-current extraction columns, mixer-settler cascades, or a combination of mixer-settler cascades and columns. For example, counter-current extraction columns equipped with sheet-metal packing as dispersing elements can be used. The counter-current extraction may be carried out in a compartmentalized, agitated extraction column with, for example, a rotating disc column contactor.

The weight ratio of extraction agent to reaction product mixture fed to the extraction process can range from about 0.1 to greater than about 10. For example, the extraction is carried out at a weight ratio of about 0.4 to 2.5, or for example at a ratio of about 0.5 to about 1.5. The pressure within the extraction equipment is from about 0.1 bar to about 10 bar, for example 0.5 bar to about 5 bar, or for example about 1.0 bar to about 2.5 bar. The extraction is carried out at a temperature of about 0° C. to about 100° C., for example at about 20° C. to about 90° C., or for example at about 30° C. to about 80° C.

The extract phase comprising the extraction agent and the catalyst composition is distilled to obtain a first stream comprising the extraction agent and a second stream comprising the catalyst composition. The distillation can be performed in any suitable equipment known to one skilled in the art. The distillation can be carried out in one or more evaporation stages and distillation columns. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

In one embodiment, the distillation apparatus comprises at least one distillation column. The distillation column can be provided with a structured packing section above the feed location to prevent catalyst entrainment in the first stream and to generate an appropriate number of stages of separation. In one embodiment, the extract phase is distilled in two stages with each distillation column having a base temperature of about 150° C. or less. In one embodiment, distilling the extract phase is done in two stages with each distillation column having a base temperature of about 120° C. or less.

The pressure within the distillation equipment is a variable to attain the base temperatures as described above. The pressure in the distillation equipment for the extract phase can range from 0.001 to about 2.0 bar, for example from 0.01 to 1.7 bar, or for example from 0.05 to 1.5 bar. The distillation is carried out in such a way that the temperature in the bottom of the distillation column is from 40° C. to about 150° C., or for example from 80° C. to 140° C., or for example from 90° C. to 120° C.

In the distillation of the extract phase, a first stream comprising the extraction agent is obtained. The first stream contains about 85 to about 100 percent by weight of the extraction agent. The first stream can also contain from about 0 to about 15 percent by weight of ethylenically unsaturated nitrites, including for example 2M2BN, 2PN, 3PN, and 4PN. Optionally, at least a portion of the first stream comprising the extraction agent can be returned to the extraction process. Optionally, the first stream may be further refined to separate the extraction agent from the ethylenically unsaturated nitriles prior to returning the extraction agent to the extraction process and returning the ethylenically unsaturated nitriles to the hydrocyanation reaction.

The first stream may be obtained as a vapor stream in at least one condenser at the top of at least one distillation column, with the extraction agent being condensed from the vapor stream of the distillation column at least partially in at least one condenser and being returned to the distillation column at least partially in the liquid state as reflux.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the extract phase, a second stream comprising the catalyst composition is obtained. Optionally, ethylenically unsaturated nitriles can be added to the base of the column to improve ease of handling the stream where necessary, for example, to limit catalyst composition precipitation in this concentrated second stream. The second stream can be obtained as a bottom product and contains about 0 to about 10 percent by weight of the extraction agent. The remainder of the second stream is comprised of the catalyst composition, optionally including catalyst composition degradation products, ethylenically unsaturated nitrites, and dinitriles.

Optionally, in order to increase the concentration of nickel in the catalyst composition to the desired level, at least a portion of the second stream can be introduced into a reactor where it is contacted in the presence of a nitrile solvent with nickel chloride and a reducing metal which is more electropositive than nickel, as disclosed in U.S. Pat. No. 6,893,996. The stream exiting this reactor is the fifteenth stream and comprises the catalyst composition. The nitrile solvent can be, for example, the ethylenically unsaturated nitrites present in the second stream. Optionally, at least a portion of the fifteenth stream can be returned to the hydrocyanation reaction mixture as a portion of the catalyst composition feed and also as a portion of the ethylenically unsaturated nitrile feed. If desired to maintain or change the molar ratio of P-containing ligand to nickel, P-containing ligand may be added to the reactor where the second stream is contacted with nickel chloride and the reducing metal. The added p-containing ligand may be, for example, recycle P-containing ligand which has been isolated from the process and is being returned to the catalyst composition, or previously-unused P-containing ligand.

Optionally, at least a portion of the second stream is introduced into a 3PN manufacturing process comprising 1,3-butadiene hydrocyanation, 2-methyl-3-butenenitrile isomerization or a combination thereof. Catalyst compositions and reaction conditions useful for 1,3-butadiene hydrocyanation and 2-methyl-3-butenenitrile isomerization are disclosed, for example, in U.S. Pat. Nos. 3,496,215; 3,536,748; 5,693,843; 5,821,378; 5,981,772; and 6,020,516, which are incorporated herein in their entirety.

The raffinate phase comprising ADN, MGN, ethylenically unsaturated nitriles, catalyst composition degradation products, and the extraction agent is distilled to obtain a third stream comprising the extraction agent and a fourth stream comprising ADN, MGN, ethylenically unsaturated nitriles, and catalyst composition degradation products. The distillation can be performed in any suitable equipment known to one skilled in the art. The distillation can be carried out in one or more evaporation stages and distillation columns. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

The pressure within the distillation equipment for the raffinate phase can range from 0.1 to 2.0 bar, for example from 0.2 to 1.3 bar. The distillation is carried out in such a way that the base temperature in the bottom of the distillation apparatus is from 40° C. to 150° C., for example from 80° C. to 130° C.

In one embodiment, the distillation apparatus comprises at least one distillation column operated below atmospheric pressure. In one embodiment, the distillation apparatus comprises at least one distillation column operated above atmospheric pressure. The distillation column can be provided with a structured packing section to generate an appropriate number of stages of separation.

The third stream contains about 80 to about 100 percent by weight, for example about 90 to about 100 percent by weight, of the extraction agent. The third stream can also contain from about 0 to about 20 percent by weight, for example about 0 to about 10 percent by weight of ethylenically unsaturated nitrites, including for example 2M2BN, 2M3BN, 2PN, 3PN, and 4PN. Optionally, at least a portion of the third stream comprising the extraction agent can be returned to the extraction process. Optionally, at least a portion of the third stream can be combined with at least a portion of the first stream, and the combined stream comprising the extraction agent optionally can be returned to the extraction process.

The third stream may be obtained as a vapor stream in at least one condenser at the top of the distillation column, with the extraction agent being condensed from the vapor stream of the distillation column at least partially in at least one condenser and being returned to the distillation column at least partially in the liquid state as reflux.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the raffinate phase, a fourth stream comprising ADN, MGN, ethylenically unsaturated nitriles, and catalyst composition degradation products is obtained. The fourth stream can be obtained as a bottom product and contains 0 to about 10 wt % of the extraction agent, for example about 0.001 to about 6 percent by weight of the extraction agent. The remainder of the fourth stream is comprised of ethylenically unsaturated nitrites including 2PN, 3PN, 4PN, and 2M2BN, dinitriles, and catalyst composition degradation products.

The fourth stream is distilled to obtain a fifth stream comprising ethylenically unsaturated nitriles and a sixth stream comprising ADN, MGN, and catalyst composition degradation products. The distillation can be performed in any suitable equipment known to one skilled in the art. The distillation can be carried out in one or more evaporation stages and distillation columns. The distillation column may have one or more liquid or gaseous sidedraws. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

The pressure within the distillation equipment for the fourth stream can range from 0.001 to 1.0 bar, for example from 0.02 to 0.1 bar. The distillation is carried out in such a way that the temperature in the bottom of the distillation column is from 80° C. to 250° C., for example from 150° C. to 220° C.

In one embodiment, the distillation apparatus comprises at least one distillation column operated below atmospheric pressure. The distillation column can be provided with a structured packing section to generate an appropriate number of stages of separation In the distillation of the fourth stream, a fifth stream comprising ethylenically unsaturated nitrites is obtained. The fifth stream can contain about 50 to about 100 percent by weight, for example about 70 to about 100 percent by weight of ethylenically unsaturated nitriles, with the balance being comprised of the extraction agent and optionally other compounds.

In the distillation of the fourth stream, a sixth stream comprising ADN, MGN, and catalyst composition degradation products is obtained. The sixth stream can be obtained as a bottom product and contains about 0 to 2 wt % ethylenically unsaturated nitrites, for example 0.01 to about 0.5 percent by weight ethylenically unsaturated nitriles. The remainder of the sixth stream is comprised of catalyst composition degradation products and dinitriles.

The sixth stream is distilled to obtain a seventh stream comprising ADN and MGN and an eighth stream comprising catalyst composition degradation products. The distillation can be performed in any suitable equipment known to one skilled in the art. The distillation can be carried out in one or more evaporation stages and distillation columns. The columns may be equipped with one or more sidedraws. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators. Particularly preferred are evaporators which enable a very low evaporator surface temperature and a short contact time on the evaporator, thus minimizing thermal damage to the material being evaporated.

In the distillation of the sixth stream, the pressure within the distillation equipment can range from 0.0001 to 0.5 bar, for example from 0.001 to 0.05 bar. The distillation is carried out in such a way that the temperature in the bottom of the distillation apparatus is from 100° C. to 250° C., or for example from 140° C. to 200° C.

In one embodiment, the distillation apparatus comprises at least one distillation column operated below atmospheric pressure. The distillation column can be provided with a structured packing section to generate an appropriate number of stages of separation.

In the distillation of the sixth stream, a seventh stream comprising ADN and MGN is obtained. The seventh stream contains greater than about 98 percent by weight of dinitriles.

In the distillation of the sixth stream, an eighth stream comprising catalyst composition degradation products is obtained. The eighth stream can be obtained as a bottom product and additionally contains residual dinitriles. As the catalyst composition degradation products are purged from the process, as much of the dinitriles as possible are separated from the catalyst composition degradation products.

The seventh stream is distilled to obtain a ninth stream comprising MGN and a tenth stream comprising ADN. The distillation can be performed in any suitable equipment known to one skilled in the art. The distillation can be carried out in one or more evaporation stages and distillation columns. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

In one embodiment, the distillation apparatus comprises at least one distillation column operated below atmospheric pressure. The distillation column can be provided with a structured packing section to generate an appropriate number of stages of separation.

In the distillation of the seventh stream, a ninth stream comprising MGN is obtained. The ninth stream contains less than about 10 percent by weight ADN, for example less than about 5 percent by weight ADN.

In the distillation of the seventh stream, a tenth stream comprising ADN is obtained. The tenth stream can be obtained as a bottom product and contains greater than about 99 percent by weight of ADN, for example greater than about 99.9 percent by weight ADN.

The fifth stream can further comprise compounds which cannot be converted to ADN. Examples of such compounds include 2M2BN and valeronitrile. The compounds which cannot be converted to ADN will build up in the recycle loop(s) of the process unless they are withdrawn and purged. A distillation process for purging cis-2PN along with 2M2BN from a pentenenitrile stream recycled to a pentenenitrile hydrocyanation reactor is described in U.S. Pat. No. 3,564,040. The present invention enables a simpler and more economical method, which does not require an expensive distillation, for purging compounds that cannot be converted to ADN. For example, in the fifth stream, the total content of compounds which cannot be converted to ADN can be from about 1 percent by weight to about 50 percent by weight, or for example greater than about 10 percent by weight, or for example greater than about 20 percent by weight. Optionally, at least a portion of the fifth stream is withdrawn to purge at least a portion of the compounds which cannot be converted to ADN from the manufacturing process. By allowing the content of these compounds to build up within the fifth stream before purging a portion of the stream from the process, the associated cost of also purging valuable ethylenically unsaturated nitrites, for example 2PN, 3PN, and 4PN, from the fifth stream will decrease. The weight fraction of the amount of the fifth stream purged can be from about 1 percent by weight to about 50 percent by weight, for example less than 10 percent by weight, or for example less than 5 percent by weight.

Optionally, at least a portion of the fifth stream comprising ethylenically unsaturated nitriles is distilled to obtain an eleventh stream comprising cis-2PN and a twelfth stream comprising 3PN. The distillation can be performed in any suitable equipment known to one skilled in the art. The distillation can be carried out in one or more evaporation stages and distillation columns. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

In one embodiment, the distillation apparatus comprises at least one distillation column. The distillation column can be provided with a structured packing section to generate an appropriate number of stages of separation.

In the distillation of the fifth stream, an eleventh stream comprising cis-2PN is obtained. The eleventh stream is enriched in cis-2PN, 2M2BN, and valeronitrile compared to the fifth stream. The eleventh stream also contains, for example, 3PN. At least a portion of the eleventh stream can be purged from the process if desired, to remove compounds which cannot be converted to ADN. Alternatively, or in conjunction with a purge of the eleventh stream, at least a portion of the eleventh stream may be returned to the reaction mixture as a portion of the ethylenically unsaturated nitrile feed.

The eleventh stream may be obtained as a vapor stream in at least one condenser at the top of the distillation column, with the cis-2PN being condensed from the vapor stream of the distillation column at least partially in at least one condenser and being returned to the distillation column at least partially in the liquid state as reflux.

Alternatively, the distillation can be performed with a direct contact condenser so that the condensation is performed in a column section, which is for example provided with a structured column packing, a collecting cup beneath this packing, a liquid discharge feature from the collecting cup, a transfer pumping circuit which is connected to the liquid discharge feature, with a pump and heat exchanger as well as at least one apparatus for adding the transfer-pumped liquid flow to the packing above the collecting cup.

In the distillation of the fifth stream, a twelfth stream comprising 3PN is obtained. The twelfth stream can be obtained as a bottom product and is enriched in 3PN compared to the fifth stream. The twelfth stream also contains other mononitriles, for example, trans-2PN. Optionally, at least a portion of the twelfth stream is returned to the reaction mixture as a portion of the ethylenically unsaturated nitrile feed.

As discussed above, the fifth stream is optionally distilled to obtain the eleventh stream and the twelfth stream. Other uses of the fifth stream are also possible. For example, at least a portion of the fifth stream may be returned to the reaction mixture as a portion of the ethylenically unsaturated nitrile feed. At least a portion of the fifth stream may be combined with the second stream comprising the catalyst composition prior to or subsequent to the second stream being contacted with nickel chloride in the presence of a reducing metal which is more electropositive than nickel, and optionally additional P-containing ligand, to obtain the fifteenth stream, which can be returned to the reaction mixture. At least a portion of the fifth stream can be withdrawn to purge at least a portion of the compounds which cannot be converted to ADN from the manufacturing process and thereby limit their build-up within the reaction zone and the refining streams. These optional uses for the fifth stream may be implemented separately or in combination with one another.

In all of the Figures, each reactor, extractor, and distillation column are shown with feed points and withdrawal points. It is to be understood that the possible locations of these feed and withdrawal points are not necessarily specific to the locations indicated, and that depending on the conditions used to operate the reactor, extractor, or distillation column, and the desired degree of separation desired in the case of an extractor or distillation column, the streams can also be introduced at other feed points and obtained from other withdrawal points not indicated in the Figures.

FIG. 1 schematically illustrates one embodiment of the processes of the invention. Referring to FIG. 1, the HCN, the catalyst composition (abbreviated as "cat" in the Figures), and the ethylenically unsaturated nitriles (abbreviated as "sub" in the Figures) are continuously fed in the presence of at least one Lewis acid in a reaction zone 30 to form a reaction mixture, and the overall feed molar ratio of 2PN to all unsaturated nitriles (X) and the overall feed molar ratio of HCN to all unsaturated nitriles (Z) are controlled by selecting for X a value in the range of about 0.001 to about 0.5; and by selecting for Z a value in the range of about 0.5 to about 0.99, such that the value of quotient Q, wherein $$Q = \frac{X}{\left[\frac{(\text{moles } 3PN + 4PN \text{ in the feed})/}{(\text{moles all unsaturated nitriles in the feed})}\right] - Z}$$

is in the range from about 0.2 to about 10. The reaction product mixture P comprising ADN, MGN, ethylenically unsaturated nitriles, the catalyst composition, and catalyst composition degradation products, wherein the ratio of the concentration of 2PN to the concentration of 3PN in the reaction mixture is in the range from about 0.2/1 to about 10/1, is withdrawn from the reaction zone 30 and is introduced into an extractor 34. A stream EA comprising the extraction agent is also introduced into the extractor 34.

In the extractor 34, the reaction product mixture P is extracted with the extraction agent to obtain an extract phase EP comprising the extraction agent and the catalyst composition and a raffinate phase RP comprising ADN, MGN, ethylenically unsaturated nitrites, catalyst composition degradation products, and the extraction agent. As a result of the extraction, the extract phase EP is depleted in dinitriles, ethylenically unsaturated nitriles, and catalyst composition degradation products, as compared to the reaction product mixture. The raffinate phase RP is depleted in the catalyst composition, as compared to the reaction product mixture.

The extract phase EP is introduced into a distillation column 36, in which the extract phase EP is distilled to obtain a first stream 1 comprising the extraction agent and a second stream 2 comprising the catalyst composition. As a result of the distillation, the first stream 1 is enriched in the extraction agent and depleted in the catalyst composition as compared to the extract phase EP. The second stream 2 is enriched in the catalyst composition and depleted in the extraction agent as compared to the extract phase EP.

FIG. 2 schematically illustrates another embodiment of the processes of the invention, in which the raffinate phase is refined. Referring to FIG. 2, the raffinate phase RP, obtained as previously described, is introduced into a distillation column 38, in which the raffinate phase RP is distilled to obtain a third stream 3 comprising the extraction agent and a fourth stream 4 comprising ADN, MGN, ethylenically unsaturated nitriles, and catalyst composition degradation products. As a result of the distillation, the third stream 3 is enriched in the extraction agent and depleted in ADN, MGN, and catalyst composition degradation products as compared to the raffinate phase RP. The fourth stream 4 is enriched in ADN, MGN, and catalyst composition degradation products and depleted in the extraction agent as compared to the raffinate phase RP.

The fourth stream 4 is introduced into a distillation column 40, in which the fourth stream 4 is distilled to obtain a fifth stream 5 comprising ethylenically unsaturated nitrites and a sixth stream 6 comprising ADN, MGN, and catalyst composition degradation products. As a result of the distillation, the fifth stream 5 is enriched in ethylenically unsaturated nitrites and depleted in dinitriles, including ADN and MGN, and catalyst composition degradation products compared to the fourth stream 4. The sixth stream 6 is enriched in dinitriles, including ADN and MGN, and catalyst composition degradation products and depleted in ethylenically unsaturated nitrites compared to the fourth stream 4.

The sixth stream 6 is introduced into a distillation column 42, in which the sixth stream 6 is distilled to obtain a seventh stream 7 comprising dinitriles, including ADN and MGN, and an eighth stream 8 comprising catalyst composition degradation products. As a result of the distillation, the seventh stream 7 is enriched in dinitriles including ADN and MGN and depleted in catalyst composition degradation products compared to the sixth stream 6. The eighth stream 8 is enriched in catalyst composition degradation products and depleted in dinitriles including ADN and MGN compared to the sixth stream 6.

The seventh stream 7 is introduced into a distillation column 44, in which the seventh stream 7 is distilled to obtain a ninth stream 9 comprising MGN and a tenth stream 10 comprising ADN. The ninth stream 9 is enriched in MGN and depleted in ADN compared to the seventh stream 7. The tenth stream 10 is enriched in ADN and depleted in MGN compared to the seventh stream 7.

The fifth stream 5 is introduced into a distillation column 46, in which the fifth stream 5 is distilled to obtain an eleventh stream 11 comprising cis-2PN and a twelfth stream 12 comprising 3PN. As a result of the distillation, the eleventh stream 11 is enriched in cis-2PN and depleted in 3PN compared to the fifth stream 5. The twelfth stream 12 is enriched in 3PN and depleted in cis-2PN as compared to the fifth stream 5. Optionally, at least a portion of the eleventh stream 11 or the twelfth stream 12 can be returned to the reaction mixture in reaction zone 30 (not shown in FIG. 2).

FIG. 3 schematically illustrates one embodiment of the processes of the invention. Referring to FIG. 3, the second stream 2 comprising the catalyst composition is introduced into a reactor 48, in which the second stream 2 is contacted with nickel chloride and a reducing metal which is more electropositive than nickel in the presence of a nitrile solvent, to obtain a fifteenth stream 15. The fifteenth stream 15 comprises the catalyst composition and is returned to the reaction zone 30 as a portion of the catalyst composition feed to the reaction mixture. The optional addition of P-containing ligand to reactor 48 is not shown in FIG. 3.

In the case where the reaction product mixture is not suitable for catalyst composition recovery via liquid-liquid extraction, the molar ratio of organic mononitrile to organic dinitrile should be adjusted to one where phase separation will occur when contacted with the extraction agent. Adjusting the mononitrile to dinitrile ratio may be done, for example, by addition of dinitrile to the reaction product mixture or by removal of a portion of the ethylenically unsaturated nitriles in the reaction product mixture, for example by distillation.

Distillation of the reaction product mixture can obtain a thirteenth stream comprising ethylenically unsaturated nitrites, for example 2PN, 3PN, 4PN, and 2M2BN, and a fourteenth stream depleted in ethylenically unsaturated nitrites and comprising the catalyst composition, catalyst degradation products, ADN, and MGN. The distillation can be performed in any suitable equipment known to one skilled in the art. The distillation can be carried out in one or more distillation columns. The columns may be equipped with one or more side draws. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators.

The distillation of the reaction mixture may be performed in one stage or in a plurality of stages performed in series at different temperatures and pressures. The evaporator stage may be designed as a distillation column, in which case operation as a rectifying or stripping column is possible. In one embodiment, the evaporator stage is operated as a distillation column in stripping mode.

The actual distillation conditions chosen depend, in part, upon the thermal stability of the catalyst composition used. With more thermally stable catalyst compositions, a higher distillation temperature can be used. With less thermally stable catalyst compositions, a lower distillation temperature should be used to minimize production of catalyst composition degradation products.

The thirteenth stream may be obtained as a vapor stream in at least one condenser at the top of the distillation column, with the ethylenically unsaturated nitriles being condensed from the vapor stream of the distillation column at least partially in at least one condenser and being returned to the distillation column at least partially in the liquid state. The fourteenth stream can be obtained as a bottom product.

At least a portion of the fourteenth stream is extracted with an extraction agent to obtain an extract phase comprising the extraction agent and the catalyst composition and a raffinate phase comprising ADN, MGN, catalyst composition degradation products, ethylenically unsaturated nitriles, and optionally the extraction agent. The extraction agent is selected from the group consisting of aliphatic hydrocarbons, cycloaliphatic hydrocarbons, and mixtures thereof having a boiling point in the range of about 30° C. to about 135° C. For example, n-pentane, n-hexane, n-heptane, n-octane, the corresponding $C_5$-$C_8$ aliphatic hydrocarbon isomers having a boiling point within the specified range, cyclopentane, cyclohexane, cycloheptane, methylcyclohexane, alkyl-substituted cycloaliphatic hydrocarbons having a boiling point within the specified range, and mixtures thereof can be used as the extraction agent. The extraction agent is preferably anhydrous, for example having less than about 100 ppm of water, or for example less than about 50 ppm of water, or for example less than about 10 ppm of water. The extraction agent can be dried by appropriate methods known to those skilled in the art, for example by adsorption or azeotropic distillation.

Extracting the fourteenth stream can be carried out in any appropriate apparatus known to those skilled in the art, as described in the section above for the extraction of the reaction product mixture, and in the same manner as described above for the extraction of the reaction product mixture. The extract phase and the raffinate phase are refined as described in the section above. The extract phase comprising the extraction agent and the catalyst composition is distilled to obtain a first stream comprising the extraction agent and a second stream comprising the catalyst composition. Optionally, in order to increase the concentration of nickel in the catalyst composition to the desired level, at least a portion of the second stream can be introduced into a reactor where it is contacted with nickel chloride and a reducing metal which is more electropositive than nickel to obtain a fifteenth stream which comprises the catalyst composition. The nitrile solvent can be, for example, the ethylenically unsaturated nitrites present in the second stream. Optionally, at least a portion of the fifteenth stream can be returned to the hydrocyanation reaction mixture as a portion of the catalyst composition feed. If desired to maintain or increase the molar ratio of ligand to nickel, P-containing ligand may be added when the second stream is contacted with nickel chloride and the reducing metal. The added P-containing ligand may be, for example, recycle P-containing ligand which has been isolated from the process and is being returned to the catalyst composition, or previously-unused P-containing ligand.

The raffinate phase comprising ADN, MGN, ethylenically unsaturated nitrites, catalyst composition degradation products, and the extraction agent is distilled to obtain the third stream comprising the extraction agent and the fourth stream comprising ADN, MGN, ethylenically unsaturated nitrites, and catalyst composition degradation products. The fourth stream is distilled to obtain the fifth stream comprising ethylenically unsaturated nitriles and the sixth stream comprising ADN, MGN, and catalyst composition degradation products. The six stream is distilled to obtain the seventh stream comprising ADN and MGN and the eighth stream comprising catalyst composition degradation products. The seventh stream is distilled to obtain the ninth stream comprising MGN and the tenth stream comprising ADN.

Streams which further comprise at least one Lewis acid, for example the reaction product mixture, the raffinate phase, the fourth stream, the sixth stream, the fourteenth stream, and combinations thereof can be contacted with ammonia to separate at least partially a metal chloride Lewis acid from the other components of the stream. Removing metal cations from solution in nitrites by contact with anhydrous ammonia is disclosed, for example, in U.S. Pat. No. 3,766,241, which is incorporated herein in its entirety. The ammonia is contacted with the stream containing the Lewis acid, for example by bubbling the ammonia through the stream, and the insoluble material formed may be separated from the solution by settling, filtration, centrifugation, or other procedures known to one of skill in the art. The contacting with ammonia may be performed in any suitable equipment known to one skilled in the art.

FIG. 4 schematically illustrates one embodiment of the processes of the invention. As discussed with regard to FIG. 1 and FIG. 2, the reaction product mixture P withdrawn from the reaction zone 30 is introduced into the extractor 34 along with the stream EA comprising the extraction agent. In the extractor 34, the reaction mixture P is extracted with the extraction agent to obtain an extract phase EP comprising the extraction agent and the catalyst composition and a raffinate phase RP comprising ADN, MGN, ethylenically unsaturated nitrites, catalyst composition degradation products, and optionally the extraction agent. The extract phase EP is introduced into distillation column 36, in which the extract phase EP is distilled to obtain the first stream 1 and the second stream 2. The raffinate phase RP is introduced into distillation column 38, in which distillation of the raffinate phase RP obtains the third stream 3 and the fourth stream 4 comprising ADN, MGN, ethylenically unsaturated nitriles, and catalyst composition degradation products. The reaction product mixture P, the raffinate phase RP, and the fourth stream 4, can further comprise at least one Lewis acid, for example zinc chloride. Referring to FIG. 4, the fourth stream 4 further comprising zinc chloride is introduced into a reactor 50, in which anhydrous ammonia ($NH_3$) is contacted with the fourth stream 4. The insoluble material formed is separated. As a result of the treatment with ammonia, the ammonia-treated fourth stream is depleted in zinc chloride compared to the fourth stream 4 before ammonia treatment. The ammonia-treated fourth stream may be introduced into the distillation column 40 and refined further as disclosed in the above section (not shown in FIG. 4).

Whether the reaction product mixture is extracted directly or extracted after a distillation in which a portion of the ethylenically unsaturated nitrites is removed, a stream comprising a crude bidentate phosphite ligand mixture comprising a phosphite ligand selected from a member of the group represented by Formulas XXXIII and XXXIV may be introduced into the extractor during extraction of the reaction product mixture or the fourteenth stream. Formulas XXXIII and XXXIV, in which all like reference characters have the same meaning, except as further explicitly limited, as shown below:

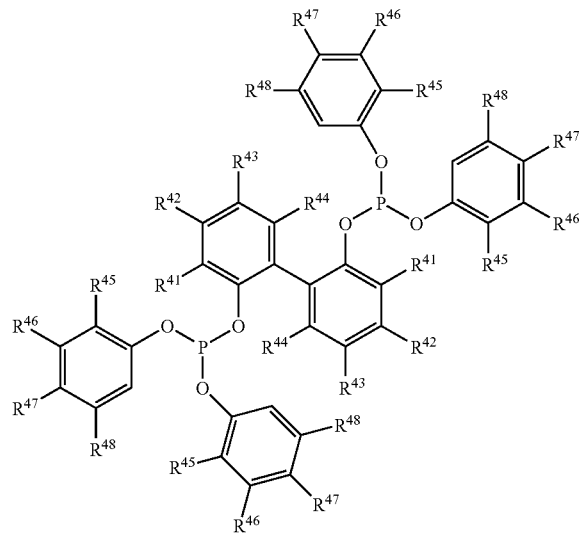

Formula XXXIII

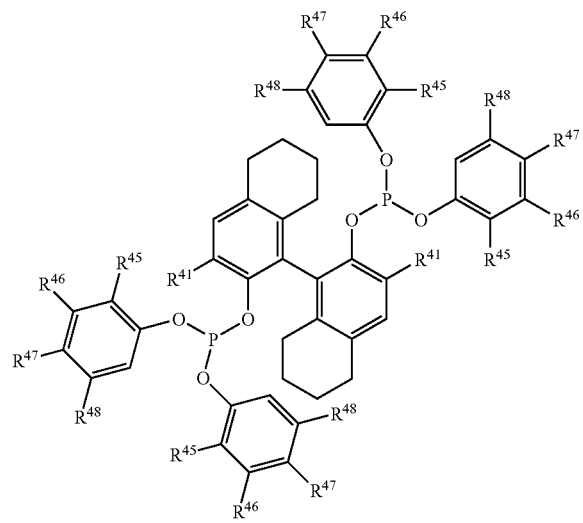

Formula XXXIV wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms. The crude bidentate phosphite ligand mixture may be synthesized by any suitable synthetic means known in the art, as discussed in a previous section. The stream comprising a crude bidentate phosphite ligand mixture can be introduced into the extractor in order to increase the concentration of ligand to a desired level, for example within the second stream as the majority of the ligand will partition into the extract phase.

Embodiments falling within the scope of the present invention may be further understood in view of the following non-limiting examples

EXAMPLES

The following procedures can be used to treat cis-2PN before its use in hydrocyanation reactions. Cis-2-pentenenitrile (98%) produced from a BD and 3PN hydrocyanation process may be obtained commercially from the Sigma-Aldrich Chemical Company. Hydroperoxide impurities can be common in such a reagent and are typically detrimental to hydrocyanation catalyst performance. Hydroperoxide impurities can be measured and reduced in cis-2PN, if necessary, by titration, for example with triphenylphosphine, prior to purification by distillation. Distillation under a nitrogen atmosphere can be utilized to remove the majority of oxygen, water, and peroxides and heavy boilers by taking, for example, a forecut and a heartcut during the distillation. The purified cis-2PN of the heartcut can be transferred into a drybox filled with an inert gas such as nitrogen and can be dried further over 3A molecular sieves (which have been previously dried and degassed under nitrogen).

Bis(1,5-cyclooctadiene)nickel(0), $Ni(COD)_2$, and anhydrous $ZnCl_2$ were purchased from a commercial supplier and also stored under a nitrogen atmosphere in a drybox.

The three protocols of the 2PN Hydrocyanation Test Method are as follows. All three protocols have about 19 wt % initial c2PN.

Protocol #1, Exposure to HCN Vapor:

Under an inert atmosphere such as dry nitrogen or argon, a $Ni(COD)_2$ solution is prepared by dissolving $Ni(COD)_2$ (0.039 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst solution with a zero-valent nickel/multidentate P-containing ligand molar ratio of about 1/1. A cis-2-pentenenitrile (cis-2PN)/$ZnCl_2$ solution is prepared by dissolving $ZnCl_2$ (0.017 g in 1.02 g cis-2PN). A sample of catalyst solution (0.100 mL) is treated with cis-2PN/$ZnCl_2$ solution (0.025 mL); the resulting mixture has cis-2PN/nickel molar ratio of about 123 and a $ZnCl_2$/nickel molar ratio of about 0.96/1. Over a period of 16 hours, the mixture is heated to about 50° C. and exposed to HCN vapor supplied from a reservoir of uninhibited, liquid HCN at ambient temperature (619 mm Hg or 82.5 kPa vapor pressure at 20° C). The reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

Protocol #2, Continuous Flow of HCN Vapor Diluted with Nitrogen Over the Reaction Solution:

Under an inert atmosphere such as dry nitrogen ($N_2$) or argon, $Ni(COD)_2$ solution is prepared by dissolving $Ni(COD)_2$ (0.039 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst solution with a zero-valent nickel/multidentate P-containing ligand molar ratio of about 1/1. A cis-2-pentenenitrile (cis-2PN)/$ZnCl_2$ solution is prepared by dissolving anhydrous $ZnCl_2$ (0.017 g in 1.02 g cis-2PN). A sample of catalyst solution (0.100 mL) is treated with cis-2PN/$ZnCl_2$ solution (0.025 mL); the resulting mixture has cis-2PN/nickel molar ratio of about 123 and a $ZnCl_2$/nickel molar ratio of about 0.96/1. A HCN/$N_2$ gas mixture (about 35% HCN vol/vol) is produced by bubbling dry nitrogen gas through anhydrous, uninhibited, liquid HCN at 0° C. and swept (about 1 to about 5 mL/min) over the catalyst/c2PN mixture heated to about 50° C. After 16 hours, the reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

Protocol #3, Sealed Vial:

Under an inert atmosphere such as dry nitrogen or argon, a $Ni(COD)_2$ solution is prepared by dissolving $Ni(COD)_2$ (0.065 g) in toluene (2.79 g). A toluene solution, or other appropriate solvent solution, of the multidentate P-containing ligand or a ligand mixture comprising a multidentate P-containing ligand to be tested (0.230 mL of 0.062 mol total multidentate P-containing ligand/L of toluene) is treated with the $Ni(COD)_2$ solution (0.320 mL) and thoroughly mixed to provide a catalyst solution with a zero-valent nickel/multidentate P-containing ligand molar ratio of about 1/1. A cis-2-pentenenitrile (cis-2PN)/HCN/$ZnCl_2$ solution is prepared by combining anhydrous $ZnCl_2$ (0.0406 g), freshly distilled, uninhibited, liquid HCN (0.556 g), and cis-2PN (1.661 g). Into a 2 mL GC vial, a sample of catalyst solution (0.092 mL) is treated with cis-2PN/HCN/$ZnCl_2$ solution (0.034 mL) then the vial is sealed with an aluminum septum cap; the resulting mixture has cis-2PN/nickel molar ratio of about 123, HCN/nickel molar ratio of about 123, and a $ZnCl_2$/nickel molar ratio of about 0.96/1. Over a period of 16 hours, the mixture is heated to about 50° C. The reaction mixture is then cooled to ambient temperature, treated with acetonitrile (0.125 mL), and analyzed by gas chromatography for the amount of ADN, MGN, and 2-ethylsuccinonitrile produced, in order to calculate the percent conversion of 2PN to dinitriles.

In the following Examples, unless stated otherwise, all operations were carried out under a nitrogen atmosphere using a drybox or standard Schlenk techniques. Examples of the inventive continuous hydrocyanation process have been performed in a single-stage 18-mL glass continuous stirred-tank reactor (CSTR), the general design of which has been described in U.S. Pat. Nos. 4,371,474, 4,705,881, and 4,874,884, the entire disclosures of which are incorporated herein by reference. The reactor consisted of a crimp-baffled round bottomed glass vessel, jacketed to allow controlling the temperature of the reaction mixture with fluid flow from an external, controlled, fluid-heating temperature bath. All reagents were introduced into the reaction vessel via syringe pumps, through sidearms fitted with rubber septa. The reactor was fitted with an overflow arm through which the reaction product flowed by gravity into a product receiver. Agitation and mixing of the reaction mixture was provided by magnetic stirring. A small nitrogen purge was constantly applied to the vapor space of the reactor to maintain an inert atmosphere.

The trans-3PN (95 wt %) and cis-2PN (98 wt %) utilized in the hydrocyanation experiments described below originated from a commercial ADN plant that hydrocyanates BD and pentenenitriles. Trans-3PN and cis-2PN produced from a BD and pentenenitrile hydrocyanation process may be obtained commercially from the Sigma-Aldrich Chemical Company. Each pentenenitrile was distilled under a nitrogen atmosphere then stored in a nitrogen-filled drybox.

Examples 1 through 5 and Comparative Examples A through C were performed and Example 6 is performed using a catalyst composition wherein the multidentate P-containing ligand was (or is, in the case of Example 6) a bidentate phosphite ligand selected from a member of the group represented by Formula XXXIII or Formula XXXIV, in which all like reference characters have the same meaning, except as further explicitly limited:

Formula XXXIII

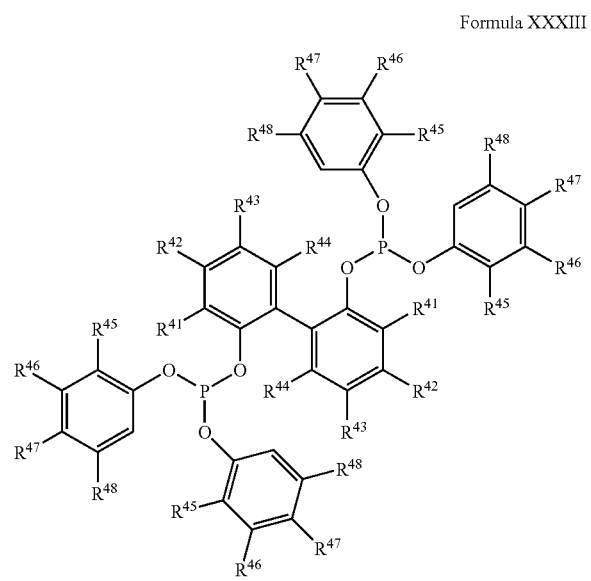

Formula XXXIV

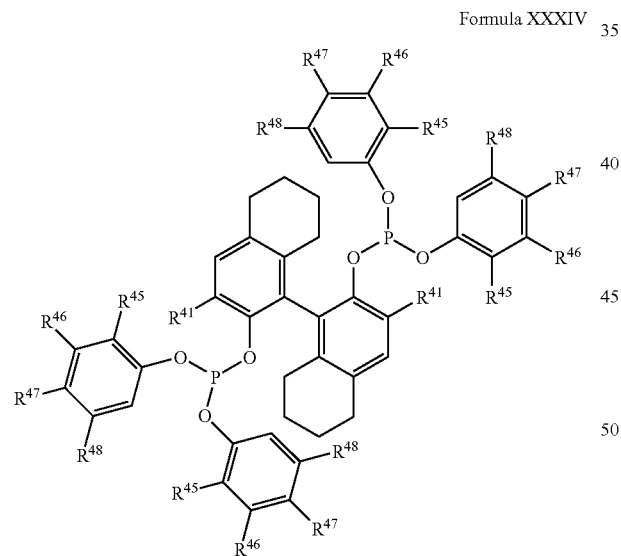

wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$ $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms.

Ligand "A" of Example 1 may be prepared by any suitable synthetic means known in the art. For example, 3,3'-diisopropyl-5,5',6,6'-tetramethyl-2,2'-biphenol can be prepared by the procedure disclosed in United States Published Patent Application No. 2003/0100802, which is incorporated herein by reference, in which 4-methylthymol can undergo oxidative coupling to the substituted biphenol in the presence of a copper chlorohydroxide-TMEDA complex (TMEDA is N,N,N',N'-tetramethylethylenediamine) and air.

The phosphorochloridite of o-cresol, $(C_7H_7O)_2PCl$, can be prepared, for example, by the procedure disclosed in United States Published Patent Application No. 2004/0106815, which is incorporated herein by reference. To selectively form this phosphorochloridite, anhydrous triethylamine and o-cresol can be added separately and concurrently in a controlled manner to $PCl_3$ dissolved in an appropriate solvent under temperature-controlled conditions.

The reaction of this phosphorochloridite with the 3,3'-diisopropyl-5,5',6,6'-tetramethyl-2,2'-biphenol to form the desired Ligand "A" can be performed, for example, according to the method disclosed in U.S. Pat. No. 6,069,267, which is hereby incorporated by reference. The phosphorochloridite can be reacted with 3,3'-diisopropyl-5,5',6,6'-tetramethyl-2,2'-biphenol in the presence of an organic base to form Ligand "A", which can be isolated according to techniques well known in the art, as also described in U.S. Pat. No. 6,069,267. The monodentate phosphite impurities in Ligand "A" prepared by this method would have the following structures.

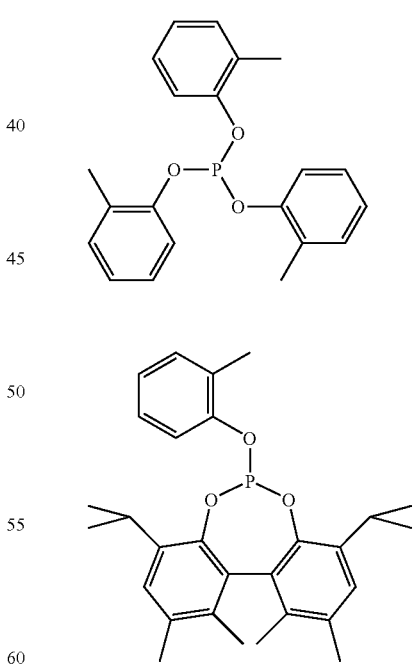

Likewise, Ligand "B" can be prepared from 3,3'-diisopropyl-5,5',6,6'-tetramethyl-2,2'-biphenol and the phosphorochloridite of 2,4-xylenol, $((C_8H_9O)_2PCl$. The monodentate phosphite impurities in Ligand "B" prepared by this method would have the following structures.

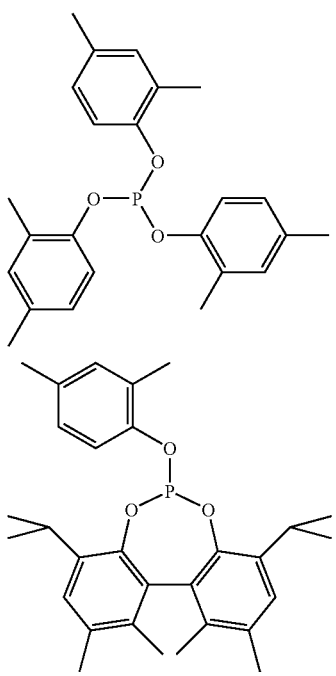

Likewise, Ligand "C" can be prepared from 3,3'-diisopropyl-5,5',6,6',7,7',8,8'-octahydro-2,2'-binaphthol, prepared by the method described in United States Patent Application No. 2003/0100803, and the phosphorochloridite of o-cresol, $(C_7H_7O)_2PCl$. The monodentate phosphite impurities in Ligand "C" prepared by this method would have the following structures.

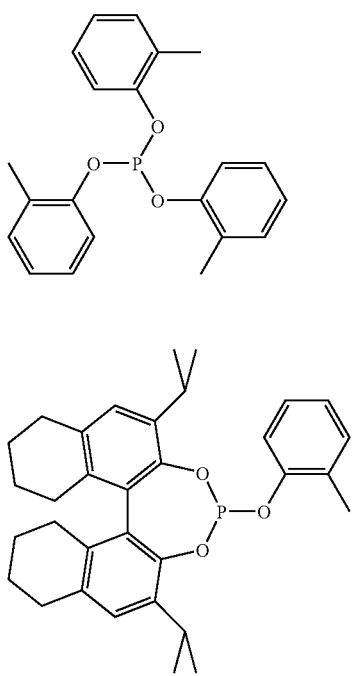

The anhydrous, uninhibited HCN feed to the reactor was delivered as a pentenenitrile (PN) solution (40% HCN by weight). The composition of the pentenenitriles used to make the feed solutions was determined by the desired pentenenitrile feed composition to the reactor. The amount of methylbutenenitriles in the pentenenitrile feed solutions was negligible. The ligand-Ni catalyst composition was synthesized by the reaction of $Ni(COD)_2$ with a slight excess of the corresponding bidentate phosphite ligand (approximately 1.2 to 1.4 molar equivalents/Ni) in toluene solvent at ambient temperatures, as generally described in U.S. Pat. No. 6,120,700. After removal of the toluene solvent and volatile materials under vacuum, a corresponding quantity of anhydrous Lewis acid promoter was added to the solid residue of the catalyst composition, and the entire mixture was dissolved in a corresponding mixture of pentenenitriles. The resulting pentenenitrile solution comprising catalyst composition and promoter was thus fed to the reactor as described below.

At startup, the reaction vessel was charged with about 9 mL of the pentenenitrile solution comprising catalyst composition and promoter. The continuous hydrocyanation reaction was then initiated by turning on the feed of both the pentenenitrile solution comprising composition and promoter and the HCN solution. Periodic samples of the reactor product flowing to the receiver were analyzed by gas chromatographic (GC) analysis to determine nitrile product compositions used in calculating reactor conversions and yields.

Definitions

PN's=all pentenenitrile isomers of empirical formula $C_5H_7N$, including all methylbutenenitrile isomers of empirical formula $C_5H_7N$ 2PN=cis- and trans-2-pentenenitriles 3PN=cis- and trans-3-pentenenitriles 4PN=4-pentenenitrile DN's=all dinitrile isomers of empirical formula $C_6H_8N_2$ (includes ADN, MGN and ESN)

ADN=adiponitrile

MGN=2-methylglutaronitrile

ESN=ethylsuccinonitrile g/hr=gram/hour conversion=moles reacted/moles fed yield=moles produced/moles (3PN+4PN) reacted mol % DN's=molar fraction DN's/(PN's+DN's) in reactor product mol % 2PN feed=molar fraction 2PN/(PN's+DN's) in reactor feed mol % 2PN product=molar fraction 2PN/(PN's+DN's) in reactor product mol % 3PN product=molar fraction 3PN/(PN's+DN's) in reactor product linearity=moles ADN/moles (ADN+MGN+ESN) produced

Example 1

The inventive continuous hydrocyanation process was demonstrated using Ligand "A," shown below, and FeCl$_2$ as the Lewis acid promoter.

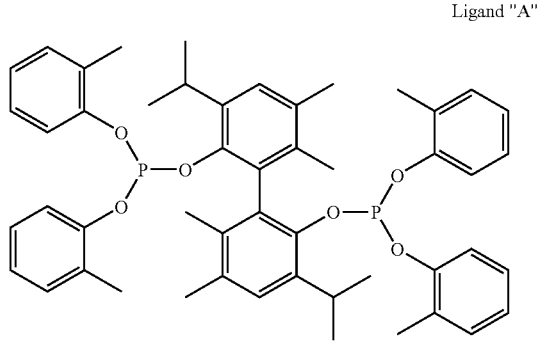

Ligand "A"

Target reaction rate=1.6×10$^{-4}$ moles HCN/liter–second
Temperature=50° C.
mol % 2PN feed=12.8%
The target feed rates of the reaction components were as follows.

| Reagent | Feed Rate, g/hr |
|---|---|
| HCN[a] | 0.29 |
| 3,4PN (3PN + 4PN) | 1.01 |
| 2PN | 0.15 |
| Ni catalyst, calculated as Ni metal | 0.0010 |
| Total Ligand[b] | 0.029 |
| FeCl$_2$ promoter | 0.0015 |

Notes:
[a]HCN excluding PN solvent.
[b]Mixture of Ligand "A" and corresponding monodentate phosphites as described above.

The overall feed molar ratio of 2PN to all unsaturated nitriles was about 0.13 and the overall feed molar ratio of HCN to all unsaturated nitriles was about 0.75.

The averaged GC analyses of reactor product samples taken from 92 to 100 hours from the inception of continuous flow indicated the following steady-state results.

| | |
|---|---|
| 3,4PN Conversion | 86% |
| mol % DN's | 73.6% |
| mol % 2PN product | 14.0% |
| mol % 3PN product | 11.8% |
| 2PN Yield | 1.5% |
| Linearity | 94.2% |
| ADN Yield | 92.8% |

The ratio of the concentration of 2PN to the concentration of 3PN in the reaction mixture was about 1.2.

Example 2

The inventive continuous hydrocyanation process was demonstrated using Ligand "A" and ZnCl$_2$ as the Lewis acid promoter.
Target reaction rate=1.6×10$^{-4}$ moles HCN/liter–second
Temperature=50° C.
mol % 2PN feed=20.6%
The target feed rates of the reaction components were as follows.

| Reagent | Feed Rate, g/hr |
|---|---|
| HCN[a] | 0.29 |
| 3,4PN (3PN + 4PN) | 0.94 |
| 2PN | 0.25 |
| Ni catalyst, calculated as Ni metal | 0.0013 |
| Total Ligand[b] | 0.027 |
| ZnCl$_2$ promoter | 0.0020 |

Notes:
[a]HCN excluding PN solvent.
[b]Mixture of Ligand "A" and corresponding monodentate phosphites as described above.

The overall feed molar ratio of 2PN to all unsaturated nitriles was about 0.21 and the overall feed molar ratio of HCN to all unsaturated nitrites was about 0.70.

The averaged GC analyses of reactor product samples taken from 49 to 53 hours from the inception of continuous flow indicated the following steady-state results.

| | |
|---|---|
| 3,4PN Conversion | 90.7% |
| mol % DN's | 71.9% |
| mol % 2PN product | 20.3% |
| mol % 3PN product | 7.2% |
| 2PN Yield | 0.0% |
| Linearity | 95.0% |
| ADN Yield | 95.0% |

The ratio of the concentration of 2PN to the concentration of 3PN in the reaction mixture was about 2.8.

Comparative Example A

The following is a comparative example of a continuous hydrocyanation reaction using Ligand "A" and ZnCl$_2$ as promoter without the addition of 2PN to the reactor feed.

Target reaction rate=2.3×10$^{-4}$ moles HCN/liter–second
Temperature=50° C.
mol % 2PN feed=0.1%[c]
The target feed rates of the reaction components were as follows.

| Reagent | Feed Rate, g/hr |
|---|---|
| HCN[a] | 0.38 |
| 3,4PN (3PN + 4PN) | 1.63 |
| 2PN | 0.0016 |
| Ni catalyst, calculated as Ni metal | 0.0018 |
| Total Ligand[b] | 0.045 |
| ZnCl$_2$ promoter | 0.0048 |

Notes:
[a]HCN excluding PN solvent.
[b]Mixture of Ligand "A" and corresponding monodentate phosphites as described above.
[c]2PN impurity in the 3PN feed material.

The overall feed molar ratio of 2PN to all unsaturated nitriles was about 0.001 and the overall feed molar ratio of HCN to all unsaturated nitrites was about 0.70.

The averaged GC analyses of reactor product samples taken from 46 to 54 hours from the inception of continuous flow indicated the following steady-state results.

| | |
|---|---|
| 3,4PN Conversion | 71.1% |
| mol % DN's | 68.7% |
| mol % 2PN product | 2.1% |
| mol % 3PN product | 28.0% |
| 2PN Yield | 2.5% |
| Linearity | 94.9% |
| ADN Yield | 92.5% |

The ratio of the concentration of 2PN to the concentration of 3PN in the reaction mixture was about 0.08.

Example 3

The inventive continuous hydrocyanation process was demonstrated using Ligand "B," shown below, and $FeCl_2$ as the Lewis acid promoter.

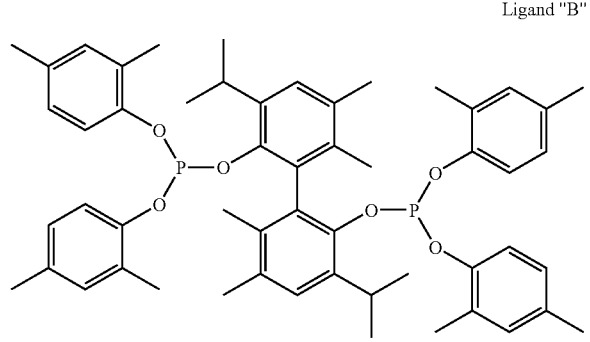

Ligand "B"

Target reaction rate=$1.6 \times 10^{-4}$ moles HCN/liter-second
Temperature=50° C.
mol % 2PN feed=15.4%
The target feed rates of the reaction components were as follows.

| Reagent | Feed Rate, g/hr |
|---|---|
| HCN[a] | 0.29 |
| 3,4PN (3PN + 4PN) | 0.95 |
| 2PN | 0.175 |
| Ni catalyst, calculated as Ni metal | 0.0013 |
| Total Ligand[b] | 0.029 |
| $FeCl_2$ promoter | 0.0019 |

Notes:
[a] HCN excluding PN solvent.
[b] Mixture of Ligand "B" and corresponding monodentate phosphites as described above.

The overall feed molar ratio of 2PN to all unsaturated nitriles was about 0.15 and the overall feed molar ratio of HCN to all unsaturated nitriles was about 0.80.

The averaged GC analyses of reactor product samples taken from 69 to 78 hours from the inception of continuous flow indicated the following steady-state results.

| | |
|---|---|
| 3,4PN Conversion | 92.3% |
| mol % DN's | 77.4% |
| mol % 2PN product | 15.6% |
| mol % 3PN product | 6.4% |
| 2PN Yield | 0.3% |
| Linearity | 94.7% |
| ADN Yield | 94.4% |

The ratio of the concentration of 2PN to the concentration of 3PN in the reaction mixture was about 2.4.

Example 4

The inventive continuous hydrocyanation process was demonstrated using Ligand "B" and $ZnCl_2$ as the Lewis acid promoter.
Target reaction rate=$1.6 \times 10^{-4}$ moles HCN/liter-second
Temperature=50° C.
mol % 2PN feed=14.9%
The target feed rates of the reaction components were as follows.

| Reagent | Feed Rate, g/hr |
|---|---|
| HCN[a] | 0.29 |
| 3,4PN (3PN + 4PN) | 0.96 |
| 2PN | 0.17 |
| Ni catalyst, calculated as Ni metal | 0.0013 |
| Total Ligand[b] | 0.029 |
| $ZnCl_2$ promoter | 0.0020 |

Notes:
[a] HCN excluding PN solvent.
[b] Mixture of Ligand "B" and corresponding monodentate phosphites as described above.

The overall feed molar ratio of 2PN to all unsaturated nitriles was about 0.15 and the overall feed molar ratio of HCN to all unsaturated nitriles was about 0.77.

The averaged GC analyses of reactor product samples taken from 66 to 73 hours from the inception of continuous flow indicated the following steady-state results.

| | |
|---|---|
| 3,4PN Conversion | 90.7% |
| mol % DN's | 76.2% |
| mol % 2PN product | 15.5% |
| mol % 3PN product | 7.7% |
| 2PN Yield | 0.7% |
| Linearity | 95.4% |
| ADN Yield | 94.7% |

The ratio of the concentration of 2PN to the concentration of 3PN in the reaction mixture was about 2.0.

Comparative Example B

The following is a comparative example of a continuous hydrocyanation reaction using Ligand "B" and $ZnCl_2$ as promoter without the addition of 2PN to the reactor feed.
Target reaction rate=$2.3 \times 10^{-4}$ moles HCN/liter-second
Temperature=50° C.
mol % 2PN feed=0.3%[c]
The target feed rates of the reaction components were as follows.

| Reagent | Feed Rate, g/hr |
|---|---|
| HCN[a] | 0.38 |
| 3,4PN (3PN + 4PN) | 1.63 |

-continued

| Reagent | Feed Rate, g/hr |
|---|---|
| 2PN | 0.0049 |
| Ni catalyst, calculated as Ni metal | 0.0018 |
| Total Ligand[b] | 0.049 |
| ZnCl$_2$ promoter | 0.0048 |

Notes:
[a]HCN excluding PN solvent.
[b]Mixture of Ligand "B" and corresponding monodentate phosphites as described above.
[c]2PN impurity in the 3PN feed material.

The overall feed molar ratio of 2PN to all unsaturated nitriles was about 0.003 and the overall feed molar ratio of HCN to all unsaturated nitriles was about 0.70.

The averaged GC analyses of reactor product samples taken from 45 to 48 hours from the inception of continuous flow indicated the following steady-state results.

| | |
|---|---|
| 3,4PN Conversion | 73.9% |
| mol % DN's | 71.5% |
| mol % 2PN product | 2.1% |
| mol % 3PN product | 25.2% |
| 2PN Yield | 2.5% |
| Linearity | 95.4% |
| ADN Yield | 93.0% |

The ratio of the concentration of 2PN to the concentration of 3PN in the reaction mixture was about 0.08.

Example 5

The inventive continuous hydrocyanation process was demonstrated using Ligand "C," shown below, and ZnCl$_2$ as the Lewis acid promoter.

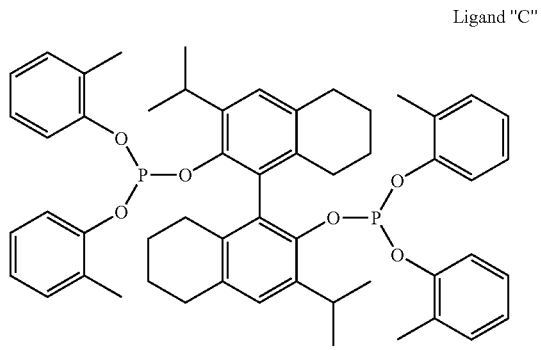

Ligand "C"

Target reaction rate=$1.6 \times 10^{-4}$ moles HCN/liter–second
Temperature=50° C.
mol % 2PN feed=20.4%
The target feed rates of the reaction components were as follows.

| Reagent | Feed Rate, g/hr |
|---|---|
| HCN[a] | 0.29 |
| 3,4PN (3PN + 4PN) | 0.94 |
| 2PN | 0.24 |
| Ni catalyst, calculated as Ni metal | 0.0013 |

| Reagent | Feed Rate, g/hr |
|---|---|
| Total Ligand[b] | 0.029 |
| ZnCl$_2$ promoter | 0.0020 |

Notes:
[a]HCN excluding PN solvent.
[b]Mixture of Ligand "C" and corresponding monodentate phosphites as described above.

The overall feed molar ratio of 2PN to all unsaturated nitriles was about 0.20 and the overall feed molar ratio of HCN to all unsaturated nitriles was about 0.73.

The averaged GC analyses of reactor product samples taken from 71 to 79 hours from the inception of continuous flow indicated the following steady-state results.

| | |
|---|---|
| 3,4PN Conversion | 90.0% |
| mol % DN's | 70.4% |
| mol % 2PN product | 21.1% |
| mol % 3PN product | 7.9% |
| 2PN Yield | 1.0% |
| Linearity | 95.0% |
| ADN Yield | 94.1% |

The ratio of the concentration of 2PN to the concentration of 3PN in the reaction mixture was about 2.7.

Comparative Example C

The following is a comparative example of a continuous hydrocyanation reaction using Ligand "C" and ZnCl$_2$ as promoter without the addition of 2PN to the reactor feed.
Target reaction rate=$2.3 \times 10^{-4}$ moles HCN/liter–second
Temperature=50° C.
mol % 2PN feed=0.4%[c]
The target feed rates of the reaction components were as follows.

| Reagent | Feed Rate, g/hr |
|---|---|
| HCN[a] | 0.40 |
| 3,4PN (3PN + 4PN) | 1.70 |
| 2PN | 0.0068 |
| Ni catalyst, calculated as Ni metal | 0.0019 |
| Total Ligand[b] | 0.051 |
| ZnCl$_2$ promoter | 0.0050 |

Notes:
[a]HCN excluding PN solvent.
[b]Mixture of Ligand "C" and corresponding monodentate phosphites as described above.
[c]2PN impurity in the 3PN feed material.

The overall feed molar ratio of 2PN to all unsaturated nitriles was about 0.004 and the overall feed molar ratio of HCN to all unsaturated nitriles was about 0.70.

The averaged GC analyses of reactor product samples taken from 48 to 53 hours from the inception of continuous flow indicated the following steady-state results.

| | |
|---|---|
| 3,4PN Conversion | 72.6% |
| mol % DNs | 70.3% |
| mol % 2PN product | 2.1% |
| mol % 3PN product | 26.6% |
| 2PN Yield | 2.4% |
| Linearity | 94.9% |
| ADN Yield | 92.6% |

The ratio of the concentration of 2PN to the concentration of 3PN in the reaction mixture was about 0.08.

Example 6

Example 6 demonstrates the integrated, continuous process of the invention operating at steady state. This Example uses a catalyst composition wherein the multidentate P-containing ligand is the bidentate P-containing ligand referred to in the section above as "Ligand B". Ligand B is prepared as described in the section above.

Ligand B, anhydrous $NiCl_2$, zinc powder, and 3PN are contacted according to the method disclosed in U.S. Pat. No. 6,893,996, which is incorporated herein by reference, to prepare a catalyst composition. The catalyst composition is used in the hydrocyanation described below.

A refined 3PN stream containing greater than 97% by weight 3PN and 4PN together, a recycle stream of ethylenically unsaturated nitriles and compounds which cannot be converted to ADN, and the nitriles contained in the catalyst composition and zinc chloride feeds are contacted with HCN in the presence of zinc chloride promoter and the catalyst composition comprising Ligand B and a zero-valent nickel, Ni(0), in a 1.2:1 Ligand B:Ni(0) molar ratio in a reaction zone consisting of a stainless steel, draft-tube, back-mixed reactor. The composite feed to the reaction zone contains 54.3 wt % 3PN and 4PN together, 12.9 wt % 2PN, 28.2 wt % other ethylenically unsaturated nitriles, and 17.3 wt % HCN resulting in an overall feed molar ratio of 2PN to all unsaturated nitriles (ratio X) of about 0.14 and an overall feed molar ratio of HCN to all unsaturated nitriles (ratio Z) of about 0.75. The molar ratio of HCN being fed to Ni(0) being fed is 450:1 and the molar ratio of HCN being fed to zinc chloride being fed is 540:1. The reaction zone is maintained at 50° C. with a hold up time of about 10 hours to achieve about 94% conversion of 3PN with HCN being the limiting reactant and to produce a reaction mixture containing about 10 wt % 2PN, about 3.3 wt % 3PN and 4PN together, about 3.7 wt % MGN, about 69.0 wt % ADN, and about 0.4 wt % ESN. Hence, the ratio of the concentration of 2PN to the concentration of 3PN in the reaction product mixture is about 3.

The reaction product mixture is introduced into an extractor comprising three mixer-settlers in series which are maintained at 50° C. The cyclohexane extraction agent to reaction product mixture weight ratio is 0.7. The extract phase obtained from the extractor contains about 85 wt % cyclohexane, about 6 wt % ethylenically unsaturated nitriles, less than about 2 wt % dinitriles, about 3.5 wt % Ligand B, and about 0.12 wt % Ni(0). Cyclohexane is mixed with the raffinate from the second stage and fed to the third mixer-settler. The raffinate phase obtained from the extractor contains about 12 wt % cyclohexane, about 10 wt % 2PN, about 13 wt % other ethylenically unsaturated nitriles, about 64 wt % dinitriles, and trace quantities of Ligand B and catalyst composition degradation products.

The extract phase is introduced into a distillation column and continuously distilled. The column head pressure is about 4.8 psia (0.33 bar) and the column bottom temperature is 100° C. The first stream is withdrawn from the column and contains about 90 wt % cyclohexane, the remainder of the stream being composed of ethylenically unsaturated nitriles. The column base is heated by circulating bottoms material through an external steam-heated exchanger. To limit precipitation of catalyst composition solids, ethylenically unsaturated nitriles are introduced to the base of the column at a ratio of about 0.1 (weight/weight) to the column feed. The second stream is obtained by withdrawing a portion from the circulating bottoms material and contains about 20 wt % Ligand B and about 0.7 wt % Ni, with the remainder of the stream being composed of dinitriles, catalyst composition degradation products, and ethylenically unsaturated nitriles.

The raffinate phase is introduced into a distillation column and continuously distilled to remove the majority of cyclohexane. The column head pressure is about 4.5 psia (0.31 bar) and the column bottom temperature is 90° C. The third stream is withdrawn from the column and contains about 93 wt % cyclohexane with the balance being ethylenically unsaturated nitriles. The fourth stream is obtained by withdrawing a portion from the circulating bottoms material and contains about 2 wt % cyclohexane.

The fourth stream is introduced into an ammonia reactor in which anhydrous ammonia is fed at a molar ratio of 2:1 to the zinc chloride in the feed. The product from the reactor is sent to a reactor/crystallizer. The product from the reactor/crystallizer is centrifuged to remove the ammonia-zinc chloride solids.

The ammonia-treated fourth stream is introduced into a distillation column and continuously distilled. The column head pressure is about 1.2 psia (0.083 bar) and the column bottom temperature is 202° C. The fifth stream is withdrawn from the top of the column and contains 6 wt % cyclohexane, 38 wt % 2PN, 22 wt % 3PN and 4PN together, and about 34 wt % compounds which cannot be converted to ADN. The column base is heated by circulating bottoms material through an external steam-heated exchanger. The sixth stream is obtained by withdrawing a portion from the circulating bottoms material and contains 93.3 wt % ADN, 5.9 wt % MGN, and smaller quantities of ethylenically unsaturated nitriles and catalyst composition degradation products.

After withdrawing 2 wt % of the fifth stream to purge a portion of the compounds which cannot be converted to ADN from the manufacturing process and thereby limit their build-up within the reaction zone and refining streams, another portion of the fifth stream is returned to the reaction zone as a recycle stream.

The sixth stream is introduced into a distillation apparatus and continuously distilled. The apparatus is operated over a pressure range of about 0.10 psia (0.0069 bar) to about 0.40 psia (0.028 bar) and a temperature range of about 160° C. to about 185° C. The seventh stream is withdrawn from the apparatus and contains about 93 wt % ADN and 6.0 wt % MGN. The eighth stream is withdrawn from the apparatus and contains about 75 wt % catalyst composition degradation products and about 20 wt % dinitriles.

The seventh stream is introduced into a distillation column and continuously distilled. The column head pressure is about 0.39 psia (0.027 bar) and the column bottom temperature is about 200° C. The ninth stream is withdrawn from the reflux back to the column and contains about 95 wt % MGN and ESN together and about 2.0 wt % ADN. The column base is heated by circulating bottoms material through an external steam-heated exchanger. The tenth stream is obtained by withdrawing a portion from the circulating bottoms material and contains greater than 99.9% ADN.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A hydrocyanation process to produce adiponitrile and other dinitriles having six carbon atoms, the process comprising:
   a) forming a reaction mixture in the presence of at least one Lewis acid, said reaction mixture comprising ethylenically unsaturated nitriles having five carbon atoms, hydrogen cyanide, and at least one catalyst composition, by continuously feeding the ethylenically unsaturated nitriles, the hydrogen cyanide, and the catalyst composition; wherein
   the catalyst composition comprises a zero-valent nickel and at least one bidentate phosphorus-containing ligand;
   wherein the bidentate phosphorus-containing ligand is selected from the group consisting of a phosphite, a phosphonite, a phosphinite, a phosphine, and a mixed phosphorus-containing ligand or a combination of such ligands
   and the bidentate phosphorus-containing ligand gives acceptable results according to at least one protocol of the 2-Pentenenitrile Hydrocyanation Test Method;
   b) controlling X and Z, wherein
      X is the overall feed molar ratio of 2-pentenenitriles to all unsaturated nitriles; and
      Z is the overall feed molar ratio of hydrogen cyanide to all unsaturated nitriles;
      by selecting
         a value for X in the range of about 0.001 to about 0.5; and
         a value for Z in the range of about 0.5 to about 0.99;
      such that the value of quotient Q, wherein $$Q = \frac{X}{\left[\frac{(\text{moles } 3PN + 4PN \text{ in the feed})/}{(\text{moles all unsaturated nitriles in the feed})}\right] - Z}$$

is in the range from about 0.2 to about 10, wherein 3PN is 3-pentenenitriles and 4PN is 4-pentenenitrile;
   c) withdrawing a reaction product mixture comprising adiponitrile, 2-methyl-glutaronitrile, ethylenically unsaturated nitriles, the catalyst composition, and catalyst composition degradation products; and
   wherein the ratio of the concentration of 2-pentenenitriles to the concentration of 3-pentenenitriles in the reaction mixture is in the range from about 0.2/1 to about 10/1;
   d) extracting at least a portion of the reaction product mixture with an extraction agent selected from the group consisting of aliphatic hydrocarbons, cycloaliphatic hydrocarbons, and mixtures thereof to obtain an extract phase comprising the extraction agent and the catalyst composition and a raffinate phase comprising adiponitrile, 2-methylglutaronitrile, ethylenically unsaturated nitriles, catalyst composition degradation products, and the extraction agent; and
   e) distilling the extract phase to obtain a first stream comprising the extraction agent and a second stream comprising the catalyst composition.

2. The process of claim 1, further comprising distilling the raffinate phase to obtain a third stream comprising the extraction agent and a fourth stream comprising adiponitrile, 2-methylglutaronitrile, ethylenically unsaturated nitriles, and catalyst composition degradation products.

3. The process of claim 2, further comprising distilling the fourth stream to obtain a fifth stream comprising ethylenically unsaturated nitriles and a sixth stream comprising adiponitrile, 2-methylglutaronitrile, and catalyst composition degradation products.

4. The process of claim 3, further comprising distilling the sixth stream to obtain a seventh stream comprising adiponitrile and 2-methylglutaronitrile and an eighth stream comprising catalyst degradation products.

5. The process of claim 4, further comprising distilling the seventh stream to obtain a ninth stream comprising 2-methylglutaronitrile and a tenth stream comprising adiponitrile.

6. The process of claim 5, further comprising returning at least a portion of the first stream, at least a portion of the third stream, or combinations thereof to the extraction.

7. The process of claim 5, wherein at least a portion of the fifth stream is returned to the reaction mixture.

8. The process of claim 5, wherein at least a portion of the second stream is combined with at least a portion of the fifth stream, and optionally returned to the reaction mixture.

9. The process of claim 5, wherein the fifth stream further comprises compounds which cannot be converted to adiponitrile, and wherein at least a portion of the fifth stream is withdrawn to purge at least a portion of the compounds which cannot be converted to adiponitrile.

10. The process of claim 9, wherein in the fifth stream the total content of compounds which cannot be converted to adiponitrile is greater than about 10 percent by weight.

11. The process of claim 5, further comprising distilling at least a portion of the fifth stream to obtain an eleventh stream comprising cis-2-pentenenitrile and an twelfth stream comprising 3-pentenenitrile.

12. The process of claim 11, wherein at least a portion of the twelfth stream is returned to the reaction mixture.

13. The process of claim 1, further comprising contacting at least a portion of the second stream with nickel chloride and a reducing metal which is more electropositive than nickel in the presence of a nitrile solvent to obtain a fifteenth stream, and optionally returning at least a portion of the fifteenth stream to the reaction mixture.

14. The process of claim 2, further comprising contacting with ammonia at least one stream selected from the group consisting of the reaction product mixture, the raffinate phase, the fourth stream, the sixth stream, and combinations thereof, wherein the reaction product mixture, the raffinate phase, the fourth stream, the sixth stream, and combinations thereof further comprise at least one Lewis acid.

15. The process of claim 1, wherein distilling the extract phase is done in two stages with each distillation column base temperature being about 150° C. or less.

16. The process of claim 1, wherein distilling the extract phase is done in two stages with each distillation column base temperature being about 120° C. or less.

17. The process of claim 1, wherein the catalyst composition further comprises at least one monodentate phosphite ligand.

18. The process of claim 1, wherein the bidentate phosphorus-containing ligand is a phosphite ligand selected from a member of the group represented by Formula XXXIII and Formula XXXIV:

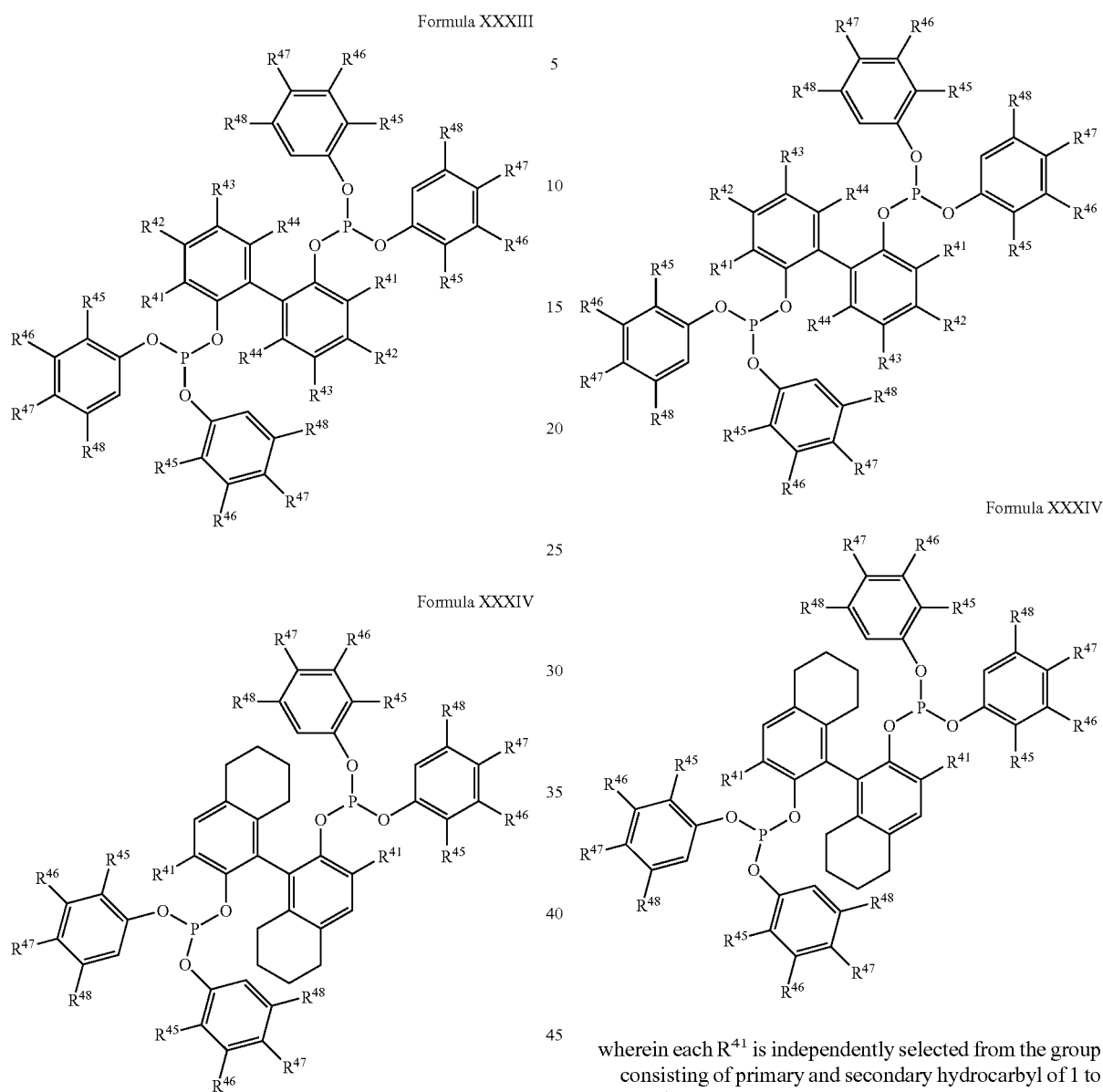

wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms.

19. The process of claim 18, further comprising introducing a stream comprising a crude bidentate phosphite ligand mixture comprising a phosphite ligand selected from a member of the group represented by Formula XXXIII and Formula XXXIV:

wherein each $R^{41}$ is independently selected from the group consisting of primary and secondary hydrocarbyl of 1 to 6 carbon atoms;

each $R^{45}$ is independently selected from the group consisting of methyl, ethyl, and primary hydrocarbyl of 3 to 6 carbon atoms; and each $R^{42}$, $R^{43}$, $R^{44}$, $R^{46}$, $R^{47}$, and $R^{48}$ is independently selected from the group consisting of H, aryl, and a primary, secondary, or tertiary hydrocarbyl of 1 to 6 carbon atoms, to the extraction of the reaction product mixture.

20. The process of claim 1, wherein the at least one Lewis acid comprises zinc chloride and the extraction agent comprises cyclohexane.

21. The process of claim 1 or claim 5, wherein at least a portion of the second stream is introduced into a 3-pentenenitrile manufacturing process comprising 1,3-butadiene hydrocyanation, 2-methyl-3-butenenitrile isomerization, or a combination thereof.

22. The hydrocyanation process of claim 1 wherein the bidentate phosphorus-containing ligand is selected from the group consisting of a phosphite, a phosphonite, a phosphinite, a phosphine, and a mixed phosphorus-containing ligand or a combination of such ligands represented by Formula I:

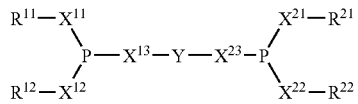

Formula I wherein
$X^{11}, X^{12}, X^{13}, X^{21}, X^{22}, X^{23}$ independently represent oxygen or a single bond;
$R^{11}, R^{12}$ independently represent identical or different, single or bridged organic radicals;
$R^{21}, R^{22}$ independently represent identical or different, single or bridged organic radicals; and
Y represents a bridging group.

* * * * *